US011524989B2

(12) United States Patent
Spits et al.

(10) Patent No.: US 11,524,989 B2
(45) Date of Patent: Dec. 13, 2022

(54) AML ANTIGENS AND USES THEREOF

(71) Applicant: KLING BIOTHERAPEUTICS B.V., Amsterdam (NL)

(72) Inventors: Hergen Spits, Amsterdam Zuidoost (NL); Marijn Aletta Gillissen, Amsterdam Zuidoost (NL); Martijn Kedde, Amsterdam Zuidoost (NL); Mette Deborah Hazenberg, Amsterdam Zuidoost (NL); Paula Maria Wilhelmina van Helden, Amsterdam Zuidoost (NL); Wouter Pos, Amsterdam Zuidoost (NL)

(73) Assignee: KLING BIOTHERAPEUTICS B.V., Amsterdam (NL)

( * ) Notice: Subject to any disclaimer, the term of this patent is extended or adjusted under 35 U.S.C. 154(b) by 0 days.

(21) Appl. No.: 15/737,924

(22) PCT Filed: Jun. 24, 2016

(86) PCT No.: PCT/NL2016/050449
§ 371 (c)(1),
(2) Date: Dec. 19, 2017

(87) PCT Pub. No.: WO2016/209079
PCT Pub. Date: Dec. 29, 2016

(65) Prior Publication Data
US 2018/0170998 A1  Jun. 21, 2018

(30) Foreign Application Priority Data

Jun. 24, 2015 (EP) ...................... 15173662
Jan. 8, 2016 (EP) ...................... 16150621

(51) Int. Cl.
| C07K 14/435 | (2006.01) |
| C07K 14/705 | (2006.01) |
| C07K 16/28 | (2006.01) |
| G01N 33/574 | (2006.01) |
| A61K 38/00 | (2006.01) |

(52) U.S. Cl.
CPC ...... *C07K 14/70596* (2013.01); *C07K 14/435* (2013.01); *C07K 16/2896* (2013.01); *G01N 33/57426* (2013.01); *A61K 38/00* (2013.01); *C07K 2317/732* (2013.01); *C07K 2317/734* (2013.01); *G01N 2333/70596* (2013.01)

(58) Field of Classification Search
CPC ............ C07K 14/70596; C07K 14/435; C07K 16/2896; C07K 2317/734; C07K 2317/732; G01N 33/57426; G01N 2333/70596; A61K 38/00
See application file for complete search history.

(56) References Cited

U.S. PATENT DOCUMENTS

| 7,399,847 B1 | 7/2008 | Seed et al. |
| 8,742,070 B2 * | 6/2014 | Timmerman .... G01N 33/54353 530/323 |
| 9,005,974 B2 | 4/2015 | Spits |

FOREIGN PATENT DOCUMENTS

| EP | 1974017 B1 | 11/2013 |
| WO | 2006121240 A1 | 11/2006 |
| WO | 2007146172 A2 | 12/2007 |
| WO | 2015093949 A2 | 6/2015 |

OTHER PUBLICATIONS

Document_Leuk_Human, 1990.*
Expert Opinion on Drug Discover, 2016, vol. 11, No. 12, 1151-1163 (Year: 2016).*
Bowie et al (Science, 1990, 247:1306-1310) (Year: 1990).*
Burgess et al (J. Cell Biol. 111:2129-2138, 1990) (Year: 1990).*
Lazar et al (Mol. Cell. Biol., 8:1247-1252, 1988) (Year: 1988).*
Gillissen, M., et al.; Patient-derived antibody recognizes a unique CD43 epitope expressed on all AML and has antileukemia activity in mice; Blood Advances, Aug. 22, 2017, vol. 1, No. 19, pp. 1551-1564, XP055462743.
Bennett, J.M., et al., 1976; Proposals for the Classification of the Acute Leukaemias. French-American-British (FAB) Co-operative Group, British Journal of Haematology, vol. 33, No. 4, pp. 451-458.
Borche, L., et al., 2005; CD43 monoclonal antibodies recognize the large sialoglycoprotein of human leukocytes; European Journal of Immunology, vol. 17, No. 10, pp. 1523-1526.
Hanly, W. Carey, et al., 1995; Review of Polyclonal Antibody Production Procedures in Mammals and Poultry; ILAR Journal, vol. 37, No. 3, pp. 93-118.
de Laurentiis, A., et al., 2011; Mass Spectrometry-Based Identification of the Tumor Antigen UN1 as the Transmembrane CD43 Sialoglycoprotein; Molecular & Cellular Proteomics, vol. 10, No. 5, pp. 1-12.
Mialcovati, L., et al., 2013; Diagnosis and treatment of primary myelodysplastic syndromes in adults: recommendations from the European LeukemiaNet; Blood, vol. 122, No. 17, pp. 2943-2964.
Miller, P.H., et al., 2013; Enhanced normal short-term human myelopoiesis in mice engineered to express human-specific myeloid growth factors; Blood, vol. 121, No. 5, pp. e1-e4.
Schmid, K., et al., 1992; Amino acid sequence of human plasma galactoglycoprotein: Identity with the extracellular region of CD43 (sialophorin); Proceedings of the National Academy of Sciences of the United States of America, vol. 89, No. 2, pp. 663-667.
Shelley, C.S., et al., 1989; Molecular characterization of sialophorin (CD43), the lymphocyte surface sialoglycoprotein defective in Wiskott-Aldrich syndrome; Proceedings of the National Academy of Sciences of the United States of America, vol. 86, pp. 2819-2823.

(Continued)

*Primary Examiner* — Sudhakar Katakam
(74) *Attorney, Agent, or Firm* — Gianna Julian-Arnold; Saul Ewing Arnstein & Lehr LLP

(57) ABSTRACT

The present invention provides novel compounds comprising an antigen of AML cells, and uses thereof.

9 Claims, 22 Drawing Sheets

Specification includes a Sequence Listing.

(56) References Cited

OTHER PUBLICATIONS

Tuccillo, F.M., et al., 2014; Cancer-associated CD43 glycoforms as target of immunotherapy; National Institute of Health, Mol Cancer Ther. vol. 13, No. 3; pp. 752-762.

Matsuoka, S., et al., 1995; A Novel Type of Cell Death of Lymphocytes Induced by a Monoclonal Antibody without Participation of Complement; The Journal of Experimental Medicine, Rockefeller University Press, US, vol. 181, pp. 2007-2015.

Zhang, C., et al., 1998; A cell surface receptor defined by a mAb mediates a unique type of cell death similar to oncosis; Proceedings of the National Academy of Sciences, National Academy of Sciences, US, vol. 95, pp. 6290-6295.

Bakker, A.B., et al., Nov. 15, 2004; C-type lectin-like molecule-1: a novel myeloid cell surface marker associated with acute myeloid leukemia; Cancer Research, vol. 64, pp. 8443-8450.

Bhat, N.M., et al., 1977; Rapid cytotoxicity of human B lymphocytes induced by VH4-34 (VH4.21) gene-encoded monoclonal antibodies, II; Clinical and Experimental Immunology, 1977, vol. 108, pp. 151-159.

Biernacki, M.A., et al., Feb. 1, 2010; Efficacious immune therapy in chronic myelogenous leukemia (CML) recognizes antigens that are expressed on CML progenitor cells; American Association for Cancer Research, vol. 70, pp. 906-915.

Brady, Hugh J.M.; 2004 Methods in Molecular Biology, vol. 282.

Chen, Y., et al., 1999; Selection and analysis of an optimized anti-VEGF antibody: crystal structure of an affinity-matured Fab in complex with antigen; Journal of Molecular Biology, vol. 293, pp. 865-881.

Diehl, S.A., et al., 2008; STAT3-mediated up-regulation of BLIMP1 Is coordinated with BCL6 down-regulation to control human plasma cell differentiation; The Journal of Immunology, vol. 180, pp. 4805-4815.

Drexler, H.G., et al., 1998; History and classification of human leukemia lymphoma cell lines; Leukemia and Lymphoma, vol. 31, pp. 305-316.

Hernandez, A.M., et al., 2011; Anti-NeuGcGM3 Antibodies, Actively Elicited by Idiotypic Vaccination in Nonsmall Cell Lung Cancer Patients Induce Tumor Cell Death by an Oncosis-Like Mechanism; The Journal of Immunology, vol. 186, pp. 3735-3744.

Kattah, N.H., et al., 2010; The U1-snRNP complex: structural properties relating to autoimmune pathogenesis in rheumatic diseases. Immunol Reviews; vol. 233, pp. 126-145.

Kepp, O., et al., Mar. 2011; Cell death assays for drug discovery; Nature Reviews Drug Discovery, vol. 10, pp. 221-237.

Majeti, R., et al., Jul. 24, 2009; CD47 is an adverse prognostic factor and therapeutic antibody target on human acute myeloid leukemia stem cells; Cell, vol. 138, pp. 286-299.

Schlenk, R.F., et al., May 1, 2008; Mutations and treatment outcome in cytogenetically normal acute myeloid leukemia; The New England Journal of Medicine, vol. 358, pp. 1909-1918.

Schmid, C., et al, Nov. 1, 2007; Donor lymphocyte infusion in the treatment of first hematological relapse after allogeneic stem-cell transplantation in adults with acute myeloid leukemia: a retrospective risk factors analysis and comparison with other stralegies by the EBMT Acute Leukemia Working Party; Journal of Clinical Oncology, vol. 25, No. 31, pp. 4938-4945.

Schmiedel, B.J., et al., Apr. 2013; Generation and Preclinical Characterization of a Fc-optimized GITR-Ig Fusion Protein for Induction of NK Cell Reactivity Against Leukemia; The American Society of Gene & Cell Therapy, Molecular Therapy, vol. 21, No. 4, pp. 877-886.

Singh, R., et al., 2011; The non-steroidal anti-inflammatory drugs Sulindac sulfide and Diclofenac induce apoptosis and differentiation in human acute myeloid leukemia cells through an AP-1 dependent pathway; Apoptosis, vol. 16, pp. 889-901.

Tsuchiya, S., et al., 1980, Establishment and characterization of a human acute monocytic leukemia cell line (THP-1); Int J Cancer, vol. 26, pp. 171-176.

Walther, R.B., et al., 2012; Acute myeloid leukemia stem cells and CD33-targeted immunotherapy; Blood, vol. 119, No. 26, pp. 6198-6208.

Wu, C.J., et al., Sep. 2000; Detection of a potent humoral response associated with immune-induced remission of chronic myelogenous leukemia, The Journal of Clinical Investigation, vol. 106, No. 5, pp. 705-714.

Gillissen, M., et al.; Unique and Potent Tumor Specific Antibodies in Graft . . . ; Blood Journal, Dec. 6, 2014, 124(21); XP2755806.

Tuccillo, F., et al.; Aberrant Glycosylation as Biomarker for Cancer: Focus on CD43; BioMed Research International; vol. 2014, Article ID 742831; pp. 1-13; XP2755807.

Buckley, S., et al.; Update on Antigen-Specific Immunotherapy of Acute Myeloid Leukemia; Curr Hematol Malig Rep (2015), vol. 10, pp. 65-75; XP2755808.

Kwakkenbos, M., et al.; Stable long-term cultures of self-renewing B cells and their applications; Immunological Reviews, 2016, vol. 270, pp. 65-77; XP2755809.

Gillissen, M., et al.; B lymphocytes are important effector cells in anti-AML responses after allogeneic hematopoietic stem cell transplantation; haematologica, 2015; vol. 100, p. 277, XP9189239.

Hazenberg, M., et al.; Tumor-specific glycosylated CD43 is a novel and highly specific target for acute myeloid leukemia and myelodysplastic syndrome; haematologica, 2016; vol. 101, p. 191, XP9192174.

Kwakkenbos, M., et al.; Generation of stable monoclonal antibody-producing B cell receptor-positive human memory B cells by genetic programming; Nature Medicine, Jan. 2010, vol. 16, No. 1, pp. 123-129.

Kim, S., et al.; Characterization of Two Novel mAbs Recognizing Different Epitopes on CD43; Immune Network, Jun. 2014, vol. 14, No. 3, pp. 164-170.

Hasegawa, K., et al.; Glycosylation Status of CD43 Protein is Associated with Resistance of Leukemia Cells to CTL-Mediated Cytolysis; PLOS ONE, Mar. 24, 2016, vol. 10, No. 1371, pp. 1-14.

Alvarado, M., et al.; MEM-59 monoclonal antibody detects a CD43 epitope involved in lymphocyte activation; Eur. J. Immunol., 1995, vol. 25, pp. 1051-1055.

Kyoizumi, S., et al.; Expression Characteristics and Stimulatory Functions of CD43 in Human CD4+ Memory T Cells: Analysis Using a Monoclonal Antibody to CD43 That Has a Novel Lineage Specificity; The Journal of Immunology, 2004, vol. 172, pp. 7246-7253.

De Smet, W. et al.; A new CD43 monoclonal antibody induces homotypic aggregation of human leucocytes through a CD11a/CD18-dependent and -independent mechanism; Immunology, 1993, vol. 79, pp. 46-54.

Office Action (and English Translation thereto), dated Jun. 1, 2020, issued in corresponding Japanese Patent Application No. 2017-566723.

Sjölander, Anders, et al.; ISCOMs: an adjuvant with multiple functions; Journal of Leukocyte Biology, Dec. 1998, vol. 64, pp. 713-723.

* cited by examiner

Heavy chain

Recombined from gene segments:
IGHV4-4*02 F
IGHD6-19*01 F
IGHJ5*02 F

AMINO ACID:
Fw1 QGRLQESGPGLVKPSETLTLTCAVSGGSSVS
CDR1 SPNWWT
Fw2 WVRQAPGKGLEWIG
CDR2 EIYYGGRVSYNSALRS
Fw3 RVTISSDRSKEEFSLKLRSVTAADTAIYYC
CDR3 AGQKNIGCGYSSCFISWFDT
Fw4 WGQGIAVTVSS

NUCLEOTIDE:
Fw1 cag ggg cga ctg cag gag tcg ggc cca gga ctg gtg aag cct tcg gag acc ctg acc ctc acg tgc gct gtg tcc ggt ggc tcc tcc gtc agc CDR1 agt cct aac tgg tgg act Fw2 tgg gtc cgc cag gcc ccc ggg aag ggg ctg gag tgg att gga CDR2 gaa atc tat tat ggt ggg aga gtg agc tac aac tcg gcc ctc agg agt Fw3 cga gtc acc att tca tca gac agg tcc aaa gag gag ttc tcc ctg aaa ctg agg tct gtg acc gcc gcg gac acg gcc ata tat tat tgt CDR3 gcg ggt caa aaa aat att ggc tgt ggt tac agc agt tgc ttt atc agt tgg ttc gac acc Fw4 tgg gga cag gga att gcg gtc acc gtc tcc tca

Figure 1 continued

<u>Light chain</u>

Recombined from gene segments:
IGKV4-1*01 F
IGKJ2*01 F

AMINO ACID:
Fw1 DIVMTQSPDSLAVSLGERATIAC
CDR1 KSSQTILQRSNHLNYLA
Fw2 WYQQKPGQPPKVLIY
CDR2 WASTRES
Fw3 GVPDRFSGSGSGTDFTLTINSLQAEDVAVYYC
CDR3 HQYYTTPQT
Fw4 FGQGTKVEIK

NUCLEOTIDE:
Fw1 gac atc gtg atg acc cag tct cca gac tcc ctg gct gtg tct ctg ggc gag agg gcc acc atc gcc tgc CDR1 aag tcc agc cag act att tta caa agg tcc aac cat ttg aac tac tta gct Fw2 tgg tac cag cag aaa cca gga cag cct cct aaa gtg ctc att tat CDR2 tgg gca tct acc cgg gaa tcc Fw3 ggg gtc cct gac cga ttc agt ggc agc ggg tct ggg aca gat ttc act ctc acc atc aac agc ctg cag gct gag gat gtg gca gtt tat tac tgt CDR3 cac caa tat tat act act ccg cag act Fw4 ttt ggc cag ggg acc aag gtg gag atc aaa

Figure 2

| | Binding |
|---|---|
| AML | |
| Kasumi 3 | + |
| HL60 | ++ |
| THP-1 | ++ |
| KG1a | ++ |
| SH2 | ++ |
| MonoMac6 | ++ |
| Molm13 | ++ |
| CML K562 | ++ |
| Primary isolated AML Blasts | |
| Patient 77: AML FAB:M0 | ++ |
| BL-052:AML FAB: m1, from CML | ++ |
| BL-038:AML FAB: M4 | ++ |
| BL-046:AML FAB: M4 | ++ |
| BL-051:AML FAB: M4 | ++ |
| BL-053:AML FAB: M5, from MDS | ++ |
| BL-058:AML from MDS | ++ |
| Patient 81: AML from MDS | ++ |
| BL-060: biphenotypic AML | ++ |

B cell lymphoma's　　　　　　　　Binding
OCl Ly7 (DLBCL)
Ramos (Burkitt's lymphoma)

Primary isolated B-cell leukemia's
BL-019: B-All
BL-021: Pre B-All
BL-048: Pre B-All T cell leukemia's
Jurkat Primary isolated T cell leukemia
T ALL, BL-040

Multiple Myeloma
MM1.s
RPMI8226
U266

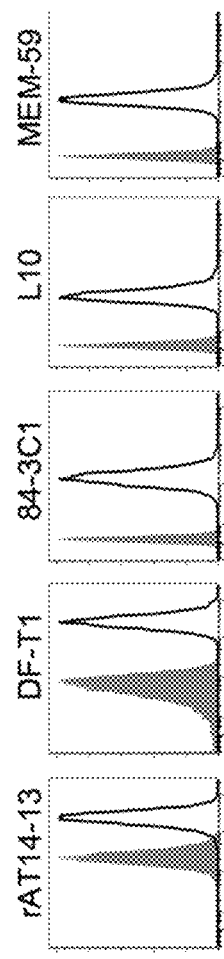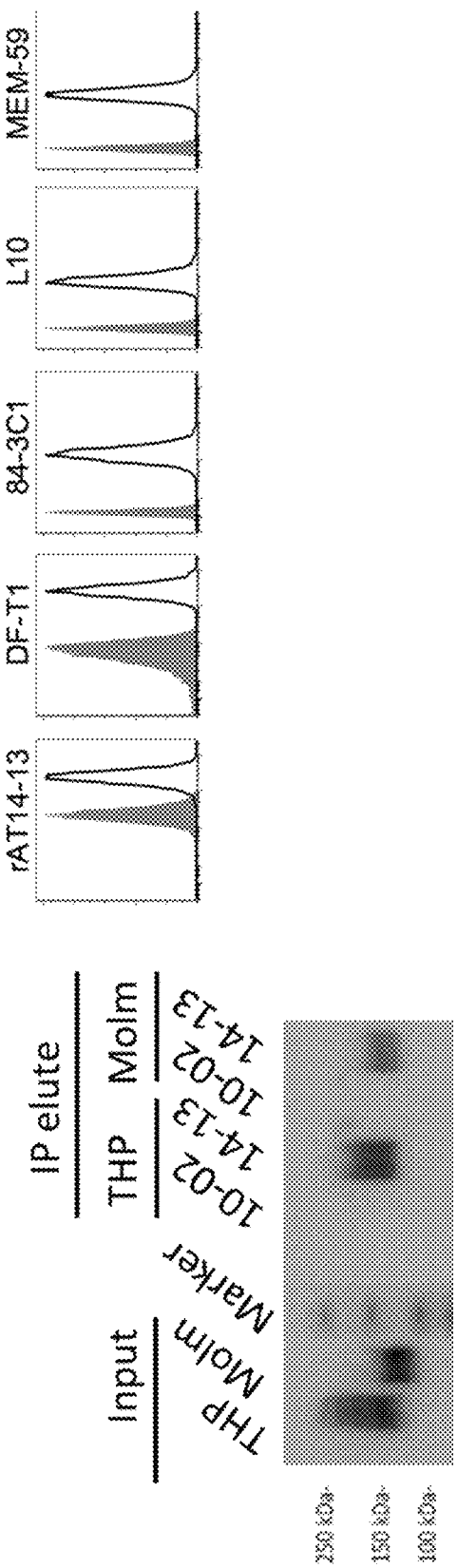

|  | rAT-14-13 biotin | rAT10-002 biotin | 84-3C1-PE | L10-FITC | MEM59-FITC | DFT1 xxx |
|---|---|---|---|---|---|---|
| 84-3C1-PE | - | - | ND | + | + | ND |
| L10-FITC | - | - | + | ND | ND | ND |
| MEM59-FITC | - | - | + | ND | ND | ND |
| DFT1 xxx | + | - | - | - | - | - |
| rAT14-13 biotin | - | - | - | - | - | - |
| rAT10-002 biotin | - | - | - | - | - | - |

+ = does compete
- = does not compete
ND = not determined

Figure 11B
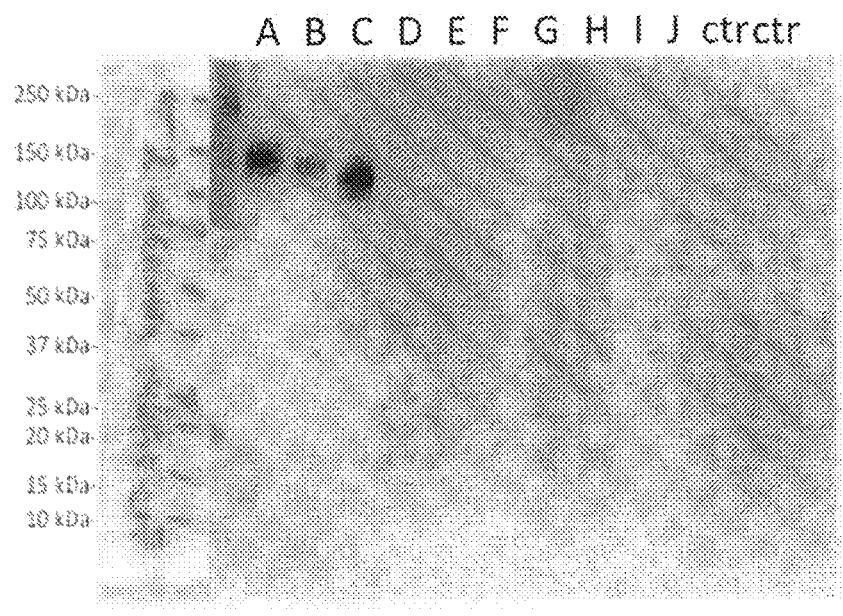
aCD43 Mem59
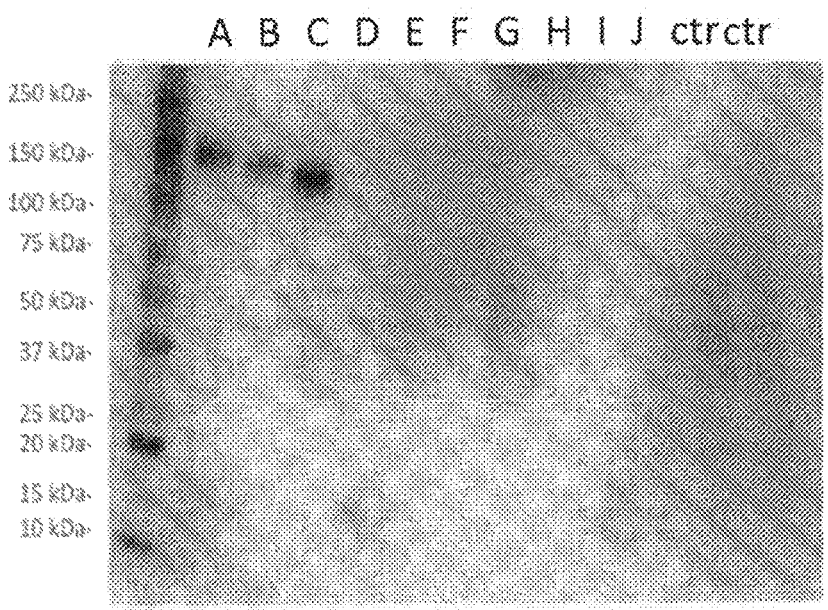
aCD43 DF-T1

Figure 14

AML with recurrent genetic abnormalities

| Blasts from patients | AT14-013 | CD43 Mem-59 | CD43 L10 | CD43 DFT1 |
|---|---|---|---|---|
| BL-068 | +++ | +++ | +++ | +++ |
| BL-010 | +++ | +++ | - | +++ |
| BL-025 | ++++ | ++++ | - | ++++ |
| BL-060 | ++++ | +++ | - | +++ |
| BL-061 | +++ | ++ | - | ++ |
| BL-039 | +++ | +++ | + | +++ |
| BL-051 | ++++ | +++ | + | +++ |
| BL-031 | +++ | +++ | + | +++ |
| BL-059 | ++++ | +++ | ++ | +++ |
| BL-043 | +++ | ++ | + | ++ |
| BL-045 | +++ | ++ | ++ | ++ |
| BL-057 | +++ | +++ | - | ++ |
| BL-037 | +++ | ++ | + | ++ |

AML with myelodysplasia-related changes

|  | AT14-013 | CD43 Mem-59 | CD43 L10 | CD43 DFT1 |
|---|---|---|---|---|
| BL-014 | +++ | +++ | + | ++ |
| BL-055 | ++ | ++ | - | ++ |
| BL-052 | ++++ | ++ | ++ | ++ |
| BL-054 | +++ | ++ | + | +++ |

Therapy-related myeloid neoplasms

|  | AT14-013 | CD43 Mem-59 | CD43 L10 | CD43 DFT1 |
|---|---|---|---|---|
| BL-047 | +++ | +++ | + | +++ |
| BL-028 | ++ | - | - | + |

Figure 14 (Continued)

Acute Myeloid leukemia, not otherwise specified

|  | AT14-013 | CD43 Mem-59 | CD43 L10 | CD43 DFT1 |
|---|---|---|---|---|
| Donor 80 | ++++ | ++++ | - | +++ |
| Donor 86 | ++++ | ++++ | +++ | +++ |
| BL-007 | ++++ | ++++ | - | ++++ |
| BL-030 | ++++ | +++ | - | +++ |
| Donor 77 | ++++ | +++ | + | +++ |
| Donor 87 | ++++ | ++ | + | ++ |
| BL-009 | ++++ | +++ | + | +++ |
| BL-046 | +++ | ++ | - | ++ |
| BL-053 | +++ | +++ | - | +++ |

Myelodysplastic syndromes

|  | AT14-013 | CD43 Mem-59 | CD43 L10 | CD43 DFT1 |
|---|---|---|---|---|
| BL-011 | +++ | +++ | - | +++ |
| BL-022 | +++ | ++ | ++ | +++ |
| BL-062 | +++ | ++ | - | +++ |
| BL-032 | ++ | +++ | - | ++ |
| BL-033 | +++ | +++ | - | ++ |
| BL-058 | ++ | - | - | ++ |
| Donor 81 | +++ | +++ | - | +++ |
| BL-042 | ++ | +++ | ++ | +++ |

Healthy cells

|  | AT14-013 | CD43 Mem-59 | CD43 L10 | CD43 DFT1 |
|---|---|---|---|---|
| CD3+ T cells | - | +++ | ++ | +++ |
| Tonsil | - | +++ | + | +++ |

Figure 15
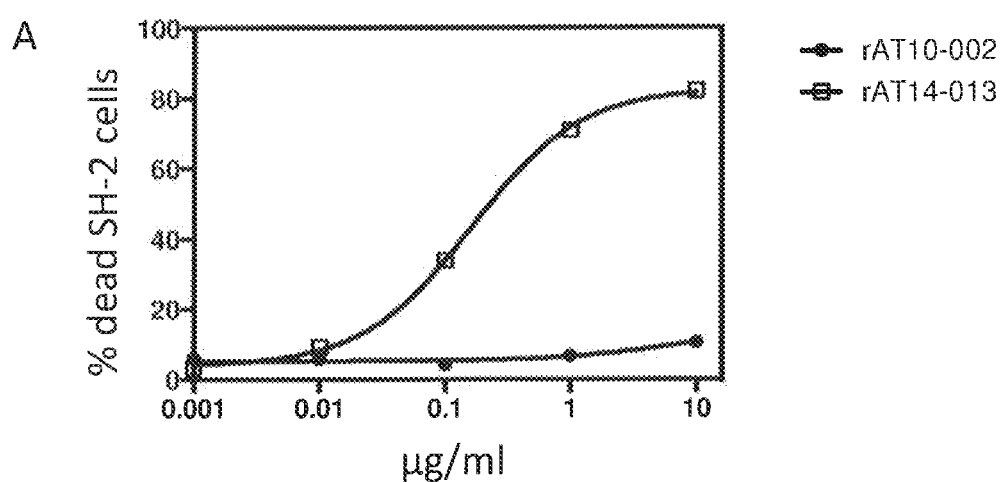
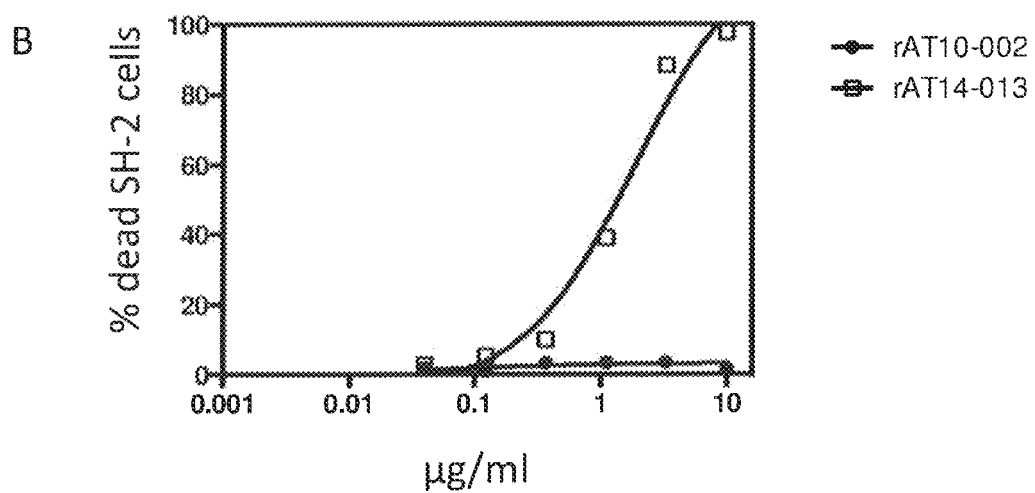

Figure 16
A
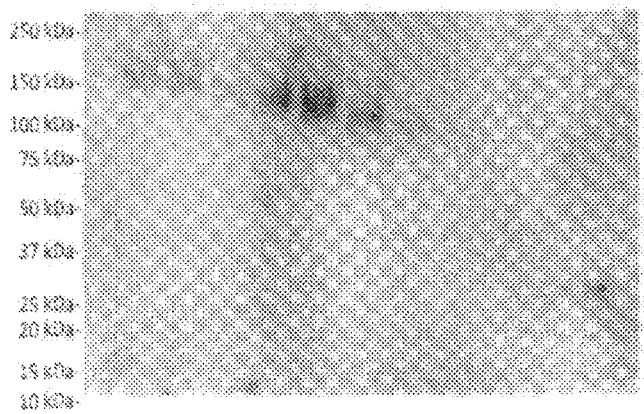
B
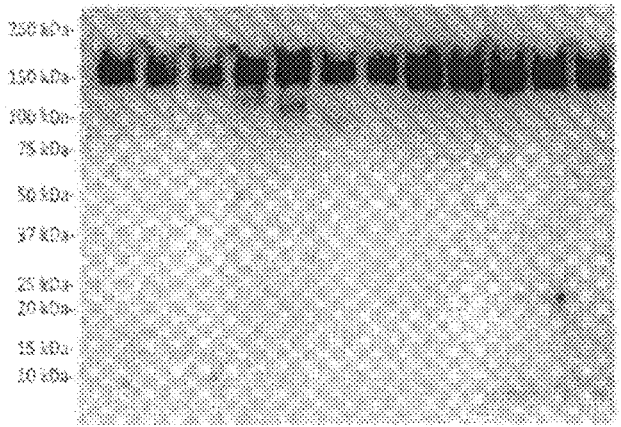

SEQUENCE LISTING

<160> NUMBER OF SEQ ID NOS: 37

<210> SEQ ID NO 1
<211> LENGTH: 52
<212> TYPE: PRT
<213> ORGANISM: Artificial Sequence
<220> FEATURE:
<223> OTHER INFORMATION: CD43 peptide

<400> SEQUENCE: 1

Gly Thr Ile Thr Thr Asn Ser Pro Glu Thr Ser Ser Arg Thr Ser Gly
1               5                   10                  15

Ala Pro Val Thr Thr Ala Ala Ser Ser Leu Glu Thr Ser Arg Gly Thr
            20                  25                  30

Ser Gly Pro Pro Leu Thr Met Ala Thr Val Ser Leu Glu Thr Ser Lys
        35                  40                  45

Gly Thr Ser Gly
    50

<210> SEQ ID NO 2
<211> LENGTH: 400
<212> TYPE: PRT
<213> ORGANISM: Homo sapiens
<220> FEATURE:
<221> NAME/KEY: SIGNAL
<222> LOCATION: (1)..(19)

<400> SEQUENCE: 2

Met Ala Thr Leu Leu Leu Leu Leu Gly Val Leu Val Val Ser Pro Asp
1               5                   10                  15

Ala Leu Gly Ser Thr Thr Ala Val Gln Thr Pro Thr Ser Gly Glu Pro
        20              25              30

Leu Val Ser Thr Ser Glu Pro Leu Ser Ser Lys Met Tyr Thr Thr Ser
        35              40              45

Ile Thr Ser Asp Pro Lys Ala Asp Ser Thr Gly Asp Gln Thr Ser Ala
50              55              60

Leu Pro Pro Ser Thr Ser Ile Asn Glu Gly Ser Pro Leu Trp Thr Ser
65              70              75              80

Ile Gly Ala Ser Thr Gly Ser Pro Leu Pro Glu Pro Thr Thr Tyr Gln
                85              90              95

Glu Val Ser Ile Lys Met Ser Ser Val Pro Gln Glu Thr Pro His Ala
            100             105             110

Thr Ser His Pro Ala Val Pro Ile Thr Ala Asn Ser Leu Gly Ser His
        115             120             125

Thr Val Thr Gly Gly Thr Ile Thr Thr Asn Ser Pro Glu Thr Ser Ser
130             135             140

Arg Thr Ser Gly Ala Pro Val Thr Thr Ala Ala Ser Ser Leu Glu Thr
145             150             155             160

Ser Arg Gly Thr Ser Gly Pro Pro Leu Thr Met Ala Thr Val Ser Leu
                165             170             175

Glu Thr Ser Lys Gly Thr Ser Gly Pro Pro Val Thr Met Ala Thr Asp
            180             185             190

Ser Leu Glu Thr Ser Thr Gly Thr Thr Gly Pro Pro Val Thr Met Thr
        195             200             205

Thr Gly Ser Leu Glu Pro Ser Ser Gly Ala Ser Gly Pro Gln Val Ser
210             215             220

Ser Val Lys Leu Ser Thr Met Met Ser Pro Thr Thr Ser Thr Asn Ala
225             230             235             240

Ser Thr Val Pro Phe Arg Asn Pro Asp Glu Asn Ser Arg Gly Met Leu
                245             250             255

Pro Val Ala Val Leu Val Ala Leu Leu Ala Val Ile Val Leu Val Ala
            260             265             270

Leu Leu Leu Leu Trp Arg Arg Arg Gln Lys Arg Arg Thr Gly Ala Leu
        275             280             285

Val Leu Ser Arg Gly Gly Lys Arg Asn Gly Val Val Asp Ala Trp Ala
290             295             300

Gly Pro Ala Gln Val Pro Glu Glu Gly Ala Val Thr Val Thr Val Gly
305             310             315             320

Gly Ser Gly Gly Asp Lys Gly Ser Gly Phe Pro Asp Gly Glu Gly Ser
                325             330             335

Ser Arg Arg Pro Thr Leu Thr Thr Phe Phe Gly Arg Arg Lys Ser Arg
            340             345             350

Gln Gly Ser Leu Ala Met Glu Glu Leu Lys Ser Gly Ser Gly Pro Ser
        355             360             365

Leu Lys Gly Glu Glu Glu Pro Leu Val Ala Ser Glu Asp Gly Ala Val
370             375             380

Asp Ala Pro Ala Pro Asp Glu Pro Glu Gly Gly Asp Gly Ala Ala Pro
385             390             395             400

<210> SEQ ID NO 3
<211> LENGTH: 33
<212> TYPE: PRT
<213> ORGANISM: Artificial Sequence
<220> FEATURE:
<223> OTHER INFORMATION: CD43 peptide

<400> SEQUENCE: 3

Gly Thr Ile Thr Thr Asn Ser Pro Glu Thr Ser Ser Arg Thr Ser Gly
1               5                   10                  15

Ala Pro Val Thr Thr Ala Ala Ser Ser Leu Glu Thr Ser Arg Gly Thr
            20                  25                  30

Ser

<210> SEQ ID NO 4
<211> LENGTH: 15
<212> TYPE: PRT
<213> ORGANISM: Artificial Sequence
<220> FEATURE:
<223> OTHER INFORMATION: CD43 peptide

<400> SEQUENCE: 4

Gly Thr Ile Thr Thr Asn Ser Pro Glu Thr Ser Ser Arg Thr Ser
1               5                   10                  15

<210> SEQ ID NO 5
<211> LENGTH: 22
<212> TYPE: PRT
<213> ORGANISM: Artificial Sequence
<220> FEATURE:
<223> OTHER INFORMATION: 3xFLAG

<400> SEQUENCE: 5

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 6
<211> LENGTH: 384
<212> TYPE: DNA
<213> ORGANISM: Artificial Sequence
<220> FEATURE:
<223> OTHER INFORMATION: AT14-013 (2K23-1K13) Heavy chain
<220> FEATURE:
<221> NAME/KEY: CDS
<222> LOCATION: (1)..(384)

<400> SEQUENCE: 6 cag ggg cga ctg cag gag tcg ggc cca gga ctg gtg aag cct tcg gag     48
Gln Gly Arg Leu Gln Glu Ser Gly Pro Gly Leu Val Lys Pro Ser Glu
1               5                   10                  15 acc ctg acc ctc acg tgc gct gtg tcc ggt ggc tcc tcc gtc agc agt     96
Thr Leu Thr Leu Thr Cys Ala Val Ser Gly Gly Ser Ser Val Ser Ser
            20                  25                  30 cct aac tgg tgg act tgg gtc cgc cag gcc ccc ggg aag ggg ctg gag    144
Pro Asn Trp Trp Thr Trp Val Arg Gln Ala Pro Gly Lys Gly Leu Glu
        35                  40                  45 tgg att gga gaa atc tat tat ggt ggg aga gtg agc tac aac tcg gcc    192
Trp Ile Gly Glu Ile Tyr Tyr Gly Gly Arg Val Ser Tyr Asn Ser Ala
    50                  55                  60 ctc agg agt cga gtc acc att tca tca gac agg tcc aaa gag gag ttc    240
Leu Arg Ser Arg Val Thr Ile Ser Ser Asp Arg Ser Lys Glu Glu Phe
65                  70                  75                  80 tcc ctg aaa ctg agg tct gtg acc gcc gcg gac acg gcc ata tat tat    288
Ser Leu Lys Leu Arg Ser Val Thr Ala Ala Asp Thr Ala Ile Tyr Tyr
                85                  90                  95 tgt gcg ggt caa aaa aat att ggc tgt ggt tac agc agt tgc ttt atc    336
Cys Ala Gly Gln Lys Asn Ile Gly Cys Gly Tyr Ser Ser Cys Phe Ile

```
             100                 105                 110
agt tgg ttc gac acc tgg gga cag gga att gcg gtc acc gtc tcc tca      384
Ser Trp Phe Asp Thr Trp Gly Gln Gly Ile Ala Val Thr Val Ser Ser
        115                 120                 125
```

<210> SEQ ID NO 7
<211> LENGTH: 128
<212> TYPE: PRT
<213> ORGANISM: Artificial Sequence
<220> FEATURE:
<223> OTHER INFORMATION: Synthetic Construct

<400> SEQUENCE: 7

```
Gln Gly Arg Leu Gln Glu Ser Gly Pro Gly Leu Val Lys Pro Ser Glu
1               5                   10                  15

Thr Leu Thr Leu Thr Cys Ala Val Ser Gly Gly Ser Ser Val Ser Ser
            20                  25                  30

Pro Asn Trp Trp Thr Trp Val Arg Gln Ala Pro Gly Lys Gly Leu Glu
        35                  40                  45

Trp Ile Gly Glu Ile Tyr Tyr Gly Gly Arg Val Ser Tyr Asn Ser Ala
    50                  55                  60

Leu Arg Ser Arg Val Thr Ile Ser Ser Asp Arg Ser Lys Glu Glu Phe
65                  70                  75                  80

Ser Leu Lys Leu Arg Ser Val Thr Ala Ala Asp Thr Ala Ile Tyr Tyr
                85                  90                  95

Cys Ala Gly Gln Lys Asn Ile Gly Cys Gly Tyr Ser Ser Cys Phe Ile
            100                 105                 110

Ser Trp Phe Asp Thr Trp Gly Gln Gly Ile Ala Val Thr Val Ser Ser
        115                 120                 125
```

<210> SEQ ID NO 8
<211> LENGTH: 93
<212> TYPE: DNA
<213> ORGANISM: Artificial Sequence
<220> FEATURE:
<223> OTHER INFORMATION: Heavy chain Fw1
<220> FEATURE:
<221> NAME/KEY: CDS
<222> LOCATION: (1)..(93)

<400> SEQUENCE: 8

```
cag ggg cga ctg cag gag tcg ggc cca gga ctg gtg aag cct tcg gag      48
Gln Gly Arg Leu Gln Glu Ser Gly Pro Gly Leu Val Lys Pro Ser Glu
1               5                   10                  15 acc ctg acc ctc acg tgc gct gtg tcc ggt ggc tcc tcc gtc agc          93
Thr Leu Thr Leu Thr Cys Ala Val Ser Gly Gly Ser Ser Val Ser
            20                  25                  30
```

<210> SEQ ID NO 9
<211> LENGTH: 31
<212> TYPE: PRT
<213> ORGANISM: Artificial Sequence
<220> FEATURE:
<223> OTHER INFORMATION: Synthetic Construct

<400> SEQUENCE: 9

```
Gln Gly Arg Leu Gln Glu Ser Gly Pro Gly Leu Val Lys Pro Ser Glu
1               5                   10                  15

Thr Leu Thr Leu Thr Cys Ala Val Ser Gly Gly Ser Ser Val Ser
            20                  25                  30
```

<210> SEQ ID NO 10

-continued

```
<211> LENGTH: 18
<212> TYPE: DNA
<213> ORGANISM: Artificial Sequence
<220> FEATURE:
<223> OTHER INFORMATION: Heavy chain  CDR1
<220> FEATURE:
<221> NAME/KEY: CDS
<222> LOCATION: (1)..(18)

<400> SEQUENCE: 10 agt cct aac tgg tgg act                                               18
Ser Pro Asn Trp Trp Thr
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic Construct

<400> SEQUENCE: 11

Ser Pro Asn Trp Trp Thr
1               5

<210> SEQ ID NO 12
<211> LENGTH: 42
<212> TYPE: DNA
<213> ORGANISM: Artificial Sequence
<220> FEATURE:
<223> OTHER INFORMATION: Heavy chainFW2
<220> FEATURE:
<221> NAME/KEY: CDS
<222> LOCATION: (1)..(42)

<400> SEQUENCE: 12 tgg gtc cgc cag gcc ccc ggg aag ggg ctg gag tgg att gga              42
Trp Val Arg Gln Ala Pro Gly Lys Gly Leu Glu Trp Ile Gly
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic Construct

<400> SEQUENCE: 13

Trp Val Arg Gln Ala Pro Gly Lys Gly Leu Glu Trp Ile Gly
1               5                   10

<210> SEQ ID NO 14
<211> LENGTH: 48
<212> TYPE: DNA
<213> ORGANISM: Artificial Sequence
<220> FEATURE:
<223> OTHER INFORMATION: Heavy chain CDR2
<220> FEATURE:
<221> NAME/KEY: CDS
<222> LOCATION: (1)..(48)

<400> SEQUENCE: 14 gaa atc tat tat ggt ggg aga gtg agc tac aac tcg gcc ctc agg agt      48
Glu Ile Tyr Tyr Gly Gly Arg Val Ser Tyr Asn Ser Ala Leu Arg Ser
1               5                   10                  15

<210> SEQ ID NO 15
<211> LENGTH: 16
<212> TYPE: PRT
```

<213> ORGANISM: Artificial Sequence
<220> FEATURE:
<223> OTHER INFORMATION: Synthetic Construct

<400> SEQUENCE: 15

Glu Ile Tyr Tyr Gly Gly Arg Val Ser Tyr Asn Ser Ala Leu Arg Ser
1               5                   10                  15

<210> SEQ ID NO 16
<211> LENGTH: 90
<212> TYPE: DNA
<213> ORGANISM: Artificial Sequence
<220> FEATURE:
<223> OTHER INFORMATION: Heavy chain) Fw3
<220> FEATURE:
<221> NAME/KEY: CDS
<222> LOCATION: (1)..(90)

<400> SEQUENCE: 16 cga gtc acc att tca tca gac agg tcc aaa gag gag ttc tcc ctg aaa    48
Arg Val Thr Ile Ser Ser Asp Arg Ser Lys Glu Glu Phe Ser Leu Lys
1               5                   10                  15 ctg agg tct gtg acc gcc gcg gac acg gcc ata tat tat tgt            90
Leu Arg Ser Val Thr Ala Ala Asp Thr Ala Ile Tyr Tyr Cys
            20                  25                  30

<210> SEQ ID NO 17
<211> LENGTH: 30
<212> TYPE: PRT
<213> ORGANISM: Artificial Sequence
<220> FEATURE:
<223> OTHER INFORMATION: Synthetic Construct

<400> SEQUENCE: 17

Arg Val Thr Ile Ser Ser Asp Arg Ser Lys Glu Glu Phe Ser Leu Lys
1               5                   10                  15

Leu Arg Ser Val Thr Ala Ala Asp Thr Ala Ile Tyr Tyr Cys
            20                  25                  30

<210> SEQ ID NO 18
<211> LENGTH: 60
<212> TYPE: DNA
<213> ORGANISM: Artificial Sequence
<220> FEATURE:
<223> OTHER INFORMATION: Heavy chain CDR3
<220> FEATURE:
<221> NAME/KEY: CDS
<222> LOCATION: (1)..(60)

<400> SEQUENCE: 18 gcg ggt caa aaa aat att ggc tgt ggt tac agc agt tgc ttt atc agt    48
Ala Gly Gln Lys Asn Ile Gly Cys Gly Tyr Ser Ser Cys Phe Ile Ser
1               5                   10                  15 tgg ttc gac acc                                                    60
Trp Phe Asp Thr
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic Construct

<400> SEQUENCE: 19

Ala Gly Gln Lys Asn Ile Gly Cys Gly Tyr Ser Ser Cys Phe Ile Ser
1               5                   10                  15

```
Trp Phe Asp Thr
            20

<210> SEQ ID NO 20
<211> LENGTH: 33
<212> TYPE: DNA
<213> ORGANISM: Artificial Sequence
<220> FEATURE:
<223> OTHER INFORMATION: Heavy chain Fw4
<220> FEATURE:
<221> NAME/KEY: CDS
<222> LOCATION: (1)..(33)

<400> SEQUENCE: 20 tgg gga cag gga att gcg gtc acc gtc tcc tca                           33
Trp Gly Gln Gly Ile Ala Val Thr Val Ser Ser
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic Construct

<400> SEQUENCE: 21

Trp Gly Gln Gly Ile Ala Val Thr Val Ser Ser
1               5                   10

<210> SEQ ID NO 22
<211> LENGTH: 339
<212> TYPE: DNA
<213> ORGANISM: Artificial Sequence
<220> FEATURE:
<223> OTHER INFORMATION: AT14-013 (2K23-1K13) Light chain
<220> FEATURE:
<221> NAME/KEY: CDS
<222> LOCATION: (1)..(339)

<400> SEQUENCE: 22 gac atc gtg atg acc cag tct cca gac tcc ctg gct gtg tct ctg ggc       48
Asp Ile Val Met Thr Gln Ser Pro Asp Ser Leu Ala Val Ser Leu Gly
1               5                   10                  15 gag agg gcc acc atc gcc tgc aag tcc agc cag act att tta caa agg       96
Glu Arg Ala Thr Ile Ala Cys Lys Ser Ser Gln Thr Ile Leu Gln Arg
            20                  25                  30 tcc aac cat ttg aac tac tta gct tgg tac cag cag aaa cca gga cag      144
Ser Asn His Leu Asn Tyr Leu Ala Trp Tyr Gln Gln Lys Pro Gly Gln
        35                  40                  45 cct cct aaa gtg ctc att tat tgg gca tct acc cgg gaa tcc ggg gtc      192
Pro Pro Lys Val Leu Ile Tyr Trp Ala Ser Thr Arg Glu Ser Gly Val
    50                  55                  60 cct gac cga ttc agt ggc agc ggg tct ggg aca gat ttc act ctc acc      240
Pro Asp Arg Phe Ser Gly Ser Gly Ser Gly Thr Asp Phe Thr Leu Thr
65                  70                  75                  80 atc aac agc ctg cag gct gag gat gtg gca gtt tat tac tgt cac caa      288
Ile Asn Ser Leu Gln Ala Glu Asp Val Ala Val Tyr Tyr Cys His Gln
                85                  90                  95 tat tat act act ccg cag act ttt ggc cag ggg acc aag gtg gag atc      336
Tyr Tyr Thr Thr Pro Gln Thr Phe Gly Gln Gly Thr Lys Val Glu Ile
            100                 105                 110 aaa                                                                   339
Lys
```

```
<210> SEQ ID NO 23
<211> LENGTH: 113
<212> TYPE: PRT
<213> ORGANISM: Artificial Sequence
<220> FEATURE:
<223> OTHER INFORMATION: Synthetic Construct

<400> SEQUENCE: 23

Asp Ile Val Met Thr Gln Ser Pro Asp Ser Leu Ala Val Ser Leu Gly
1               5                   10                  15

Glu Arg Ala Thr Ile Ala Cys Lys Ser Ser Gln Thr Ile Leu Gln Arg
            20                  25                  30

Ser Asn His Leu Asn Tyr Leu Ala Trp Tyr Gln Gln Lys Pro Gly Gln
        35                  40                  45

Pro Pro Lys Val Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys His Gln
                85                  90                  95

Tyr Tyr Thr Thr Pro Gln Thr Phe Gly Gln Gly Thr Lys Val Glu Ile
            100                 105                 110

Lys

<210> SEQ ID NO 24
<211> LENGTH: 69
<212> TYPE: DNA
<213> ORGANISM: Artificial Sequence
<220> FEATURE:
<223> OTHER INFORMATION: Light chain Fw1
<220> FEATURE:
<221> NAME/KEY: CDS
<222> LOCATION: (1)..(69)

<400> SEQUENCE: 24 gac atc gtg atg acc cag tct cca gac tcc ctg gct gtg tct ctg ggc    48
Asp Ile Val Met Thr Gln Ser Pro Asp Ser Leu Ala Val Ser Leu Gly
1               5                   10                  15 gag agg gcc acc atc gcc tgc                                         69
Glu Arg Ala Thr Ile Ala Cys
            20

<210> SEQ ID NO 25
<211> LENGTH: 23
<212> TYPE: PRT
<213> ORGANISM: Artificial Sequence
<220> FEATURE:
<223> OTHER INFORMATION: Synthetic Construct

<400> SEQUENCE: 25

Asp Ile Val Met Thr Gln Ser Pro Asp Ser Leu Ala Val Ser Leu Gly
1               5                   10                  15

Glu Arg Ala Thr Ile Ala Cys
            20

<210> SEQ ID NO 26
<211> LENGTH: 51
<212> TYPE: DNA
<213> ORGANISM: Artificial Sequence
<220> FEATURE:
<223> OTHER INFORMATION: Light chain CDR1
<220> FEATURE:
<221> NAME/KEY: CDS
<222> LOCATION: (1)..(51)
```

<400> SEQUENCE: 26

```
aag tcc agc cag act att tta caa agg tcc aac cat ttg aac tac tta        48
Lys Ser Ser Gln Thr Ile Leu Gln Arg Ser Asn His Leu Asn Tyr Leu
1               5                   10                  15 gct                                                                     51
Ala
```

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

```
Lys Ser Ser Gln Thr Ile Leu Gln Arg Ser Asn His Leu Asn Tyr Leu
1               5                   10                  15

Ala
```

<210> SEQ ID NO 28
<211> LENGTH: 45
<212> TYPE: DNA
<213> ORGANISM: Artificial Sequence
<220> FEATURE:
<223> OTHER INFORMATION: Light chain Fw2
<220> FEATURE:
<221> NAME/KEY: CDS
<222> LOCATION: (1)..(45)

<400> SEQUENCE: 28

```
tgg tac cag cag aaa cca gga cag cct cct aaa gtg ctc att tat           45
Trp Tyr Gln Gln Lys Pro Gly Gln Pro Pro Lys Val Leu Ile Tyr
1               5                   10                  15
```

<210> SEQ ID NO 29
<211> LENGTH: 15
<212> TYPE: PRT
<213> ORGANISM: Artificial Sequence
<220> FEATURE:
<223> OTHER INFORMATION: Synthetic Construct

<400> SEQUENCE: 29

```
Trp Tyr Gln Gln Lys Pro Gly Gln Pro Pro Lys Val Leu Ile Tyr
1               5                   10                  15
```

<210> SEQ ID NO 30
<211> LENGTH: 21
<212> TYPE: DNA
<213> ORGANISM: Artificial Sequence
<220> FEATURE:
<223> OTHER INFORMATION: Light chain CDR2
<220> FEATURE:
<221> NAME/KEY: CDS
<222> LOCATION: (1)..(21)

<400> SEQUENCE: 30

```
tgg gca tct acc cgg gaa tcc                                            21
Trp Ala Ser Thr Arg Glu Ser
1               5
```

<210> SEQ ID NO 31
<211> LENGTH: 7
<212> TYPE: PRT
<213> ORGANISM: Artificial Sequence
<220> FEATURE:
<223> OTHER INFORMATION: Synthetic Construct

<400> SEQUENCE: 31

Trp Ala Ser Thr Arg Glu Ser
1               5

<210> SEQ ID NO 32
<211> LENGTH: 96
<212> TYPE: DNA
<213> ORGANISM: Artificial Sequence
<220> FEATURE:
<223> OTHER INFORMATION: Light chain Fw3
<220> FEATURE:
<221> NAME/KEY: CDS
<222> LOCATION: (1)..(96)

<400> SEQUENCE: 32

```
ggg gtc cct gac cga ttc agt ggc agc ggg tct ggg aca gat ttc act    48
Gly Val Pro Asp Arg Phe Ser Gly Ser Gly Ser Gly Thr Asp Phe Thr
1               5                   10                  15 ctc acc atc aac agc ctg cag gct gag gat gtg gca gtt tat tac tgt    96
Leu Thr Ile Asn Ser Leu Gln Ala Glu Asp Val Ala Val Tyr Tyr Cys
            20                  25                  30
```

<210> SEQ ID NO 33
<211> LENGTH: 32
<212> TYPE: PRT
<213> ORGANISM: Artificial Sequence
<220> FEATURE:
<223> OTHER INFORMATION: Synthetic Construct

<400> SEQUENCE: 33

Gly Val Pro Asp Arg Phe Ser Gly Ser Gly Ser Gly Thr Asp Phe Thr
1               5                   10                  15

Leu Thr Ile Asn Ser Leu Gln Ala Glu Asp Val Ala Val Tyr Tyr Cys
            20                  25                  30

<210> SEQ ID NO 34
<211> LENGTH: 27
<212> TYPE: DNA
<213> ORGANISM: Artificial Sequence
<220> FEATURE:
<223> OTHER INFORMATION: Light chain CDR3
<220> FEATURE:
<221> NAME/KEY: CDS
<222> LOCATION: (1)..(27)

<400> SEQUENCE: 34

```
cac caa tat tat act act ccg cag act                                27
His Gln Tyr Tyr Thr Thr Pro Gln Thr
1               5
```

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

His Gln Tyr Tyr Thr Thr Pro Gln Thr
1               5

<210> SEQ ID NO 36
<211> LENGTH: 30
<212> TYPE: DNA
<213> ORGANISM: Artificial Sequence
<220> FEATURE:

```
<223> OTHER INFORMATION: Light chain Fw4
<220> FEATURE:
<221> NAME/KEY: CDS
<222> LOCATION: (1)..(30)

<400> SEQUENCE: 36 ttt ggc cag ggg acc aag gtg gag atc aaa                              30
Phe Gly Gln Gly Thr Lys Val Glu Ile Lys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Phe Gly Gln Gly Thr Lys Val Glu Ile Lys
1               5                   10
```

AML ANTIGENS AND USES THEREOF

CROSS REFERENCE TO RELATED APPLICATIONS

This application claims priority and the benefit of PCT/NL2016/050449, filed Jun. 24, 2016, which claims priority and the benefit of EP 16150621.7, filed Jan. 8, 2016, which claims priority and the benefit of EP 15173662.6, filed Jun. 24, 2015, the entire contents of each of which are hereby incorporated in total by reference.

SEQUENCE LISTING

This application incorporates by reference the Sequence Listing contained in an ASCII text file named "362346_00048_Sequence.txt" submitted via EFS-Web. The text file was created on Dec. 8, 2017 and is 22 kb in size.

The invention relates to the fields of biology, immunology and medicine.

Acute myeloid leukemia (AML) is a high risk malignancy with five year survival rates of 40-50% in patients younger than 60 years of age. For patients over 65 years of age outcomes are even worse, with only less than 20% of patients obtaining durable remissions. Allogeneic stem cell transplantation is frequently applied in the treatment of acute leukemia. It was initially designed to rescue patients from otherwise lethal myeloablative chemotherapy but was subsequently found to be complicated by alloreactive immune response related complications (graft versus host disease; GvHD). T cell depletion of grafts before reinfusion averted GvHD but the observation that T cell depleted graft recipients, similar to monozygotic twin donor transplant recipients, experienced much higher rates of relapse made it increasingly clear that the success of allogeneic SCT is dependent on the induction of an anti-leukemic immune response (graft versus leukemia (GvL)). This has led to the development of strategies to apply allogeneic stem cell transplantation without myeloablative conditioning (reduced intensity stem cell transplantation, RIST), to reduce cytotoxicity and to allow allogeneic SCT in a larger group of patients including older patients and heavily pretreated patients. Preparative regimens in RIST are aimed at decimating the recipients adaptive immune system to prevent graft rejection, without complete ablation of the recipients bone marrow thereby reducing early SCT toxicity. Following transplantation, donor stem cells gradually replace stem cells of the recipient and full donor chimerism is usually achieved within three months after SCT. Although allogeneic SCT is curative in significant numbers of patients, and much progress has been made in the supportive care of SCT recipients, still 15-30% of patients die as a result of transplantation related complications such as GvHD and infectious complications (arising as a result of slow immune recovery following SCT or as a complication of immunosuppressive therapy of GvHD). Hence, although SCT is potentially curative when potent graft versus leukemia (GvL) responses are induced, its therapeutic success is limited by anti-host immune responses leading to GvHD which causes high morbidity and mortality. In view of the high GvHD incidence after allogeneic stem cell transplantation, resulting in death of 15-30% of the patients, as well as the fact that a suitable donor is not always available for a given patient, alternative treatment approaches would be advantageous. International patent application PCT/NL2014/050873 provides patient-derived, AML-specific, human antibodies that are able to bind intact AML cells. Importantly, the antibodies are derived from human AML patients that received an allogeneic SCT and are in complete remission, demonstrating that the antibodies are effective against AML. The use of antibodies as disclosed in PCT/NL2014/050873 in AML therapy is, therefore, preferred.

Instead of passive immunization with antibodies, immunotherapy would also be an attractive approach. With immunotherapy, a patient suffering from a disease is provided with a disease-specific antigen, which induces and/or enhances an immune response in said patient against the disease. Prophylactic or semi-prophylactic applications, wherein an individual is provided with a disease-specific antigen in order to elicit an immune response before onset or before (further) progression of disease, would also be attractive. For instance, immunization with an AML-specific target molecule in order to elicit an immune response against AML would be particularly attractive for patients that received an allogeneic hematopoietic stem cell transplantation. Another group for which immunization with such target would be attractive is patients suffering from intermediate to high risk myelodysplastic syndrome (MDS). Such patients have an intermediate to high risk to develop AML, so that it is advantageous to elicit an anti-AML immune response beforehand. The risk of an MDS patient to develop AML is typically established according to the international prognostic scoring system (IPSS; see for instance Malcovati et al. 2013). Non-limiting examples of intermediate to high risk MDS patients are MDS-RAEB-1 and MDS-RAEB-2 patients.

Immunotherapy and vaccinations that are specifically directed against AML are currently not available, due to the lack of suitable AML-specific antigens.

AML-specific antigens would also be particularly suitable for determining whether a sample of a patient contains antibodies and/or immune cells able to specifically bind AML cells. Such information would for instance be valuable for AML diagnosis or for monitoring AML therapy.

It is an object of the present invention to provide novel peptides and compounds comprising an antigen of AML cells. Preferably, peptides and compounds are provided that are able to detect and/or elicit an immune response, preferably a specific immune response, against myeloproliferative disorders, more preferably AML.

The invention provides an isolated, recombinant or purified CD43 peptide with a length of at most 100 amino acid residues, wherein said peptide comprises an amino acid sequence with a length of at least 3 amino acid residues and at most 51 amino acid residues that is identical to a sequence located between CD43 amino acid positions 133 and 184 as depicted FIG. 13. Said peptide preferably comprises an amino acid sequence with a length of at least 3 amino acid residues and at most 51 amino acid residues that is identical to a sequence located between CD43 amino acid positions 133 and 183 as depicted FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or at least 15 amino acid residues, or at least 20 amino acid residues, or at least 25 amino acid residues, or at least 30 amino acid residues, or at least 35 amino acid residues, or at least 40 amino acid residues, or at least 45 amino acid residues, or at least 50 amino acid residues, or 51 amino acid residues.

Some embodiments provide an isolated, recombinant or purified CD43 peptide with a length of at most 100 amino acid residues, wherein said peptide comprises an amino acid sequence with a length of at least 3 amino acid residues and at most 33 amino acid residues that is identical to a sequence located between CD43 amino acid positions 133 and 165 as depicted FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or at least 15 amino acid residues, or at least 20 amino acid residues, or at least 25 amino acid residues, or at least 30 amino acid residues, or 33 amino acid residues.

Some embodiments provide an isolated, recombinant or purified CD43 peptide with a length of at most 100 amino acid residues, wherein said peptide comprises an amino acid sequence with a length of at least 3 amino acid residues and at most 15 amino acid residues that is identical to a sequence located between CD43 amino acid positions 133 and 147 as depicted FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or 15 amino acid residues.

The present inventors have surprisingly discovered that a specific immune response against AML can be detected and/or elicited using a CD43 peptide according to the present invention. This finding was unexpected, because CD43 is present on the surface of most kinds of (non-malignant) leukocytes, as well as on many non-hematopoietic tumor cells like for instance human colon cancer cells, human uterine cervix cancer cells, human lung cancer cells and human breast adenocarcinoma cells. In view of this abundant presence of CD43, before the present invention CD43 was not considered an appropriate compound for providing AML specificity. Yet, as shown in the Examples, the AML-specific antibody AT14-013 binds a CD43 peptide according to the present invention. Moreover, antibody AT14-013 binds to various different CD43+ AML cells (FIGS. 2 and 3), but not to CD43+ PBMCs, activated and non-activated T cells, B cells, non-activated monocytes, thymocytes, ALL cells, colon carcinoma cells, non-malignant colon cells, Jurkat cells, Ramos cells or normal bone marrow cells (shown in FIG. 5). Hence, antibody AT14-013, that is specifically directed against a CD43 peptide as defined in the claims, binds CD43+ AML cells, whereas it does not bind various other kinds of CD43+ cells. Interestingly, antibody AT14-013 does not bind different kinds of non-AML, CD43+ hematopoietic stem cells or more mature cells of the lymphoid lineages. It is also shown in the Examples that antibody AT14-013 is able to bind fetal hematopoietic stem cells, from which it is concluded that the CD43 epitope that is recognized by AT14-013 is an oncofetal epitope. Antibody AT14-013 is also able to bind autologous leukemic stem cells. Moreover, antibody AT14-013 is able to counteract AML growth in vivo. The present invention thus provides a CD43 antigen of AML cells.

CD43, which is also referred to as leukosialin, sialophorin, galactoglycoprotein, leukocyte sialoglycoprotein or gp115, is a glycosylated mucin-like type I transmembrane protein that is present on the surface of most hematopoietic cells, except erythrocytes. CD43, encoded by one exon, plays a role in cell-cell interactions. It has a highly glycosylated extracellular region of 235 amino acids. Two CD43 glycoforms have been described, wherein one glycoform mainly contains tetrasaccharides and the other glycoform possesses mainly branched hexasaccharides. Both glycoforms can be expressed on the surface of one cell. CD43 is for instance described in Shelley et al. (1989) and Schmid et al. (1992). The sequence of human CD43, depicted in FIG. 13 is present in the Genbank CCDS database under accession No. CCDS10650.1.

As used herein, the term "CD43 peptide according to the invention" refers to a chain of amino acids with a length of at most 100 amino acid residues, wherein said amino acid chain comprises a sequence with a length of at least 3 amino acids residues and at most 51 amino acid residues that is identical to a sequence located between amino acid positions 133 and 184 of a human CD43 protein as depicted in FIG. 13, or wherein said amino acid chain comprises a sequence with a length of at least 3 amino acids residues and at most 51 amino acid residues that is identical to a sequence located between amino acid positions 133 and 183 of a human CD43 protein as depicted in FIG. 13, or wherein said amino acid chain comprises a sequence with a length of at least 3 amino acids residues and at most 33 amino acid residues that is identical to a sequence located between amino acid positions 133 and 165 of a human CD43 protein as depicted in FIG. 13, or wherein said amino acid chain comprises a sequence with a length of at least 3 amino acids residues and at most 15 amino acid residues that is identical to a sequence located between amino acid positions 133 and 147 of a human CD43 protein as depicted in FIG. 13.

As explained in detail in the examples, the present invention provides the insight that the amino acid sequence between positions 133 and 184 of a human CD43 protein comprises an AML epitope that is specifically bound by antibody AT14-013. Said AML epitope comprises one or more amino acid residues that are present between amino acid sequence positions 133 and 165 as depicted in FIG. 13. Said AML epitope, which is present on different AML cell lines and AML blasts, and which is not present or exposed on many other CD43+ cells, is therefore particularly suitable for eliciting or detecting an AML-specific immune response. In some embodiments, a CD43 peptide according to the invention comprises the amino acid sequence GTITTNSPETSSRTS. In some embodiments, a CD43 peptide according to the invention comprises the amino acid sequence GTITTNSPETSSRTSGAPVTTAASSLETSRGTS.

In some embodiments, a CD43 peptide according to the invention comprises the amino acid sequence GTITTNSPETSSRTSGAPVTTAASSLETSRGTSGPPLTMATVSLETSKGTSG.

In some embodiments, a CD43 peptide according to the present invention has a length of at most 90 amino acid residues. In some embodiments, a CD43 peptide according to the present invention has a length of at most 85 amino acid residues or at most 75 amino acid residues or at most 70 amino acid residues. In some embodiments, a CD43 peptide according to the present invention has a length of at most 65 amino acid residues or at most 60 amino acid residues or at most 55 amino acid residues or at most 50 amino acid residues or at most 45 amino acid residues or at most 40 amino acid residues or at most 35 amino acid residues. In some embodiments, said CD43 peptide according to the present invention has a length of at most 52 amino acid residues, or at most 51 amino acid residues, or at most 33 amino acid residues, or at most 30 amino acid residues or at most 25 amino acid residues or at most 20 amino acid residues or at most 15 amino acid residues. In some embodiments, a CD43 peptide according to the present invention has a length of at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or at least 15 amino acid residues.

In some embodiments, said CD43 peptide according to the invention has a length of at least 52 amino acid residues or at least 51 amino acid residues, wherein said peptide comprises an amino acid sequence that is identical to a sequence located between amino acid positions 133 and 184 of a human CD43 protein as depicted in FIG. 13. In some embodiments, said CD43 peptide according to the invention has a length of at least 51 amino acid residues, wherein said amino acid residues are identical to the amino acids between amino acid positions 133-183 of a human CD43 protein as depicted in FIG. 13.

In some embodiments, a CD43 peptide according to the invention has a length of at least 33 amino acid residues and comprises an amino acid sequence that is identical to the sequence located between amino acid positions 133 and 165 of the human CD43 protein as depicted in FIG. 13.

In some embodiments, a CD43 peptide according to the invention has a length of at least 15 amino acid residues and comprises an amino acid sequence that is identical to the sequence located between amino acid positions 133 and 147 of the human CD43 protein as depicted in FIG. 13.

In some embodiments, a CD43 peptide according to the invention consists of the sequence GTITTNSPETSSRTSGAPVTTAASSLETSRGTSGPPLTMATVSLETSKGTSG.

In some embodiments, a CD43 peptide according to the invention consists of the sequence GTITTNSPETSSRTSGAPVTTAASSLETSRGTS.

In some embodiments, a CD43 peptide according to the invention consists of the sequence GTITTNSPETSSRTS.

As used herein, the expressions "sequence located between CD43 amino acid positions X and Y as depicted in FIG. 13", "sequence located between amino acid positions X and Y of the human CD43 protein as depicted in FIG. 13", "wherein said amino acid residues are identical to the amino acids between amino acid positions X-Y of a human CD43 protein as depicted in FIG. 13" and "an amino acid sequence that is identical to the sequence located between amino acid positions X and Y of the human CD43 protein as depicted in FIG. 13" encompass sequences that are located between the recited positions and that include the amino acid(s) of position X and/or Y. In addition, the terms embrace sequences that are located between the recited positions and that do not contain the amino acid(s) of positions X and/or Y. In other words, in some embodiments the amino acid(s) of the recited positions X and/or Y are present in a CD43 peptide according to the invention, whereas in other embodiments the amino acids of the recited positions X and/or Y are absent.

Besides the recited amino acid sequences that are identical to a sequence located between amino acid positions 133 and 184, or to a sequence located between amino acid positions 133 and 183, or to a sequence located between amino acid positions 133 and 165, or to a sequence located between amino acid positions 133 and 147, of a human CD43 protein as depicted in FIG. 13, a CD43 peptide according to the present invention may further comprise other amino acid residues. In some embodiments, said other amino acid residues are not derived from a CD43 sequence. Said other amino acid residues, which are also referred to herein as "non-CD43 amino acid residues" may for instance function to enhance stability, and/or to enhance immunogenicity, and/or to couple the CD43 peptide to another moiety such as for instance a molecular scaffold or carrier. Non-limiting examples of such scaffold or carriers are keyhole limpet hemocyanin and CLIPS scaffolds (such as for instance bis(bromomethyl)benzene, tris(bromomethyl)benzene and tetra(bromomethyl)benzene, described in WO 2004/077062). Some embodiments therefore provide an isolated, recombinant or purified peptide with a length of at most 100 amino acid residues, wherein said peptide comprises an amino acid sequence with a length of at least 3 amino acid residues and at most 52 amino acid residues, or at most 51 amino acid residues, that is identical to a sequence located between CD43 amino acid positions 133 and 184 as depicted FIG. 13, and wherein said peptide also comprises at least 1, or at least 2, or at least 3, or at least 4, or at least 5, or at least 10, or at least 20, or at least 30, or at least 40, or at least 50, or at least 60, or at least 70, or at least 80, non-CD43 amino acid residues, wherein the full length sequence of said non-CD43 amino acid residues is not present in human CD43 as depicted in FIG. 13.

Some embodiments provide an isolated, recombinant or purified peptide with a length of at most 100 amino acid residues, wherein said peptide comprises an amino acid sequence with a length of at least 3 amino acid residues and at most 51 amino acid residues that is identical to a sequence located between CD43 amino acid positions 133 and 183 as depicted FIG. 13, and wherein said peptide also comprises at least 1, or at least 2, or at least 3, or at least 4, or at least 5, or at least 10, or at least 20, or at least 30, or at least 40, or at least 50, or at least 60, or at least 70, or at least 80, non-CD43 amino acid residues, wherein the full length sequence of said non-CD43 amino acid residues is not present in human CD43 as depicted in FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or at least 15 amino acid residues, or at least 20 amino acid residues, or at least 25 amino acid residues or at least 30 amino acid residues or at least 35 amino acid residues or at least 40 amino acid residues, or at least 45 amino acid residues, or at least 50 amino acid residues, or 51 amino acid residues.

Some embodiments provide an isolated, recombinant or purified peptide with a length of at most 100 amino acid residues, wherein said peptide comprises an amino acid sequence with a length of at least 3 amino acid residues and at most 33 amino acid residues that is identical to a sequence located between CD43 amino acid positions 133 and 165 as depicted FIG. 13, and wherein said peptide also comprises at least 1, or at least 2, or at least 3, or at least 4, or at least 5, or at least 10, or at least 20, or at least 30, or at least 40, or at least 50, or at least 60, or at least 70, or at least 80, non-CD43 amino acid residues, wherein the full length sequence of said non-CD43 amino acid residues is not present in human CD43 as depicted in FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or at least 15 amino acid residues, or at least 20 amino acid residues, or at least 25 amino acid residues or at least 30 amino acid residues or 33 amino acid residues.

Some embodiments provide an isolated, recombinant or purified peptide with a length of at most 100 amino acid residues, wherein said peptide comprises an amino acid sequence with a length of at least 3 amino acid residues and at most 15 amino acid residues that is identical to a sequence located between CD43 amino acid positions 133 and 147 as depicted FIG. 13, and wherein said peptide also comprises at least 1, or at least 2, or at least 3, or at least 4, or at least 5, or at least 10, or at least 20, or at least 30, or at least 40, or at least 50, or at least 60, or at least 70, or at least 80, non-CD43 amino acid residues, wherein the full length sequence of said non-CD43 amino acid residues is not present in human CD43 as depicted in FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or 15 amino acid residues.

The above mentioned peptides are also embraced by the term "CD43 peptide according to the present invention".

Some embodiments provide a compound comprising a CD43 peptide according to the present invention. Some embodiments provide an immunogenic compound comprising a CD43 peptide according to the present invention. In some embodiments said CD43 peptide is coupled to a pharmaceutically acceptable carrier or scaffold.

In some embodiments, a CD43 peptide according to the invention is a truncated CD43 molecule with a length of at most 100 amino acid residues. Preferably, said truncated CD43 molecule is devoid of the intracellular region of a wild type human CD43. In preferred embodiments, said truncated CD43 molecule is devoid of both the intracellular region and the transmembrane region of a wild type human CD43. In further preferred embodiments, said CD43 peptide according to the invention is a truncated CD43 extracellular region with a length of at most 90 amino acid residues, or at most 80 amino acid residues, or at most 70 amino acid residues, or at most 60 amino acid residues, or at most 52 amino acid residues, or at most 51 amino acid residues, or at most 50 amino acid residues, or at most 45 amino acid residues, or at most 40 amino acid residues, or at most 35 amino acid residues, or at most 33 amino acid residues, or at most 30 amino acid residues, or at most 25 amino acid residues, or at most 20 amino acid residues, that comprises an amino acid sequence with a length of at least 3 amino acid residues and at most 52 amino acid residues or at most 51 amino acid residues that is identical to a sequence located between CD43 amino acid positions 133 and 184 as depicted FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or at least 15 amino acid residues, or at least 20 amino acid residues, or at least 25 amino acid residues or at least 30 amino acid residues or at least 35 amino acid residues or at least 40 amino acid residues, or at least 45 amino acid residues, or at least 50 amino acid residues, or 51 amino acid residues.

In some embodiments, said CD43 peptide according to the invention is a truncated CD43 extracellular region with a length of at most 90 amino acid residues, or at most 80 amino acid residues, or at most 70 amino acid residues, or at most 60 amino acid residues, or at most 51 amino acid residues, or at most 50 amino acid residues, or at most 45 amino acid residues, or at most 40 amino acid residues, or at most 35 amino acid residues, or at most 33 amino acid residues, or at most 30 amino acid residues, or at most 25 amino acid residues, or at most 20 amino acid residues, that comprises an amino acid sequence with a length of at least 3 amino acid residues and at most 51 amino acid residues that is identical to a sequence located between CD43 amino acid positions 133 and 183 as depicted FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or at least 15 amino acid residues, or at least 20 amino acid residues, or at least 25 amino acid residues or at least 30 amino acid residues or at least 35 amino acid residues or at least 40 amino acid residues, or at least 45 amino acid residues, or at least 50 amino acid residues, or 51 amino acid residues.

In some embodiments, said CD43 peptide according to the invention is a truncated CD43 extracellular region with a length of at most 90 amino acid residues, or at most 80 amino acid residues, or at most 70 amino acid residues, or at most 60 amino acid residues, or at most 51 amino acid residues, or at most 50 amino acid residues, or at most 45 amino acid residues, or at most 40 amino acid residues, or at most 35 amino acid residues, or at most 33 amino acid residues, or at most 30 amino acid residues, or at most 25 amino acid residues, or at most 20 amino acid residues, that comprises an amino acid sequence with a length of at least 3 amino acid residues and at most 33 amino acid residues that is identical to a sequence located between CD43 amino acid positions 133 and 165 as depicted FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or at least 15 amino acid residues, or at least 20 amino acid residues, or at least 25 amino acid residues or at least 30 amino acid residues or 33 amino acid residues.

In some embodiments, said CD43 peptide according to the invention is a truncated CD43 extracellular region with a length of at most 90 amino acid residues, or at most 80 amino acid residues, or at most 70 amino acid residues, or at most 60 amino acid residues, or at most 51 amino acid residues, or at most 50 amino acid residues, or at most 45 amino acid residues, or at most 40 amino acid residues, or at most 35 amino acid residues, or at most 33 amino acid residues, or at most 30 amino acid residues, or at most 25 amino acid residues, or at most 20 amino acid residues, that comprises an amino acid sequence with a length of at least 3 amino acid residues and at most 15 amino acid residues that is identical to a sequence located between CD43 amino acid positions 133 and 147 as depicted FIG. 13. In some embodiments, the length of said amino acid sequence is at least 5 amino acid residues, or at least 8 amino acid residues, or at least 10 amino acid residues, or at least 11 amino acid residues, or at least 12 amino acid residues, or at least 13 amino acid residues, or at least 14 amino acid residues, or 15 amino acid residues.

Some embodiments provide a CD43 peptide according to the invention that is a truncated CD43 extracellular region with a length of at most 90 amino acid residues, or at most 80 amino acid residues, or at most 70 amino acid residues, or at most 60 amino acid residues, or at most 52 amino acid residues, or at most 51 amino acid residues, or at most 50 amino acid residues, or at most 45 amino acid residues, or at most 40 amino acid residues, or at most 35 amino acid residues, or at most 33 amino acid residues, or at most 30 amino acid residues, or at most 25 amino acid residues, or at most 20 amino acid residues, or at most 15 amino acid residues.

As is known to the skilled person, once an immunogenic sequence has been provided, it has become possible to alter the sequence to some extent, thereby preferably optimizing the immunogenicity and/or stability of the resulting immunogen. This is for instance done by mutagenesis procedures where after the stability and/or immunogenicity of the resulting compounds are preferably tested and an improved AML-specific antigenic compound is selected. A skilled person is well capable of generating antigen variants starting from a certain amino acid sequence. For instance, conservative amino acid substitution is applied. Examples of conservative amino acid substitution include the substitution of one hydrophobic residue such as isoleucine, valine, leucine or methionine for another hydrophobic residue, and the substitution of one polar residue for another polar residue, such as the substitution of arginine for lysine, glutamic acid for asp artic acid, or glutamine for asparagine. In some embodiments, a replacement net analysis is carried out, which involves replacement of one or more amino acid residues by any other amino acid residue, and testing the resulting compounds.

Some embodiments therefore provide an isolated, recombinant or purified CD43 peptide with a length of at most 100 amino acid residues that comprises, or essentially consists of, an amino acid sequence having a length of at least 3 amino acid residues and at most 52 amino acid residues or at most 51 amino acid residues, that has at least 80%, more preferably at least 85%, more preferably at least 90%, more preferably at least 95%, more preferably at least 96%, more preferably at least 97%, more preferably at least 98%, more preferably at least 99% sequence identity with a sequence located between amino acid positions 133 and 184 of the human CD43 protein as depicted in FIG. 13. Some embodiments provide an isolated, recombinant or purified CD43 peptide that comprises an amino acid sequence having a length of 51 amino acid residues, that has at least 80%, more preferably at least 85%, more preferably at least 90%, more preferably at least 95%, more preferably at least 96%, more preferably at least 97%, more preferably at least 98%, more preferably at least 99% sequence identity with the sequence located between amino acid positions 133 and 183 of the human CD43 protein as depicted in FIG. 13.

Some embodiments provide an isolated, recombinant or purified CD43 peptide with a length of at most 100 amino acid residues that comprises, or essentially consists of, an amino acid sequence having a length of 33 amino acid residues, that has at least 80%, more preferably at least 85%, more preferably at least 90%, more preferably at least 95%, more preferably at least 96%, more preferably at least 97%, more preferably at least 98%, more preferably at least 99% sequence identity with the sequence located between amino acid positions 133 and 165 of the human CD43 protein as depicted in FIG. 13.

Some embodiments provide an isolated, recombinant or purified CD43 peptide with a length of at most 100 amino acid residues that comprises, or essentially consists of, an amino acid sequence having a length of 15 amino acid residues, that has at least 80%, more preferably at least 85%, more preferably at least 90%, more preferably at least 95%, more preferably at least 96%, more preferably at least 97%, more preferably at least 98%, more preferably at least 99% sequence identity with the sequence located between amino acid positions 133 and 147 of the human CD43 protein as depicted in FIG. 13.

The term "% sequence identity" is defined herein as the percentage of residues in a candidate amino acid sequence that is identical with the residues in a reference sequence after aligning the two sequences and introducing gaps, if necessary, to achieve the maximum percent identity. Methods and computer programs for the alignment are well known in the art. One computer program which may be used or adapted for purposes of determining whether a candidate sequence falls within this definition is "Align 2", authored by Genentech, Inc., which was filed with user documentation in the United States Copyright Office, Washington, D.C. 20559, on Dec. 10, 1991.

An isolated, recombinant or purified CD43 peptide as defined herein is also referred to as "a CD43 peptide according to the invention" or "a CD43 antigen according to the invention". In some embodiments, the amino acid residues of a CD43 peptide according to the invention are chosen from the 20 amino acid residues that naturally occur in eukaryotes, which are also referred to as "standard" or "canonical" amino acids. Alternatively, non-natural amino acid residues are included in a CD43 peptide according to the invention, such as for instance D-amino acids (i.e. D-stereoisomers of amino acids) or N-methyl amino acids.

A CD43 peptide according to the invention is preferably glycosylated. Such peptide more accurately reflects the natural AML antigen in vivo, in view of the fact that the natural CD43 protein on the cell surface is heavily glycosylated. In some preferred embodiments, said CD43 peptide according to the invention comprises sialic acid residues (also called α-N-acetylneuraminic acid). In vivo, human CD43 is highly sialylated. Treatment with neuraminidase cleaves sialic acid residues from the CD43 glycoprotein. In some embodiments, therefore, a CD43 peptide according to the invention is neuraminidase-sensitive. Some embodiments provide a CD43 peptide according to the present invention that has been onco-sialylated, meaning that said CD43 peptide has a tumor-specific sialylation pattern. As used herein, a CD43 peptide according to the invention with a "tumor-specific sialylation pattern" encompasses a CD43 peptide according to the invention with a sialylation pattern that has been produced by a tumor cell, or a CD43 peptide according to the invention with a sialylation pattern that is identical to, or at least 90% or at least 95% or at least 97% similar to, a sialylation pattern as produced by a tumor cell.

Some embodiments provide a CD43 peptide according to the present invention that has been produced by an AML cell. Some embodiments provide a CD43 peptide according to the present invention that has been produced by a cell of a cell line derived from an AML cell. Such CD43 peptide will have a glycosylation pattern that very closely resembles the glycosylation pattern of AML cells in an AML patient in vivo. In some embodiments, said CD43 peptide according to the invention has been produced by a THP-1 cell. In some embodiments, said CD43 peptide according to the invention has been produced by a Kasumi 3 cell, or by an HL60 cell, or by a KGla cell, or by an SH2 cell, or by a MonoMac6 cell, or by a Molm 13 cell, or by a CML K562 cell.

As used herein, a CD43 peptide according to the invention having a glycosylation pattern that is similar or identical to a glycosylation pattern that results from expression of said CD43 peptide in an AML cell, for instance in an AML blast or in an AML cell line, is referred to as a CD43 peptide according to the invention having an AML-specific glycosylation pattern. Some embodiments thus provide a CD43 peptide according to the present invention that has an AML-specific glycosylation pattern.

Some embodiments provide a CD43 peptide according to the present invention that has been produced by an MDS cell. Some embodiments provide a CD43 peptide according to the present invention that has been produced by a cell of a cell line derived from an MDS cell. Such CD43 peptide will have a glycosylation pattern that very closely resembles the glycosylation pattern of MDS cells in an MDS patient in vivo.

Some embodiments provide CD43 peptides according to the present invention that have an MDS-specific glycosylation pattern. These peptides have a glycosylation pattern that is similar or identical to a glycosylation pattern that results from expression of a CD43 peptide according to the invention in an MDS cell, for instance in an MDS blast or in an MDS cell line.

In other embodiments, a CD43 peptide according to the present invention is provided that has been produced by a host cell, using in vitro glycoengineering (for instance according to Roche Diagnostics GmbH). According to these embodiments, host cells are provided with the enzymes alpha-2,6-Sialyltransferase and/or alpha-2,3-Sialyltransferase, so that upon production of a CD43 peptide according to the invention, the peptide will be sialylated. Further provided is therefore a CD43 peptide according to the present invention that has been produced by a cell that contains alpha-2,6-Sialyltransferase and/or alpha-2,3-Sialyltransferase. In some embodiments, said alpha-2,6-Sialyltransferase and/or alpha-2,3-Sialyltransferase comprises exogenous alpha-2,6-Sialyltransferase and/or exogenous alpha-2,3-Sialyltransferase, meaning that the enzyme has been introduced recombinantly into the host cell (or into a parent host cell from which the current host cell originates). Some embodiments provide a CD43 peptide according to the present invention that has been produced by a host cell that contains an exogenous nucleic acid sequence encoding alpha-2,6-Sialyltransferase and/or alpha-2,3-Sialyltransferase.

Anti-CD43 antibodies are known in the art. However, it is clear that these antibodies recognize a different epitope. For instance, as shown in Table 1 of Kim et al, 2014, anti-CD43 monoclonal antibodies (mAbs) YGS, 2C8, 8E10 and DFT-1 do bind AML cells, but also many other non-AML cells, including CEM7, Jurkat, IM9, Ramos, Raji, Daudi, Reh, normal bone marrow and PBL cells, are bound by some or all of these known antibodies (Kim et al, 2014). Hence, antibodies YGS, 2C8, 8E10 and DFT-1 are not at all specific for AML. Contrary, antibody AT14-013, that specifically binds the CD43 peptides according to the present invention, does not bind Jurkat cells, Ramos cells, normal bone marrow cells or PBL cells/PBMCs (FIGS. 5 and 9b). Antibodies YGS, 2C8, 8E10 and DFT-1 thus bind another CD43 epitope.

Antibody UN1 (Tuccillo et al, 2014a and Tuccillo et al, 2014b) recognizes a CD43 epitope including a GalNac-O-linked monosaccharide, corresponding to the Tn antigen of 0-glycans. It was concluded that the protein core of this epitope includes CD43 amino acids 64 to 83. This antigen is expressed by human thymocytes, by the leukemic cell lines HPB-ALL, H9 and Molt-4, and in a subpopulation of peripheral blood CD4+ T-lymphocytes. Antibody AT14-013, however, does not bind human thymocytes, indicating that a different AML antigen is provided by the present invention.

International patent application WO 2007/146172 describes antibodies 5F1, 51-41 and 138-10, which recognize CD43 present on the surface of the human colorectal adenocarcinoma cell line Colo205 and the human gastric carcinoma cell line NCI-N87. AML is not mentioned in WO 2007/146172. Antibody AT14-013, that specifically binds the AML-specific CD43 peptides according to the present invention, does not bind Colo205, as shown in the Examples. Antibodies 5F1, 51-41 and 138-10 thus bind a different CD43 epitope.

International patent application WO 2006/121240 describes antibodies EB-1, EB-2 and EB-3 that are able to recognize an unglycosylated region of CD43, consisting of CD43 amino acids 73-81. This antigen is present on thymocytes, on some hematopoietic precursors in bone marrow, on AML cells, on acute lymphogenous leukemia (ALL) cells and on chronic myelogenous leukemia (CML) cells. EB-1 recognizes its antigen in both sialidase-treated and untreated CD43 molecules. Contrary, glycosylated CD43 peptides according to the present invention are no longer recognized by antibody AT14-013 after treatment with sialidase (neuramidase), meaning that the present invention provides an AML antigen that is neuramidase-sensitive, contrary to the antigen of EB-1, EB-2 and EB-3. Furthermore, antibody AT14-013 does not bind ALL cells or thymocytes, contrary to antibodies EB-1, EB-2 and EB-3. Moreover, the CD43 peptides according to the present invention comprise an amino acid sequence with a length of at least 3 amino acid residues and at most 51 amino acid residues that is identical to a sequence located within amino acid residues 133 and 184 of CD43, which domain is different from CD43 amino acid positions 73-81 that are recognized by antibodies EB-1, EB-2 and EB-3. Antibodies EB-1, EB-2 and EB-3 thus also bind another CD43 epitope.

In conclusion, a novel AML-specific antigen is provided by the present invention.

A CD43 peptide according to the invention preferably has a length of at most 100 amino acid residues and at least 3 amino acid residues, preferably at least 5 amino acid residues, or at least 6 amino acid residues, or at least 7 amino acid residues, or at least 8 amino acid residues, or at least 9 amino acid residues, or at least 10 amino acid residues, or at least 11 amino acid residues, or at least 12 amino acid residues, or at least 13 amino acid residues, or at least 14 amino acid residues, or at least 15 amino acid residues. In some embodiments, said length is at least 20 amino acid residues. In some embodiments, said length is at least 25 amino acid residues. In some embodiments, said length is at least 30 amino acid residues. In some embodiments, said length is at least 33 amino acid residues. In some embodiments, said length is at least 35 amino acid residues. In some embodiments, said length is at least 40 amino acid residues. In some embodiments, said length is at least 45 amino acid residues. In some embodiments, said length is at least 50 amino acids. In some embodiments, said length is at least 51 amino acids. In some embodiments, said length is at least 52 amino acids.

In some embodiments, said length is at most 90 amino acid residues, or at most 85 amino acid residues or at most 75 amino acid residues or at most 70 amino acid residues or at most 65 amino acid residues or at most 60 amino acid residues or at most 55 amino acid residues or at most 52 amino acid residues or at most 51 amino acid residues or at most 50 amino acid residues or at most 45 amino acid residues or at most 40 amino acid residues or at most 35 amino acid residues or at most 30 amino acid residues or at most 25 amino acid residues or at most 20 amino acid. In some embodiments, said peptide has a length of at most 52 amino acid residues and at least 3 amino acid residues, preferably at least 5 amino acid residues, or at least 6 amino acid residues, or at least 7 amino acid residues, or at least 8 amino acid residues, or at least 9 amino acid residues, or at least 10 amino acid residues. In some embodiments, said peptide has a length of at most 51 amino acid residues and at least 3 amino acid residues, preferably at least 5 amino acid residues, or at least 6 amino acid residues, or at least 7 amino acid residues, or at least 8 amino acid residues, or at least 9 amino acid residues, or at least 10 amino acid residues. In some embodiments, said peptide has a length of at most 33 amino acid residues and at least 3 amino acid residues, preferably at least 5 amino acid residues, or at least 6 amino acid residues, or at least 7 amino acid residues, or at least 8 amino acid residues, or at least 9 amino acid residues, or at least 10 amino acid residues. In some embodiments, said peptide has a length of at most 15 amino acid residues and at least 3 amino acid residues, preferably at least 5 amino acid residues, or at least 6 amino acid residues, or at least 7 amino acid residues, or at least 8 amino acid residues, or at least 9 amino acid residues, or at least 10 amino acid residues.

In some embodiments, a CD43 peptide according to the invention consists of an amino acid sequence with a length of at least 3 amino acid residues and at most 51 amino acid residues or at most 51 amino acid residues that is identical to a sequence located between CD43 amino acid positions 133 and 183 as depicted FIG. 13. In some embodiments, a CD43 peptide according to the invention consists of an amino acid sequence with a length of at least 5 amino acid residues and at most 40 amino acid residues that is identical to a sequence located between CD43 amino acid positions 133 and 183 as depicted FIG. 13. In some embodiments, a CD43 peptide according to the invention consists of an amino acid sequence with a length of at least 5 amino acid residues and at most 33 amino acid residues that is identical to a sequence located between CD43 amino acid positions 133 and 183 as depicted FIG. 13. In some embodiments, a CD43 peptide according to the invention consists of an amino acid sequence with a length of at least 5 amino acid residues and at most 20 amino acid residues that is identical to a sequence located between CD43 amino acid positions 133 and 183 as depicted FIG. 13.

In some embodiments, a CD43 peptide according to the invention consists of an amino acid sequence with a length of at least 5 amino acid residues and at most 33 amino acid residues that is identical to a sequence located between CD43 amino acid positions 133 and 165 as depicted FIG. 13. In some embodiments, a CD43 peptide according to the invention consists of an amino acid sequence with a length of at least 5 amino acid residues and at most 30 amino acid residues that is identical to a sequence located between CD43 amino acid positions 133 and 165 as depicted FIG. 13. In some embodiments, a CD43 peptide according to the invention consists of an amino acid sequence with a length of at least 5 amino acid residues and at most 20 amino acid residues that is identical to a sequence located between CD43 amino acid positions 133 and 165 as depicted FIG. 13.

In some embodiments, a CD43 peptide according to the invention consists of an amino acid sequence with a length of at least 5 amino acid residues and at most 15 amino acid residues that is identical to a sequence located between CD43 amino acid positions 133 and 147 as depicted FIG. 13. In some embodiments, a CD43 peptide according to the invention consists of an amino acid sequence with a length of at least 8 amino acid residues and at most 15 amino acid residues that is identical to a sequence located between CD43 amino acid positions 133 and 147 as depicted FIG. 13. In some embodiments, a CD43 peptide according to the invention consists of an amino acid sequence with a length of at least 10 amino acid residues and at most 15 amino acid residues that is identical to a sequence located between CD43 amino acid positions 133 and 147 as depicted FIG. 13.

In some embodiments, the above mentioned peptides are glycosylated, preferably comprising sialic acid residues, in order to better mimic the natural AML-specific antigen. In some embodiments, the above mentioned peptides are onco-sialylated. In some embodiments, the above mentioned peptides have been produced by AML cells or an AML cell line, preferably THP-1 cells. In some embodiments, the above mentioned peptides have been produced by MDS cells or an MDS cell line.

Nucleic acid molecules, or functional equivalents thereof, encoding a CD43 peptide according to the invention are also encompassed by the present invention. Further provided is therefore an isolated, synthetic or recombinant nucleic acid molecule, or a functional equivalent thereof, encoding a CD43 peptide according to the invention. As used herein, a nucleic acid molecule or nucleic acid sequence of the invention preferably comprises a chain of nucleotides, more preferably DNA, cDNA or RNA. In other embodiments a nucleic acid molecule or nucleic acid sequence of the invention comprises other kinds of nucleic acid structures such as for instance a DNA/RNA helix, peptide nucleic acid (PNA), locked nucleic acid (LNA) and/or a ribozyme. Such other nucleic acid structures are referred to as functional equivalents of a nucleic acid sequence. The term "functional equivalent of a nucleic acid molecule" thus encompasses a chain comprising non-natural nucleotides, modified nucleotides and/or non-nucleotide building blocks which exhibit the same function as natural nucleotides.

Some embodiments provide a nucleic acid molecule or functional equivalent thereof according to the invention, wherein a human nucleic acid sequence has been codon optimized for a non-human cell, for instance for a non-human producer cell like *E. coli*, a Chinese hamster ovary (CHO) cell, an NSO cell (which is a mouse myeloma) or a 293(T) cell. This means that one or more codons from said human nucleic acid sequence has/have been replaced by one or more codons that are preferred by said non-human cell.

As used herein, an isolated, synthetic or recombinant nucleic acid molecule, or a functional equivalent thereof, encoding a CD43 peptide according to the invention is also referred to as "a nucleic acid molecule or functional equivalent according to the invention".

Now that the invention has provided CD43 peptides comprising a novel AML-specific antigen, many applications have become possible. For instance, in some embodiments a CD43 peptide according to the invention is used for inducing, isolating and/or obtaining immune cells and/or antibodies, or functional parts or functional derivatives thereof, that are able to specifically bind lymphoproliferative and/or myeloproliferative cells. Immune cells and/or antibodies, or functional parts or functional derivatives thereof, that are induced, isolated and/or obtained with a CD43 peptide according to the invention are particularly suitable for treatment or prevention of myeloproliferative or lymphoproliferative disorders. Even more so in view of the fact that antibody AT14-013, which is an antibody that is specific for a CD43 peptide according to the invention, also targets leukemic stem cells, which are known to be more therapy resistant and often responsible for relapse of disease after treatment. In some embodiments a CD43 peptide according to the invention is used for inducing and/or obtaining AML-specific immune cells and/or AML-specific antibodies. For instance, a non-human animal is immunized with one or more CD43 peptides according to the present invention, or with an immunogenic compound comprising a CD43 peptide according to the present invention, or with a nucleic acid molecule or functional equivalent thereof encoding a CD43 peptide according to the invention, or with a vector comprising a nucleic acid molecule or functional equivalent according to the invention, preferably followed by one or more booster administrations. Subsequently, immune cells and/or antibodies that are specific for lymphoproliferative and/or myeloproliferative cells, preferably specific for AML, are harvested from said non-human animal. In some embodiments, said immune cells comprise T cells, such as for instance NK cells or T-helper cells.

In some embodiments, said immune cells harvested from said immunized non-human animal comprise B cells. for instance, AML-specific B-cells are particularly suitable for the production of AML-specific antibodies. AML-specific B-cells harvested from said immunized animal are for instance used for the production of hybridomas, from which AML-specific antibodies are obtained. In other embodiments, B-cells harvested from said immunized animal are transduced with Bcl-6 and Bcl-xL nucleic acids and cultured in long term ex vivo B cell cultures as for instance described in European Patent No. 1974017 and U.S. Pat. No. 9,127,251. This way, long term replicating B cell cultures are generated, wherein the B cells both replicate and produce antibody. In some embodiments, AML-specific antibodies produced by said hybridomas or by such B cell culture are harvested and for instance used for anti-AML therapy, preferably after humanization of the antibodies in order to reduce side-effects. In some embodiments, an antibody and/or B cell obtained from said non-human animal is tested for competition with antibody AT14-013 for binding to CD43. This is for instance done by incubating AML cells with said antibody or B cell obtained from said non-human animal, and subsequently adding antibody AT14-013. As a control, AML cells are preferably incubated with antibody AT14-013 in the absence of any other antibody or B cell. If pre-incubation of AML cells with an antibody or B cell obtained from said non-human animal appears to affect the binding of AT14-013 to said AML cells, it is concluded that said antibody or B cell obtained from said non-human animal competes with antibody AT14-013 for binding to CD43.

In some embodiments, the variable domain-encoding nucleic acid sequences of B cells from said non-human animal are sequenced in order to obtain the nucleic acid sequences of AML-specific variable domains, where after one or more nucleic acid molecules comprising these sequences are introduced in producer cells, such as for instance E. coli, Chinese hamster ovary (CHO) cells, NSO cells or 293(T) cells, for the production of AML-specific antibodies. Said one or more nucleic acid sequences are preferably codon optimized for said producer cell. As used herein, the term "codon" means a triplet of nucleotides (or functional equivalents thereof) that encode a specific amino acid residue. The term "codon optimized" means that one or more codons from the original, animal nucleic acid sequence are replaced by one or more codons that are preferred by a cell from another species, such as for instance a certain producer cell. These replacement codons preferably encode the same amino acid residue as the original animal codon that has been replaced.

In some embodiments, CD43-specific antibodies obtained from said non-human animal or from immune cells of said non-human animal are humanized, meaning that at least part of the animal amino acid sequence, preferably at least part or the whole of the framework sequences, is replaced by a human sequence in order to reduce adverse side-effects in humans.

Animal immunization protocols, including suitable administration procedures and adjuvants, procedures for obtaining and purifying antibodies and/or immune cells from such immunized animals, competition experiments and humanization procedures of non-human antibodies are well known in the art. Reference is for instance made to Hanly et al, 1995.

In some embodiments, a CD43 peptide according to the present invention, or a compound comprising a CD43 peptide according to the present invention, is used for screening a phage display library in order to identify and/or isolate AML-specific immunoglobulins (typically Fab fragments). In some embodiments, a nave phage display library is used. In preferred embodiments, a phage display library derived from one or more AML patients is used, so that the library will already be biased towards AML. In some embodiments, an AML-specific immunoglobulin obtained from said phage display library is tested for competition with antibody AT14-013 for binding to CD43. This is for instance done using a competition test described herein.

Further provided is therefore a use of a CD43 peptide according to the invention, or a use of an immunogenic compound according to the invention, or a use of a nucleic acid molecule or functional equivalent thereof encoding a CD43 peptide according to the invention, or a use of a vector comprising a nucleic acid molecule or functional equivalent according to the invention, for inducing, isolating and/or obtaining an immune cell or an antibody, or a functional part or functional equivalent thereof, such as for instance a Fab fragment. Said immune cell or antibody or functional part or functional equivalent thereof is preferably able to specifically bind lymphoproliferative cells and/or myeloproliferative cells. Preferably, said myeloproliferative cells are AML cells, MDS cells and/or CML cells, most preferably AML cells. In some embodiments, a CD43 peptide according to the invention or an immunogenic compound according to the invention or a nucleic acid molecule or functional equivalent according to the invention or a vector comprising a nucleic acid molecule or functional equivalent according to the invention is used for inducing and/or obtaining an antibody that is able to induce antibody-dependent cellular cytotoxicity (ADCC) or complement-dependent cytotoxicity (CDC). A non-limiting example of such antibody is AT14-013, as shown in the Examples. The fact that a CD43 peptide according to the invention, or an immunogenic compound according to the invention, is able to induce and/or obtain an antibody with ADCC and/or CDC inducing activity means that antibodies can be induced or obtained that are functional in vivo.

A CD43 peptide or compound according to the invention for use as an immunogen is also herewith provided, as well as a nucleic acid molecule or functional equivalent according to the invention, or a vector comprising a nucleic acid molecule or functional equivalent according to the invention, for use as an immunogen.

Some embodiments provide a method for producing immune cells and/or antibodies that are able to specifically bind lymphoproliferative cells and/or myeloproliferative cells, such as for instance an AML-specific immune cell or an AML-specific antibody, the method comprising immunizing a non-human animal with a CD43 peptide according to the present invention, or with a compound according to the invention or with a nucleic acid molecule or functional equivalent according to the invention or with a vector comprising a nucleic acid molecule or functional equivalent according to the invention. The method preferably further comprises harvesting an immune cell and/or antibody that is able to specifically bind lymphoproliferative cells and/or myeloproliferative cells from said non-human animal. In some embodiments, an AML-specific immune cell and/or an AML-specific antibody is harvested from said non-human animal. In some embodiments, a B cell and/or antibody obtained from said non-human animal is tested for competition with antibody AT14-013 for binding to CD43. An immune cell and/or antibody that is able to specifically bind lymphoproliferative cells and/or myeloproliferative cells obtainable by a method according to the present invention is also provided herewith. Some embodiments provide an AML-specific antibody or an AML-specific immune cell obtainable by a method according to the present invention for producing an AML-specific immune cell or an AML-specific antibody. Such AML-specific antibody preferably competes with antibody AT14-013 for binding to CD43.

Said non-human animal preferably comprises a mammal such as a rodent or cattle. In some embodiments said non-human animal comprises a mouse, a rat, a rabbit, a llama, a camel, a pig, poultry, a cow, a goat, a horse, an ape, and/or a gorilla.

In view of the fact that antibody AT14-013 specifically binds a CD43 peptide according to the present invention, other antibodies that are obtained, produced or selected with a CD43 peptide according to the invention will typically compete with antibody AT14-013 for binding to CD43. Contrary, current CD43 antibodies that are known in the art do not compete with antibody AT14-013, whereas these known antibodies do compete with each other, as shown in FIG. 9. These other antibodies known in the art thus clearly bind an epitope that is different from the epitope of AT14-013. Further provided is, therefore, an isolated, recombinant or purified antibody, or a functional part or a functional equivalent thereof, that competes with antibody AT14-013 for binding to CD43. Said isolated, recombinant or purified antibody, or functional part or functional equivalent thereof, preferably competes with antibody AT14-013 for binding to at least part of an epitope that is located between amino acids 133 and 184 of a CD43 sequence as depicted in FIG. 13. Said isolated, recombinant or purified antibody or functional part or functional equivalent typically competes with antibody AT14-013 for binding to a CD43 peptide according to the present invention.

The term "antibody" as used herein, refers to an immunoglobulin protein comprising two heavy chains, bound to each other, wherein each heavy chain is also paired with a light chain.

A "functional part of an antibody" is defined herein as a part that has at least one shared property as said antibody in kind, not necessarily in amount. Said functional part is capable of binding the same antigen as said antibody, albeit not necessarily to the same extent. A functional part of an antibody preferably comprises at least a heavy chain variable domain (VH) and a light chain variable domain (VL). In some embodiments, a functional part of an antibody comprises at least a heavy chain variable domain (VH). Non-limiting examples of a functional part of an antibody are a single domain antibody, a single chain antibody, a nanobody, an unibody, a single chain variable fragment (scFv), a bi-specific T-cell engager (BiTE), a Fab fragment and a F(ab')$_2$ fragment.

A "functional equivalent of an antibody" is defined herein as an artificial binding compound, comprising at least one CDR sequence of an antibody, preferably a heavy chain CDR3 sequence. Said functional equivalent preferably comprises the heavy chain CDR3 sequence of an antibody, as well as the light chain CDR3 sequence of said antibody. More preferably, said functional equivalent comprises the heavy chain CDR1, CDR2 and CDR3 sequences of an antibody, as well as the light chain CDR1, CDR2 and CDR3 sequences of said antibody. A functional equivalent of an antibody is for instance produced by altering an antibody such that at least an antigen-binding property of the resulting compound is essentially the same in kind, not necessarily in amount. This is done in many ways, for instance through conservative amino acid substitution, whereby an amino acid residue is substituted by another residue with generally similar properties (size, hydrophobicity, etc), such that the overall functioning of the antibody is essentially not affected. A non-limiting example of a functional equivalent of an antibody is an antibody with a modified Fc tail, which Fc tail has for instance been modified by amino acid replacement(s) and or glycosylation alteration(s).

As is well known by the skilled person, a heavy chain of an antibody is the larger of the two types of chains making up an immunoglobulin molecule. A heavy chain comprises a constant domain and a variable domain, which variable domain is involved in antigen binding. A light chain of an antibody is the smaller of the two types of chains making up an immunoglobulin molecule. A light chain comprises a constant domain and a variable domain. The variable domain is often, but not always, together with the variable domain of the heavy chain involved in antigen binding.

Complementary-determining regions (CDRs) are the hypervariable regions present in heavy chain variable domains and light chain variable domains. In case of whole antibodies, the CDRs 1-3 of a heavy chain and the CDRs 1-3 of the connected light chain together form the antigen-binding site.

As used herein, an immune cell, antibody or functional part or functional equivalent thereof is "specific" for AML if it is able to bind AML cells with a binding affinity that is at least two times higher than the binding affinity of an irrelevant control antibody or control immune cell to said AML cells (wherein the control antibody or control immune cell is not specific for said AML cells). For instance, AML binding by an AML-specific antibody, B cell or T cell is typically mediated through the complementarity regions of the antibody, B cell receptor (BCR) or T cell receptor (TCR), respectively. The specific three-dimensional structure of both the AML antigen and the variable domain of the antibody or BCR or TCR allow these two structures to bind together (an interaction similar to a lock and key), as opposed to random, non-specific sticking of antibodies or BCRs or TCRs. Some reactivity towards other types of cells is, however, embraced within the term "AML-specific". As an antibody or BCR or TCR typically recognizes an epitope of an antigen, and as such epitope might be present on other cells as well, AML-specific antibodies, B cells or T cells might then recognize such other cells. Non-limiting examples of such other cells are MDS and CML cells. Also melanoma cells and melanocytes appear to be bound by the AML-specific antibody AT14-013, albeit to a lesser extent. Hence, the term "AML-specific" does not exclude binding of the antibodies or B cells or T cells to another cell that contains at least part of the same epitope. It is, however, shown in the Examples that many CD43+ cells, including CD43+ hematopoietic cells such as for instance PBMCs, (precursor) T cells and B cells, do not contain an AML antigen as provided by the present invention.

CD43 peptides according to the present invention are particularly suitable for testing for the presence of AML-specific binding compounds, such as for instance AML-specific antibodies or AML-specific immune cells such as B cells or T cells, in a biological sample. For instance, a sample from an individual, or a fraction of such sample that comprises antibodies, B cells and/or T cells, is incubated with a CD43 peptide according to the present invention, or with a compound that comprises a CD43 peptide according to the invention, in order to screen for the presence of AML-specific antibodies and/or AML-specific immune cells. If such antibodies or immune cells appear to be present in said sample or in said sample fraction, and to bind said CD43 peptide according to the present invention, said sample is typed as being positive for AML-specific binding compounds (i.e. antibodies and/or immune cells). Said sample for instance comprises a blood sample, or a bone marrow sample, or a biopsy such as for instance a myeloid sarcoma (also called a chloroma).

An AML-specific antibody or AML-specific immune cell is for instance detected and/or quantified using an immunoassay, such as for instance a Western blot, a (capture) ELISA or RIA. These assays are well known in the art. Labelled CD43 peptides according to the invention are for instance incubated with a blood sample or bone marrow sample or with or a biopsy such as for instance a myeloid sarcoma, or with a fraction of such sample that comprises antibodies, B cells and/or T cells, where after unbound binding compounds are washed away. Subsequently, it is determined whether the CD43 peptides according to the invention are bound by AML-specific antibodies or immune cells. In some embodiments, an unlabeled CD43 peptide according to the invention, or an unlabeled compound comprising a CD43 peptide according to the invention, is contacted with a sample that comprises antibodies and/or immune cells, such as for instance a blood sample or bone marrow sample or a biopsy such as for instance a myeloid sarcoma, or with a fraction of such sample that comprises antibodies, B cells and/or T cells. After incubation, one or more washing steps are preferably performed in order to remove non-bound antibodies and unbound immune cells. Subsequently, it is tested whether antibodies or immune cells have bound said CD43 peptide according to the invention, for instance using an antibody that is specifically directed against human antibodies or human immune cells and that is coupled to a marker, such as for instance a fluorescent compound or for instance horseradish peroxidase or alkaline phosphatase. After a further washing step, it is determined whether the second antibody has bound, for instance by measuring light emission or by adding a substrate of horseradish peroxidase or alkaline phosphatase. These detection techniques are well known in the art.

In some embodiments, a CD43 peptide according to the invention, or a compound that comprises a CD43 peptide according to the invention, is contacted with a fraction of a sample that has been enriched for antibodies and/or immune cells. In some embodiments, said fraction is an in vitro B cell culture or an in vitro T cell culture. In some embodiments, a CD43 peptide according to the invention or a compound that comprises a CD43 peptide according to the invention is contacted with antibodies and/or immune cells that have been essentially purified from a biological sample, such as for instance a purified B cell fraction that has been obtained by selecting for CD19 positive cells and/or an antibody/B cell fraction that has been purified using an anti Ig antibody or a protein A or G purification method. Protein A or G purification methods are well known in the art and protocols and reagents are commercially available. As used herein, the term "immune cells that have been essentially purified from a sample" means that at least 80%, preferably at least 85%, more preferably at least 90% or at least 95%, of the cells of a resulting fraction consists of immune cells. The term "antibodies that have been essentially purified from a sample" means that at least 80%, more preferably at least 85%, more preferably at least 90% or at least 95%, of the mass of a resulting fraction consists of antibodies.

Further provided is therefore a use of a CD43 peptide according to the invention, or a use of a compound that comprises a CD43 peptide according to the invention, for binding and/or detecting an immune cell and/or an antibody, or a functional part or functional equivalent thereof. Said immune cell and/or antibody or functional part or functional equivalent thereof is preferably able to specifically bind lymphoproliferative cells and/or myeloproliferative cells. Preferably, said myeloproliferative cells are AML cells or MDS cells or CML cells, preferably AML cells. A CD43 peptide according to the invention, or a compound that comprises a CD43 peptide according to the invention, for use as a detection moiety for AML-specific binding compounds such as antibodies and/or immune cells is also herewith provided, as well as a method for determining whether a sample comprises AML-specific antibodies and/or AML-specific immune cells, the method comprising incubating a CD43 peptide according to the invention, or a compound that comprises a CD43 peptide according to the invention, with said sample, or with a fraction of said sample that comprises antibodies and/or immune cells, and subsequently determining whether said CD43 peptide according to the invention is bound by AML-specific antibodies and/or AML-specific immune cells, or whether said compound that comprises said CD43 peptide according to the invention is bound by AML-specific antibodies and/or AML-specific immune cells. If such binding is detected, it is concluded that said sample comprises AML-specific antibodies and/or AML-specific immune cells.

Also provided is a method for determining whether a sample comprises AML-specific antibodies and/or AML-specific immune cells, the method comprising incubating a CD43 peptide according to the invention, or a compound that comprises a CD43 peptide according to the invention, with antibodies and/or immune cells that have been essentially purified from said sample, and subsequently determining whether said CD43 peptide according to the invention is bound by AML-specific antibodies and/or AML-specific immune cells, or whether said compound that comprises said CD43 peptide according to the invention is bound by AML-specific antibodies and/or AML-specific immune cells.

In some embodiments, the results of detection tests as described above are used for determining whether an individual has AML. If a sample from an individual appears to contain AML-specific immune cells and/or AML-specific antibodies, it can be concluded that said individual is an AML patient. A CD43 peptide according to the invention for use as a diagnostic agent is therefore also provided herewith, as well as a compound that comprises a CD43 peptide according to the invention for use as a diagnostic agent. Further provided is a use of a CD43 peptide according to the invention for diagnosing AML, as well as a use of a compound that comprises a CD43 peptide according to the invention for diagnosing AML. Further provided is a diagnostic kit comprising:

a CD43 peptide according to the invention, or a compound that comprises a CD43 peptide according to the invention, and means for detecting an antibody-bound CD43 peptide or an immune cell-bound CD43 peptide.

Such means for instance encompass labelled antibodies that are specifically directed against human antibodies or human immune cells. In some embodiments, said labelled antibodies are conjugated with horseradish peroxidase or alkaline phosphatase.

Some embodiments provide a diagnostic kit comprising:

a CD43 peptide according to the invention, or a compound that comprises a CD43 peptide according to the invention, and means for detecting an antibody or an immune cell.

Such means for instance encompass labelled antibodies that are specifically directed against human antibodies or human immune cells. In some embodiments, said labelled antibodies are conjugated with horseradish peroxidase or alkaline phosphatase.

Some embodiments provide a method for typing an antibody-containing sample or an immune cell-containing sample, the method comprising contacting a CD43 peptide according to the invention (optionally in the context of an MHC complex in order to detect T cells), or a compound that comprises said CD43 peptide according to the invention, with antibodies and/or immune cells of said sample and determining whether said CD43 peptide according to the invention, or said compound according to the invention, is bound by at least one of said antibodies and/or immune cells of said sample. If said CD43 peptide or said compound according to the invention is bound by antibodies and/or immune cells of said sample, said sample is typed as comprising CD43-specific antibodies and/or immune cells.

Some embodiments provide a method for determining whether an individual has a myeloproliferative or lymphoproliferative disorder, preferably AML, the method comprising contacting a CD43 peptide according to the invention (optionally in the context of an MHC complex in order to detect T cells), or a compound that comprises said CD43 peptide according to the invention, with antibodies and/or immune cells of said individual and determining whether said CD43 peptide according to the invention, or said compound according to the invention, is bound by at least one of said antibodies and/or immune cells of said individual. If said CD43 peptide or said compound according to the invention is bound by antibodies and/or immune cells of said individual, it is concluded that said individual has a lymphoproliferative or myeloproliferative disorder such as AML. In some embodiments, said CD43 peptide according to the invention, or said compound comprising said CD43 peptide according to the invention, is contacted with a sample that comprises antibodies and/or immune cells of said individual, such as for instance a blood sample or a bone marrow sample or a biopsy such as for instance a myeloid sarcoma. In other embodiments, said CD43 peptide or compound according to the invention is contacted with a fraction of a sample from said individual, wherein said fraction comprises immune cells and/or antibodies. In some embodiments, said CD43 peptide or compound according to the invention is contacted with antibodies and/or immune cells that have been essentially purified from said sample, such as for instance a purified B cell fraction that has been obtained by selecting for CD19 positive cells and/or an antibody/B cell fraction that has been purified using an anti Ig antibody or a protein A or G purification method.

In some embodiments, the results of detection tests according to the invention are used for determining whether an individual exhibits a detectable immune response against a myeloproliferative or lymphoproliferative disorder such as AML. This is for instance preferred for determining whether a patient suffering from a myeloproliferative disorder who has received medical treatment, such as for instance an AML patient who has been treated against AML, for instance an AML patient who has received immunotherapy such as a stem cell transplantation or donor-lymphocyte infusion, has a GvL response. To date, there are no diagnostic tools to test for the presence of a potent GvL response in a treated patient. Such diagnostic tool is much needed, for instance because: 1) It will allow early identification of allogeneic SCT recipients at high risk for relapse, at a time-point before relapse has occurred thereby allowing earlier interventions such as tapering of immunosuppressants or donor-lymphocyte infusions; 2) It will allow titrating such donor lymphocyte infusions until anti-leukemia antibodies do appear; and 3) It will offer hope for allogeneic SCT recipients at a time they often suffer from one of many SCT-related complications when the presence of a potent GvL response can be demonstrated. Nowadays patients have to wait and see whether or not a relapse occurs, and there is no way to predict relapse of disease. The availability of a test for determining whether a patient has an anti-AML immune response will therefore greatly improve the clinical care of SCT patients, affecting prognosis and quality of life.

Some embodiments therefore provide a method for determining whether an individual exhibits an immune response against a myeloproliferative or lymphoproliferative disorder, preferably AML, the method comprising contacting a CD43 peptide according to the invention, optionally in the context of an MHC complex, or a compound that comprises said CD43 peptide according to the invention, with antibodies and/or immune cells of said individual and determining whether said CD43 peptide according to the invention, or said compound comprising said CD43 peptide according to the invention, is bound by at least one of said antibodies and/or immune cells of said individual. If said CD43 peptide or said compound appears to be bound, it indicates that said individual exhibits an immune response against said myeloproliferative or lymphoproliferative disorder, preferably AML. In some embodiments it is determined whether antibodies or B cells of said individual compete with antibody AT14-013 for binding to CD43. Competing antibodies will be particularly effective against a myeloproliferative or lymphoproliferative disorder, preferably AML.

In some embodiments, an antibody or a functional part or a functional equivalent thereof that competes with antibody AT14-013 for binding to CD43 is used for detecting myeloproliferative cells in a sample. Further provided is therefore a use of an isolated, recombinant or purified antibody, or a functional part or a functional equivalent thereof, that competes with antibody AT14-013 for binding to CD43, for determining whether a sample comprises myeloproliferative cells, preferably AML or MDS or CML cells. An isolated, recombinant or purified antibody, or a functional part or a functional equivalent thereof, that competes with antibody AT14-013 for binding to CD43, for use in diagnosis of a lymphoproliferative or myeloproliferative disorder, preferably AML or MDS or CML, is also provided herewith, as well as a use of an isolated, recombinant or purified antibody, or a functional part or a functional equivalent thereof, that competes with antibody AT14-013 for binding to CD43, for diagnosing AML. Also provided is a use of an isolated, recombinant or purified antibody, or a functional part or a functional equivalent thereof, that competes with antibody AT14-013 for binding to CD43, for the preparation of a diagnostic agent for lymphoproliferative or myeloproliferative cells, preferably AML or MDS or CML cells. Some embodiments provide a diagnostic kit comprising an isolated, recombinant or purified antibody, or a functional part or a functional equivalent thereof, that competes with antibody AT14-013 for binding to CD43, and means for detecting an antibody-cell complex. Said means for instance comprise another antibody against AML cells, such as for instance AT14-013. In some embodiments, said means comprise labelled antibodies against another cell surface component of myeloid cells. In some embodiments, said means comprise labelled antibodies against said antibody or functional part or functional equivalent that competes with antibody AT14-013.

An isolated, recombinant or purified antibody, or a functional part or a functional equivalent thereof, that competes with antibody AT14-013 for binding to CD43, for use as a diagnostic agent is also provided. Some embodiments provide a method for determining whether myeloproliferative cells are present in a sample comprising:

contacting said sample with an isolated, recombinant or purified antibody, or a functional part or a functional equivalent thereof, that competes with antibody AT14-013 for binding to CD43, and allowing said antibody or functional part or functional equivalent to bind myeloproliferative cells, if present, and determining whether or not myeloproliferative cells are bound to said antibody or functional part or functional equivalent, thereby determining whether or not myeloproliferative cells are present in said sample. In some embodiments, said myeloproliferative cells are AML or MDS or CML cells.

Further provided is a use of antibody AT14-013, or a functional part or a functional equivalent thereof, for determining whether a sample comprises AML or MDS or CML cells. Antibody AT14-013, or a functional part or a functional equivalent thereof, for use in diagnosis of AML or MDS or CML is also provided herewith, as well as a use of antibody AT14-013, or a functional part or a functional equivalent thereof, for diagnosing AML or MDS or CML. Also provided is a use of antibody AT14-013, or a functional part or a functional equivalent thereof, for the preparation of a diagnostic agent for AML or MDS or CML.

Other interesting applications of the novel CD43 peptides according to the present invention and nucleic acid molecules or functional equivalents encoding therefore are prophylactic or semi-prophylactic applications and immunotherapy. As used herein, a semi-prophylactic application means that an individual already has a disease, but further progression of said disease is at least temporarily delayed or prevented. For instance, a CD43 peptide according to the present invention, or a nucleic acid molecule or functional equivalent thereof encoding therefore, or a vector comprising a nucleic acid molecule or functional equivalent according to the invention, or a compound that comprises a CD43 peptide according to the invention, can be semi-prophylactically administered to an individual who is suffering from intermediate to high risk myelodysplastic syndrome (MDS). As described herein before, such patient has an intermediate to high risk to develop AML, so that it is advantageous to elicit an anti-AML immune response in said patient beforehand, using a CD43 peptide or compound or nucleic acid molecule or functional equivalent or vector according to the invention, before the MDS progresses to AML. Another example of a semi-prophylactic application of a CD43 peptide according to the present invention, or a compound or a nucleic acid molecule or a functional equivalent or a vector according to the invention, is its use for AML, MDS or CML patients who received an allogeneic hematopoietic stem cell transplantation (HSCT). The goal of such allogeneic HSCT is to evoke an allogeneic graft versus leukemia/MDS response, but there is currently no approach available to ascertain the development of such response. The present invention provides a use of a CD43 peptide according to the invention, or a nucleic acid molecule or a functional equivalent encoding therefore, or use of a vector comprising a nucleic acid molecule or functional equivalent according to the invention, or use of a compound that comprises a CD43 peptide according to the invention, as a prophylactic or semi-prophylactic agent that induces an alloreactive immune response against CD43-expressing malignant cells (graft vs tumor response, for example against MDS, AML, or CML). Another example of a prophylactic or semi-prophylactic application of a CD43 peptide according to the present invention, or a compound or a nucleic acid molecule or a functional equivalent or a vector according to the invention, is its use for CML patients. Nowadays, CML is well controlled in many patients using tyrosine kinase inhibitors such as for instance Imatinib. However, a patient may develop resistance to one or more tyrosine kinase inhibitors. Moreover, the use of tyrosine kinase inhibitors sometimes involves adverse side effects like edema, skin rashes, fatigue, nausea and myelosuppression. Tyrosine kinase inhibitors are also expensive. The present invention provides a use of a CD43 peptide according to the invention, or a nucleic acid molecule or a functional equivalent encoding therefore, or use of a vector comprising a nucleic acid molecule or functional equivalent according to the invention, or use of a compound that comprises a CD43 peptide according to the invention, as a prophylactic agent or semi-prophylactic agent that delays or prevents the progression of CML to AML. In some embodiments, said CD43 peptide or compound or nucleic acid molecule or functional equivalent or vector according to the invention is used instead of a tyrosine kinase inhibitor, for instance in order to reduce adverse side-effects and/or costs. In other embodiments, said CD43 peptide or compound or nucleic acid molecule or functional equivalent or vector according to the invention is used together with one or more tyrosine kinase inhibitors. A CD43 peptide according to the invention, or a compound that comprises a CD43 peptide according to the invention, or a nucleic acid molecule or a functional equivalent thereof encoding a CD43 peptide according to the invention, or a vector comprising a nucleic acid molecule or functional equivalent according to the invention, for use as a prophylactic agent or semi-prophylactic agent is therefore also herewith provided. Also provided is a use of a CD43 peptide according to the invention, or use of a compound that comprises a CD43 peptide according to the invention, or use of a nucleic acid molecule or functional equivalent thereof encoding a CD43 peptide according to the invention, or use of a vector comprising a nucleic acid molecule or functional equivalent according to the invention, for the preparation of a prophylactic agent or semi-prophylactic agent against AML, for instance for an AML patient that has received allogenic HSCT. In some embodiments, said semi-prophylactic agent is for a MDS or CML patient, as explained above. Said prophylactic agent or semi-prophylactic agent preferably comprises a vaccine. As used herein, the term "prophylactic agent" also encompasses semi-prophylactic agents.

In some embodiments, a CD43 peptide or compound or nucleic acid molecule or functional equivalent or vector according to the invention is used for treatment of a myeloproliferative or lymphoproliferative disorder, preferably AML. As used herein, "treatment" encompasses alleviation of at least one symptom, and/or delaying or even halting the progression of disease, at least temporarily. In one preferred embodiment, a CD43 peptide according to the invention, optionally in the context of an MHC complex, or a nucleic acid molecule or a functional equivalent encoding therefore, or a vector comprising a nucleic acid molecule or functional equivalent according to the invention, or a compound that comprises said CD43 peptide according to the invention, is administered to an AML patient in order to boost his/her immune system, resulting in an enhanced immune response. In some embodiments, naïve T cells or B cells from an AML patient are cultured ex vivo and incubated with a CD43 peptide or compound according to the invention, optionally in the context of an MHC complex in case of a T cell culture, in order to obtain AML-specific T cells or B cells that are subsequently administered to the patient, optionally after ex vivo expansion. In some embodiments it is determined whether AML-specific B cells from said AML patient compete with antibody AT14-013 for binding to CD43, because competing B cells will be particularly effective against AML, in particular in view of the fact that AT14-013 also targets leukemic stem cells, which are known to be more therapy resistant and often responsible for relapse of disease after treatment.

In some embodiments, adoptive cell therapy is used. In some embodiments, T cells from an AML patient are tested for binding or activation using a CD43 peptide according to the invention in the context of an MHC complex, or using a compound comprising a CD43 peptide according to the invention in the context of an MHC complex, and T cells recognizing said CD43 peptide are preferably expanded ex vivo and subsequently administered to the patient, which will result in an anti-AML T cell response.

In some embodiments, adoptive cell therapy of donor lymphocytes is used. Donor T cells isolated from an AML patient who received allogeneic HSCT, or isolated from the HSCT donor, are preferably tested for binding or activation using a CD43 peptide according to the invention in the context of an MHC complex, or using a compound comprising a CD43 peptide according to the invention in the context of an MHC complex, and donor T cells recognizing said CD43 peptide are preferably expanded ex vivo and subsequently administered to the patient, which will result in an anti-AML allogeneic T cell response.

In some embodiments, T cells are modified in order to provide them with an AML-specific binding moiety. Said T cells are preferably derived from an AML patient or an MDS patient or a CML patient or a HSCT donor. In some embodiments, chimeric antigen receptor (CAR) T cells are produced. These are T cells with modified T cell receptors, which have been provided with a binding specificity of interest, preferably derived from an antibody. Typically, CAR T cells are produced by fusing a single-chain variable domains (scFv) derived from a monoclonal antibody to the CD3-zeta transmembrane domain, so that a zeta signal will be elicited upon target recognition by the scFv.

According to some embodiments, a CD43 peptide according to the invention, or a nucleic acid molecule or a functional equivalent encoding therefore, or a vector comprising a nucleic acid molecule or functional equivalent according to the invention, or a compound that comprises a CD43 peptide according to the invention, is used in order to produce and/or isolate a CD43-specific B cell and/or antibody, which in turn is used for the production of a modified T cell. For instance, said CD43 peptide or compound or nucleic acid molecule or functional equivalent or vector is used in order to elicit, detect and/or isolate an AML-specific antibody or AML-specific B cell. Subsequently, in some embodiments the heavy chain and/or light chain variable domains of said antibody or B cell are provided to T cells, thereby producing modified T cells with an AML specificity. In some embodiments, these modified T cells are subsequently administered to an AML patient, which will result in an AML-specific T cell response. In some embodiments, said modified T cells are CAR T cells. In some embodiments said AML-specific antibodies or AML-specific B cells are tested for competition with antibody AT14-013 for binding to CD43 before the heavy chain and/or light chain variable domains of said antibodies or B cells are provided to T cells. Such competing antibodies are preferably selected for producing modified T cells with an AML specificity.

Further provided is therefore a CD43 peptide according to the invention, optionally in the context of an MHC complex, or a compound that comprises said CD43 peptide according to the invention, or a nucleic acid molecule or functional equivalent thereof encoding a CD43 peptide according to the invention, or a vector comprising a nucleic acid molecule or functional equivalent according to the invention, for use as a medicament. Also provided is a use of a CD43 peptide according to the invention, optionally in the context of an MHC complex, or a compound that comprises said CD43 peptide according to the invention, or a nucleic acid molecule or functional equivalent thereof encoding a CD43 peptide according to the invention, or a vector comprising a nucleic acid molecule or functional equivalent according to the invention, for the production of AML-specific T cells. Some embodiments provide a method for producing a modified T cell, the method comprising contacting an antibody-containing sample from an AML patient or a B cell-containing sample from an AML patient with a CD43 peptide or compound according to the invention, resulting in bound antibodies or B cells against AML, and subsequently obtaining one or more AML-specific domains from an AML-specific antibody or from an AML-specific B cell from said AML patient and providing said one or more domains to a T cell. Some embodiments provide a method for producing a modified T cell, the method comprising immunizing a non-human animal with a CD43 peptide or compound or nucleic acid molecule or functional equivalent or vector according to the invention, thereby eliciting an immune response against AML, and subsequently obtaining one or more AML-specific domains from an AML-specific antibody or an AML-specific B cell from said non-human animal, or obtaining one or more nucleic acid sequences encoding for said one or more AML-specific domains, optionally after it has been determined whether said AML-specific antibody or AML-specific B cell competes with antibody AT14-013 for binding to CD43, and providing said one or more domains, or said one or more nucleic acid sequences, to a T cell. A CD43 peptide or compound according to the invention for use in immunotherapy is also provided herewith, as well as a CD43 peptide according to the invention in the context of an MHC complex for use in immunotherapy, as well as a nucleic acid molecule or functional equivalent thereof encoding a CD43 peptide according to the invention for use in immunotherapy. Some embodiments provide a vector comprising a nucleic acid molecule or functional equivalent according to the invention for use in immunotherapy. Further provided is a use of a CD43 peptide according to the invention, or a use of a compound that comprises a CD43 peptide according to the invention, or a use of a nucleic acid molecule or functional equivalent thereof encoding a CD43 peptide according to the invention, or a use of a vector comprising a nucleic acid molecule or functional equivalent according to the invention, for the preparation of a medicament against a myeloproliferative or lymphoproliferative disorder, preferably AML.

Also provided is an immunogenic composition comprising a CD43 peptide according to the invention, and/or comprising a compound that comprises a CD43 peptide according to the invention, and/or comprising a nucleic acid molecule or functional equivalent thereof encoding a CD43 peptide according to the invention, and/or comprising a vector that comprises a nucleic acid molecule or functional equivalent according to the invention. Said immunogenic composition preferably further comprises a biocompatible additive, such as for instance a carrier, diluent, excipient or filler. Some embodiments provide a vaccine comprising a CD43 peptide according to the invention, optionally in the context of an MHC complex. Some embodiments provide a vaccine comprising a compound that comprises said CD43 peptide according to the invention, and a vaccine comprising a nucleic acid molecule or functional equivalent thereof encoding a CD43 peptide according to the invention, and a vaccine comprising a vector that comprises a nucleic acid molecule or functional equivalent according to the invention. Other embodiments provide a composition comprising a CD43 peptide according to the invention, or a composition comprising a compound that comprises a CD43 peptide according to the invention, or a composition comprising a nucleic acid molecule or functional equivalent thereof encoding a CD43 peptide according to the invention, or a composition comprising a vector that comprises a nucleic acid molecule or functional equivalent according to the invention, wherein said composition is a pharmaceutical composition which further comprises a pharmaceutically acceptable carrier, diluent or excipient.

In some embodiments, an isolated, recombinant or purified antibody, or a functional part or a functional equivalent thereof, that competes with antibody AT14-013 for binding to CD43 is used for treatment of a myeloproliferative or lymphoproliferative disorder, preferably AML. As described in WO 2015/093949, antibody AT14-013 was obtained from an AML patient in complete remission, demonstrating that AT14-013 is effective against AML. Moreover, AT14-013 also targets leukemic stem cells, which are known to be more therapy resistant and often responsible for relapse of disease after treatment. Antibodies that compete with AT14-013 for binding to CD43 will therefore also be very effective against myeloproliferative disorders like AML. Hence, administration of such antibodies to an AML patient will effectively counteract, and/or kill, AML cells. Some embodiments therefore provide an isolated, recombinant or purified antibody, or a functional part or a functional equivalent thereof, that competes with antibody AT14-013 for binding to CD43, for use as a medicament. Some embodiments provide a use of an isolated, recombinant or purified antibody, or a functional part or a functional equivalent thereof, that competes with antibody AT14-013 for binding to CD43, for the preparation of a medicament.

Also provided is an isolated, recombinant or purified antibody, or a functional part or a functional equivalent thereof, that competes with antibody AT14-013 for binding to CD43, for use in a method for at least in part treating or preventing a myelodysplastic or myeloproliferative or lymphoproliferative disorder, as well as a use of an isolated, recombinant or purified antibody, or a functional part or a functional equivalent thereof, that competes with antibody AT14-013 for binding to CD43, for the preparation of a medicament against a myeloproliferative or lymphoproliferative disorder. Said myeloproliferative disorder preferably comprises AML. Further embodiments provide a composition comprising an isolated, recombinant or purified antibody, or a functional part or a functional equivalent thereof, that competes with antibody AT14-013 for binding to CD43. Said composition is preferably a pharmaceutical composition that comprises a pharmaceutically acceptable carrier, diluent or excipient As described herein before, some embodiments provide an isolated, synthetic or recombinant nucleic acid molecule, or a functional equivalent thereof, encoding a CD43 peptide according to the invention. Such nucleic acid molecule or functional equivalent is for instance useful for the production of a CD43 peptide according to the present invention, using a nucleic acid expression system such as for instance host cells. In some embodiments, AML cells are used as host cells. In some embodiments, THP-1 cells are used as host cells. In some embodiments, cells selected from the group consisting of Kasumi 3 cells, HL60 cells, KGla cells, SH2 cells, MonoMac6 cells, Molm 13 cells, and CML K562 cells are used as host cells.

Said nucleic acid molecule or functional equivalent according to the invention is also useful for eliciting an immune response. For instance, a nucleic acid molecule or functional equivalent according to the invention is administered to an AML patient in order to induce or enhance an AML-specific immune response (immunotherapy). In some embodiments, a nucleic acid molecule or functional equivalent according to the invention is administered to an MDS or CML patient in order to delay or prevent the progression of MDS or CML to AML (prophylactic or semi-prophylactic applications). In some embodiments, a nucleic acid molecule or functional equivalent according to the invention is administered to a non-human animal in order to elicit an anti-AML immune response, where after AML-specific antibodies and/or AML-specific immune cells can be harvested from said animal. Alternatively, the variable domain-encoding nucleic acid sequences of AML-specific B cells from said non-human animal are sequenced in order to obtain one or more nucleic acid sequences of AML-specific variable domains, where after one or more nucleic acid molecules comprising AML-specific variable domain sequences are introduced in producer cells for the production of AML-specific antibodies.

In some embodiments, a nucleic acid molecule or functional equivalent according to the invention is present in a gene delivery vehicle, which facilitates introduction of said nucleic acid molecule or functional equivalent into a cell of interest. Further provided is therefore a gene delivery vehicle, preferably a vector, comprising a nucleic acid molecule or functional equivalent according to the invention. A host cell comprising a nucleic acid molecule or functional equivalent according to the invention, and/or comprising a gene delivery vehicle or vector according to the invention, is also provided herewith.

While the current application may describe features as part of the same embodiment or as parts of separate embodiments, the scope of the present invention also includes embodiments comprising any combination of all or some of the features described herein.

The invention is further explained in the following Examples. These Examples do not limit the scope of the invention, but merely serve to clarify the invention.

BRIEF DESCRIPTION OF THE DRAWINGS

FIG. 1. Sequence of AT14-013 (2K23-1K13) including the variable heavy and light chain sequences and the CDR sequences of the antibody.

FIG. 2. Binding of AT14-013 to AML cell lines and freshly isolated primary AML blasts from newly diagnosed patients. FAB: French-American-British classification of AML (Bennett et al. 1976).

AT14-013 did bind to granulocytes (a) and human melanoma cell lines (c). An in-house produced human antibody against influenza was used as a negative control (grey filled histograms).

Figure 6:
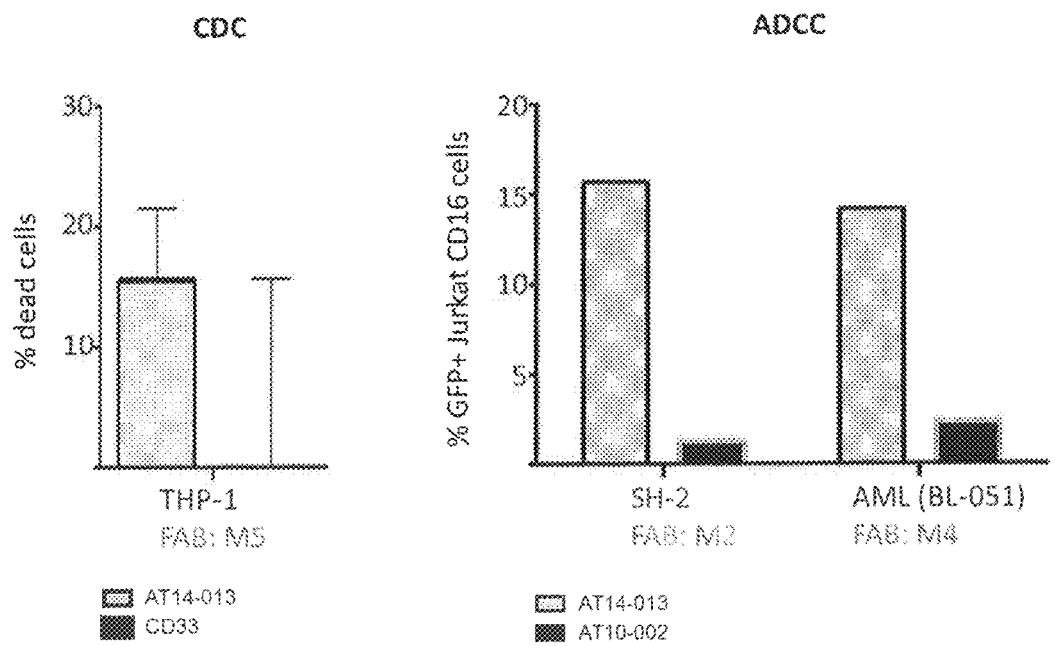

FIG. 6. CDC and ADCC. Calcein labeled THP-1 cells were incubated with AT14-013 and rabbit serum complement. Living cells were identified as calcein+, dapi-cells. With our bead based assay the amount of dead cells could then be calculated as a measure of complement dependent cell death (CDC). Incubation of THP1 cells with CD33 did not induce CDC (left panel). AT14-013 is also able to induce antibody dependent cell cytotoxicity (ADCC) in a Jurkat reporter system with the AML cell line SH-2 or freshly isolated leukemic blasts as target cells (right panel).

Figure 7:
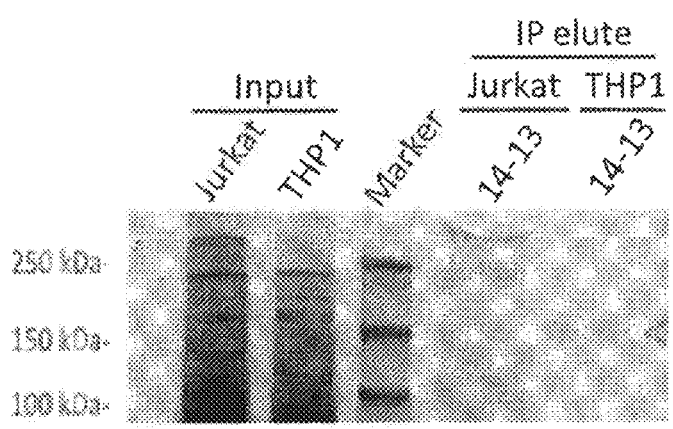

FIG. 7. Target identification of AT14-013: immunoprecipitation (IP). IP with biotin-labeled (via a sortase tag) AT14-013 of THP1 cell lysates yielded a ~140 kDa band on an Imperial Coomassie stained gel. The band is specific as it is not seen in the AT10-002 IP of THP1 lysate or in the Jurkat lysate IP. The band was excised from gel and the target identified as CD43 by mass spectrometry.

FIG. 8. Target confirmation of AT14-013. THP-1 and Molm13 lysates were immunoprecipitated with AT14-013 or with the influenza-specific antibody AT10-002. Western blot analysis with mouse-anti-CD43 (clone Mem59) confirmed CD43 as the binding target of AT14-013.

FIG. 9. AT14-013 binds to a unique CD43 epitope. (a) THP-1 cells were stained with the commercially available CD43 specific antibodies DF-T1, 84-3C1, L10 and Mem59 and with AT14-013. All antibodies bound to the membrane of THP-1 cells. (b) AT14-013 has a different binding profile compared to commercially available CD43-specific antibodies. In Kim ea, (Kim et al. 2014), binding of commercially available CD43 antibodies YGS, 2C8, 8E10 and DFT-1 to various cell lines is summarized. We compared binding of AT14-013 to the same cell lines and found a different binding pattern. (c) A competition experiment with AT14-013 and commercially available CD43 specific antibodies was performed as indicated. Briefly, THP-1 cells were incubated with indicated antibodies at increasing concentrations, after which the possibly competing antibody (referred to as 'competing antibody') was added. AT14-013 binding to THP-1 target cells was not affected by pre-incubation of the cells with commercially available CD43 antibodies, while these commercially available CD43 antibodies did inhibit each other's binding to THP-1 cells. Results are shown for experiments wherein AT14-013 or 84-3C1 was the "competing antibody". (d) Summary of competition experiments. AT14-013 does not compete with commercially available CD43 antibodies for binding to THP-1, indicating that AT14-013 binds a different epitope.

Figure 10:
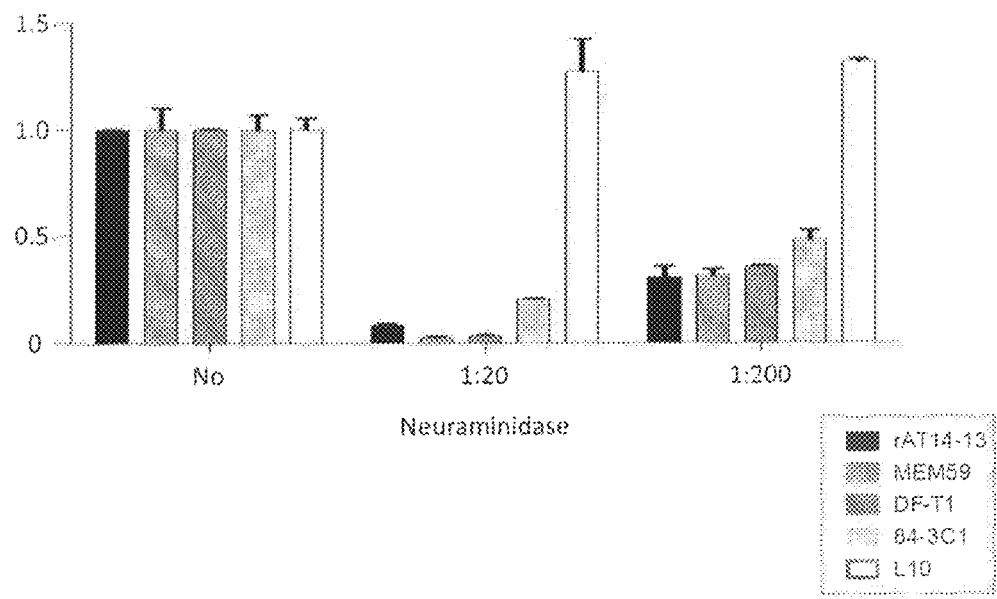

FIG. 10. Deglycosylation of THP-1 cells with neuraminidase (sialidase) removes the sialic acids from the cell membrane. "No" indicates no neuraminidase treatment and "1:20" and "1:200" indicates the neuraminidase dilution. Antibodies AT14-013, Mem59, DF-T1 and 84-3C1 lost binding to THP-1 cells after neuraminidase treatment of these cells. Clone L10 is not binding to a sialilated epitope of CD43, as neuraminidase treatment of THP-1 cells did not affect binding of this antibody to its target cells.

FIG. 11. CD43 truncated variants map the epitopes of commercially available antibodies DF-T1 and MEM59. a) Immunoblot of HEK293T cells expressing truncated variants of CD43 probed with anti-CD43 directed towards the intracellular C-terminal tail of the protein. b) Immunostaining of the same blot with CD43 specific antibodies MEM59 (upper panel) and DF-T1 (lower panel) revealed the presence of their epitope in region 'C' (amino acids 59-82).

Figure 12A:
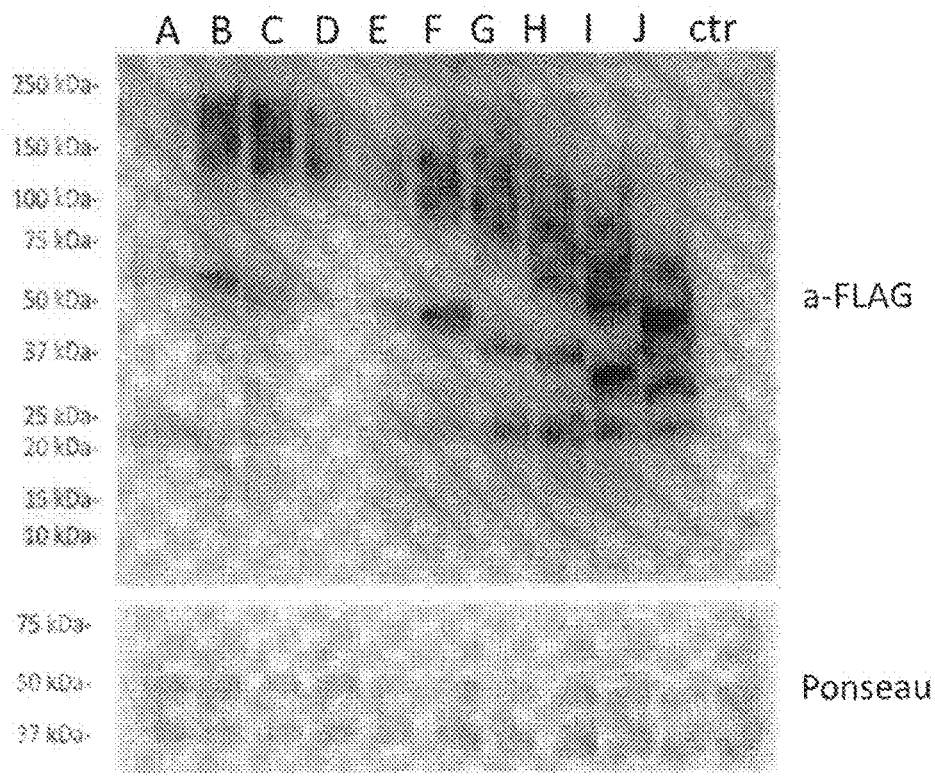
Figure 12B:
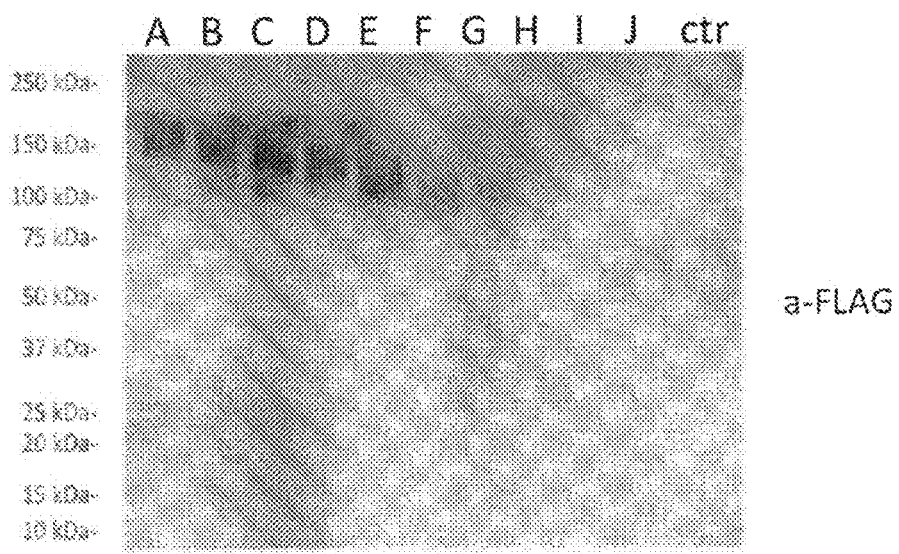

FIG. 12. Immunoprecipitation of CD43 truncated variants from THP1 cells identifies the AT14-013 epitope. a) Immunoblot of input lysates of sorted CD43 truncated variant overexpressing THP1 cells probed with anti-Flag antibody. PonseauS staining demonstrates equal loading of samples. All mutant proteins are expressed. b) Anti-Flag immunoblot of eluted immunoprecipitations of THP1 variant cell lines with AT14-013 reveals binding to mutants A-F and no binding to mutants H-J, defining the epitope. c) Immunoblot with anti-CD43 cytoplasmic tail binding antibody (Novus) showing endogenous immunoprecipitated CD43 in all samples as well as staining of truncated variants.

Figure 13:
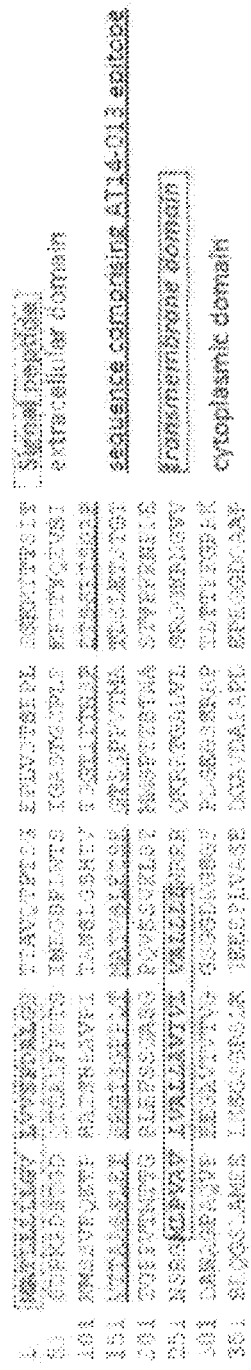

FIG. 13. Amino acid sequence of CD43 (genbank CCDS10650.1). The signal peptide, AT14-013 epitope, transmembrane domain and intra- and extracellular domains are indicated.

FIG. 14. Binding of AT14-013 to other AML blasts. Binding of AT14-013 to freshly isolated primary AML blasts (CD45dim) from newly diagnosed patients. An in-house produced human antibody specific for influenza was used as a negative control. For the commercial mouse anti CD43 antibodies a mouse anti CMV was used as control.

WHO: Swerdlow S. H. WHO classification of Tumours of Haematopoietic and Lymphoid tissues (2008). CD43+ T cells and tonsil cells were used as extra control for the assay. AT14-013 does not bind to these healthy cells.

(% gated=−;<10%,+;10~25%,++;25~50%,+++; 50~75%,++++;75~100%)

FIG. 15. ADCC and CDC.

a) AT14-013 (open squares) is capable of inducing antibody dependent cell mediated cytotoxicity (ADCC) on the AML cell line SH-2 with PBMCs in an effector target ratio of 50:1. Living cells were identified as calcein+, dapi-cells. With our bead based assay the amount of dead cells could then be calculated. Incubation of SH2 cells with AT10-002 did not induce ADCC (black dots). The calculated EC50 for AT14-013 is 0.16 ug/ml.

Calcein labeled SH-2 cells (b) were incubated with AT14-013 (open squares) or AT10-002 (black dots) and rabbit serum complement. Living cells were identified as calcein+, dapi-cells. Incubation of SH2 cells or AML blasts with AT10-002 did not induce CDC (black dots). The calculated EC50 for AT14-013 was 1.86 ug/ml.

FIG. 16.

a) Anti-Flag immunoblot of eluted immunoprecipitations of THP1 variant cell lines with AT14-013 reveals binding to mutants A-F2, binding to a lesser extent to G, and no binding to mutants H-J. b) Immunoblot with anti-CD43 cytoplasmic tail binding antibody (Novus) showing endogenous immunoprecipitated CD43 in all samples as well as staining of truncated variants. This control confirms that the immunoprecipitation was successful for all samples shown.

FIG. 17.

a) Treatment of mice engrafted with SH-2 AML cells leads to a tumor growth inhibition of 90.3% as measured at the sacrifice by whole body measurement ($p<0.001$, repeated ANOVA).

b) The number of AML cells, measured by the number of photon per minute (cpm) exhibits a strong decrease in all the organs measured ($p=0.0011$, repeated 2way ANOVA).

c) Evaluation of the number of tumor cells by FACS in the bone marrow and the liver ($p=0.0017$, 2way ANOVA).

FIG. 18.

Representative examples of binding of AT14-013 to fetal CD34+ hematopoietic stem cells (HSC) but not to fetal CD34+CD38+ progenitor cells or fetal CD34−CD38− mature cells. Grey filled histograms: control antibody AT10-002 directed against influenza, described in WO 2013/081463.

FIG. 19.

AT14-013 reacts with autologous leukemic stem cells.

AML blasts of donor #101 (the same donor from whom the B cells producing AT14-013 were obtained) were stained with AT14-013 and with antibodies specific for CD34 and CD38, and with an antibody against CD45 (BD, cat 348815) to distinguish the general blast population (CD45 dim) from healthy cells in the bone marrow and analyzed by flow cytometry.

EXAMPLES

Example 1

Material & Methods

Patient and Healthy Human Materials

Study protocols were approved by the Medical Ethical Committee of the Academic Medical Centre. All participants signed informed consent. Participants included healthy individuals and patients with hematologic malignancies recruited from our clinic that donated peripheral blood and/or bone marrow.

Generation of AML-specific clone AT14-013

As described in Example 2 of WO 2015/093949, transduced naïve and memory IgG B cells of AML patient 101, immortalized by introduction of Bcl6 and Bcl-xL as described previously (Kwakkenbos et al., Nat Med 2010 and Example 1 of WO 2015/093949), were seeded at a concentration of 20 or 40 cells per well (hereafter named microcultures) and expanded with IL-21 and CD40L. Supernatants of expanded B cell microcultures were then screened for antibody binding to AML cell lines (amongst others THP-1, MonoMac6), and to liver and colon cell lines, by FACS, using human IgG H+L AF647 (Life Technologies) or human-IgG-PE (Southern Biotech) as a secondary antibody. Several in-house generated antibodies were used as negative control antibodies, such as anti-CD30 (expressed on activated B and T lymphocytes), anti-CD33 (expressed on monocytes, myeloid progenitor cells and myeloid leukaemias), D25 (against RSV; described in WO 2008/147196) and AT10-002 (against influenza; described in WO 2013/081463). Microcultures binding to AML cell lines but not to liver and colon cell lines were selected and seeded at a concentration of 1 cell/well and their supernatants tested again for specificity for AML cell lines. Clones with supernatants specifically binding AML cell lines and not liver or colon cell lines, or healthy PBMC and bone marrow were selected for sequencing. Clones were expanded under normal culture conditions in the presence of FBS IgG low serum (Hyclone) and antibodies purified from the supernatants of these cultures as described below for the recombinant antibodies. The recombinant antibodies were then again tested for specific binding. One of the obtained AML-specific antibodies was AT14-013. The discovered AT14-013 antibody was additionally tested on many freshly isolated blasts of newly diagnosed AML patients (FAB M0-M5) for binding, using human IgG H+L AF647 (Life Technologies) as a secondary antibody.

Cloning of AML-Specific Antibody AT14-013

As described in Example 1 of WO 2015/093949, to produce recombinant antibody we isolated total RNA with the RNeasy® mini kit (Qiagen), generated cDNA, performed PCR and cloned the heavy and light chain variable regions into the pCR2.1 TA cloning vector (Invitrogen). To rule out reverse transcriptase or DNA polymerase induced mutations, we performed several independent cloning experiments. To produce recombinant mAb we cloned heavy and light variable regions of each antibody in frame with human IgG1 and Kappa constant regions into a pcDNA3.1 (Invitrogen) based vector and transiently transfected 293T cells. We purified recombinant antibodies from the culture supernatant with Protein A or G, depending on the Ig subtype of the clone.

CDC and ADCC

To quantify complement dependent cell death (CDC) of target cells induced by AML-specific antibody AT14-013 we used a FACS-based leukemia cell lysis assay. THP-1 cells were incubated with 2 μM Calcein AM (Becton Dickinson) for 30 minutes at 37° C. Calcein labeled THP-1 cells were incubated together with antibodies and rabbit serum complement for 4 hours at 37° C. FACS calibration beads (Accudrop Fluorescent Beads, BD Biosciences) were added to the cells in a 50/50 ratio after which a standard amount of beads was acquired with FACS. As an equal assay volume was ascertained by the calibration beads, the amount of dead cells was calculated as: 100−((Dapi negative, Calcein AM positive cells in respective treatment/Dapi negative, Calcein AM positive cells in control)×100). For the antibody dependent cell mediated cytotoxicity (ADCC) we generated a read-out system with Jurkat cells that were stably transduced with NFAT(6×)-IL2 (minimal promoter)-GFP and CD16a (FcR-IIIa). Activation of the CD16a receptor by bound antibody in this system activates NFAT which induces GFP expression that is then used as a read-out to quantify effector cell activation. AML cells (target cells) were incubated with antibodies and mixed with Jurkat cells (effector cells) that were stained with Calcein AM as described above. Effector:target ratio was 1:1.

AT14-013 Target Identification and Validation

THP-1 cells were lysed (0.5% Triton X114 (Sigma), 150 mM NaCl, 10 mM Tris-HCL pH7.4, 1.5 mM MgCl2 supplemented with protease and phosphatase inhibitors (Roche)) and precleared with an irrelevant antibody (in-house generated RSV antibody D25), Protein-G and Streptavidin beads (Pierce) to remove non specific binding proteins. Precleared lysate was then incubated with bead-bound AML-specific antibodies or with the influenza specific antibody AT10-002 as a negative control (3 hrs at 4° C.). Antibody-incubated beads were washed five times in lysis buffer supplemented with 0.5% Deoxycholate and 0.1% SDS, bound proteins were eluted from the beads (0.1M Glycine pH10.5, 150 mM NaCl, 1% Triton X100, 1 mM EDTA) and then run on an SDS-PAGE gel. 85% of IP samples was run on SDS-PAGE and stained with Imperial protein stain (Pierce) to stain total proteins and excise specific bands for Mass Spectrometry. The rest of the IP samples were run on SDS-PAGE and transferred to PVDF membrane (Bio-RAD) for immunoblotting. The blot was stained with Ponseau S to reveal total protein and blocked with BSA, then incubated with mouse-anti-CD43 (clone MEM-59, Abcam) for Western blot analysis.

Epitope Mapping: Competition

THP-1 cells were pre-incubated for 60 minutes on ice with AT14-013 and the commercially available CD43 antibodies: mouse anti human CD43 PE (Ebioscience; clone 84-3C1), mouse anti human CD43 FITC (Invitrogen; clone L10), mouse anti human CD43 FITC (Abcam; clone MEM-59), mouse anti human CD43 unlabeled (Abcam; clone MEM-59), mouse anti human CD43 unlabeled (Thermo Scientific; clone DF-T1). The maximum blocking antibody concentration was 10 ug/ml. Next, the competing antibody was added with a final concentration of 1 ug/ml. With this step, the final concentration of the blocking antibodies is 2 ug/ml. Cells were incubated for 30 minutes on ice, after which dapi (Sigma) was added to exclude dead cells from the analyses. Samples were analyzed by flow cytometry.

Epitope Mapping: Deglycosylation

THP-1 cells were incubated with neuraminidase (Roche; dilution 1:20 or 1:200) for 60 minutes at 37° C. to remove sialic acids from CD43 (de Laurentiis et al. 2011). Cells were then washed, blocked in 60% normal goat serum and incubated with AT14-013 and the commercially available CD43 antibodies DF-T1, 84-3C1, L10 and MEM-59 as described above. To allow comparison of cell staining with different fluorochromes, binding to untreated cells (no neuraminidase) was set to 1. Depicted in FIG. 10 is fold increase/decrease of binding to neuraminidase treated cells.

Epitope Mapping: CD43 Truncated Variants.

CD43 cDNA was obtained from Geneart (Life Technologies) and adapted to contain a 3×FLAG tag in-frame on either C- or N-terminus (C-terminal to the signal peptide, comprising the first 19 amino acids of CD43). The cDNA was cloned into the pHEF-TIG third-generation lentiviral vector containing an IRES-GFP 3' of the CD43 cDNA; VSV-G lentiviral particles were produced in HEK293T cells. THP1, MOLM and other cells were transduced with these viruses in the presence of retronectin and sorted for GFP to obtain a pure population of CD43 overexpressing cells. Truncated CD43 variants were constructed by PCR-cloning of the CD43 C-terminal FLAG-tagged cDNA to contain the signal peptide (AA 1-19) followed by the wild-type full length extracellular sequence (variant A: S20-P400, followed by 3×FLAG: DYKDHDGDYKDHDI-DYKDDDDK) or truncated extracellular sequences (variant B-J). B: 31-400; C: 59-400; D: 82-400; E: 112-400; F: 133-400; G: 166-400; H: 184-400; I: 202-400; J: 220-400 (the transmembrane domain starts at AA 255. These variants were expressed in THP1 cells by lentiviral transduction and GFP sorted. Sorted cells were lysed and immunoprecipitated with AT14-013 and control as described above. Eluted IP samples were run on SDS-PAGE and immunoblotted with anti-FLAG-HRP (Sigma) to reveal binding.

Results

AT14-013 Specifically Binds to AML Cells

In this Example we identify the target of the AML specific antibody AT14-013 that was recently developed in our laboratory (WO 2015/093949 and FIG. 1). This antibody is derived from a patient called patient 101. He was diagnosed with an intermediate-risk AML (no cytogenetic or molecular abnormalities; FAB classification AML-M5) at the age of 49 years. He received two courses of chemotherapy (cytarabine, idarubicine, amsacrine) and one course of consolidation chemotherapy (busulphan, cyclophosphamide) followed by an autologous hematopoietic stem cell transplantation (HSCT), as there was no HLA-matched sibling stem cell donor available. Fourteen months after the first diagnosis his disease relapsed. He obtained complete remission after one cycle of high-dose cytarabine, after which he received a reduced intensity allogeneic HSCT of a matched, unrelated donor (RIST-MUD). Six weeks later he developed acute GvHD of skin, liver and intestine (stage 1; grade II) that responded well to corticosteroid therapy. Given the fact that this patient remained disease free for over 5 years now, despite the high-risk nature of his disease, this patient can be considered to have generated a potent graft versus AML response which was the reason he was selected to search for potent AML-specific antibody responses. B cells were isolated from a phlebotomy product obtained from this patient 38 months post-HSCT, immortalized by introduction of Bcl6 and Bcl-xL as described previously (Kwakkenbos et al., Nat Med 2010) and cultured in 20 or 40 cells/well concentrations. Supernatants of these microcultures were screened for binding to AML cell lines and microcultures specific for AML subcloned in one cell/well concentrations. One of the antibodies identified through this procedure is AT14-013, an IgG1 kappa, highly somatic hypermutated antibody.

Figure 3:
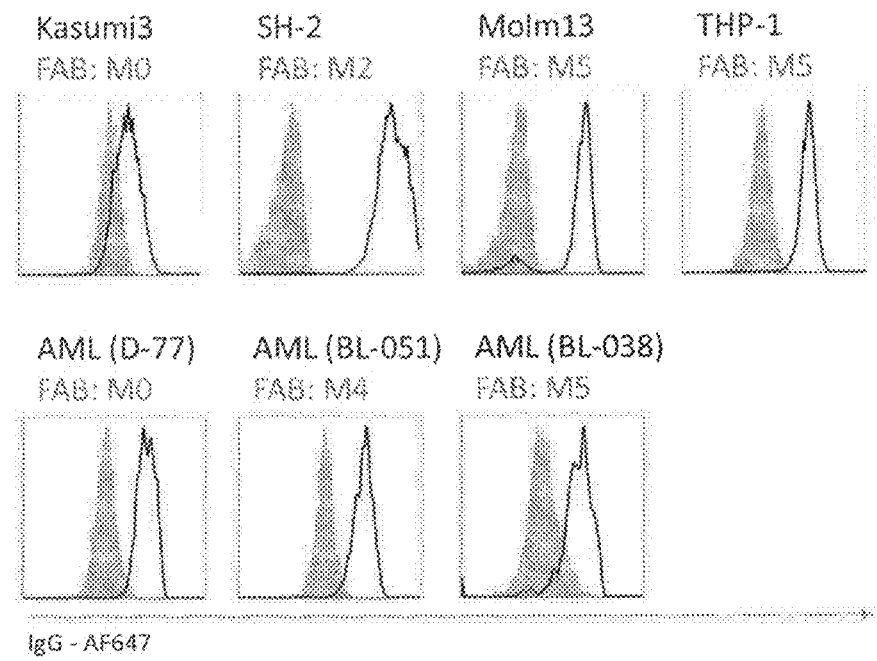
FIG. 3. AT14-013 binds to AML cell lines and primary isolated AML cells. Representative examples of binding of AT14-013 derived from patient 101 to the AML cell lines Kasumi3, SH-2, Molm13 and THP-1 and to primary leukemic blasts isolated from newly diagnosed AML patients (FAB classification M0-M5). An in-house produced human antibody specific for influenza was used as a negative control (grey filled histograms).
Figure 4:
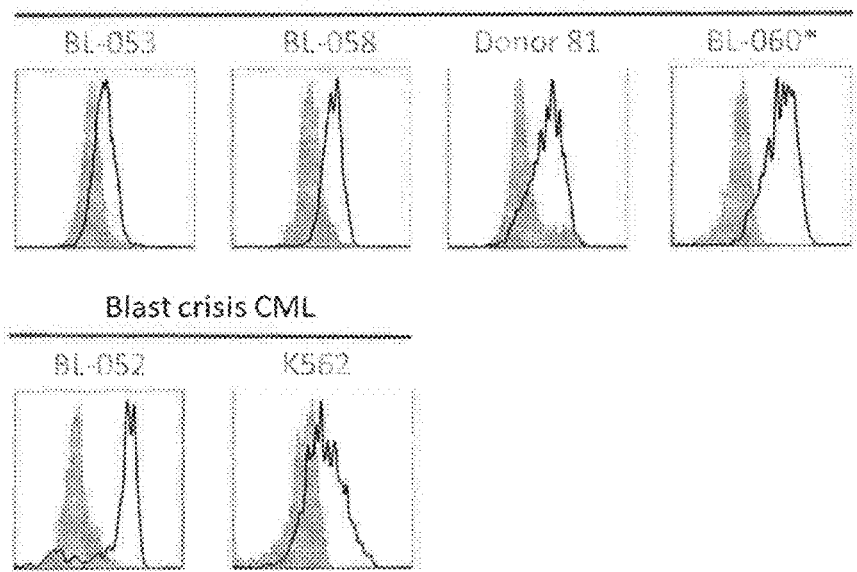
FIG. 4. AT14-013 also binds to leukemic blasts from patients with high-risk myelodysplastic syndrome (MDS/RAEB I and II) and blast crisis chronic myeloid leukemia (CML). Depicted are representative examples; indicated are patient identification codes except K562 which is a CML cell line. An in-house produced human antibody against influenza was used as a negative control (grey filled histograms). *BL-060: biphenotypic leukemia, responding well to AML treatment.
Figure 5A:
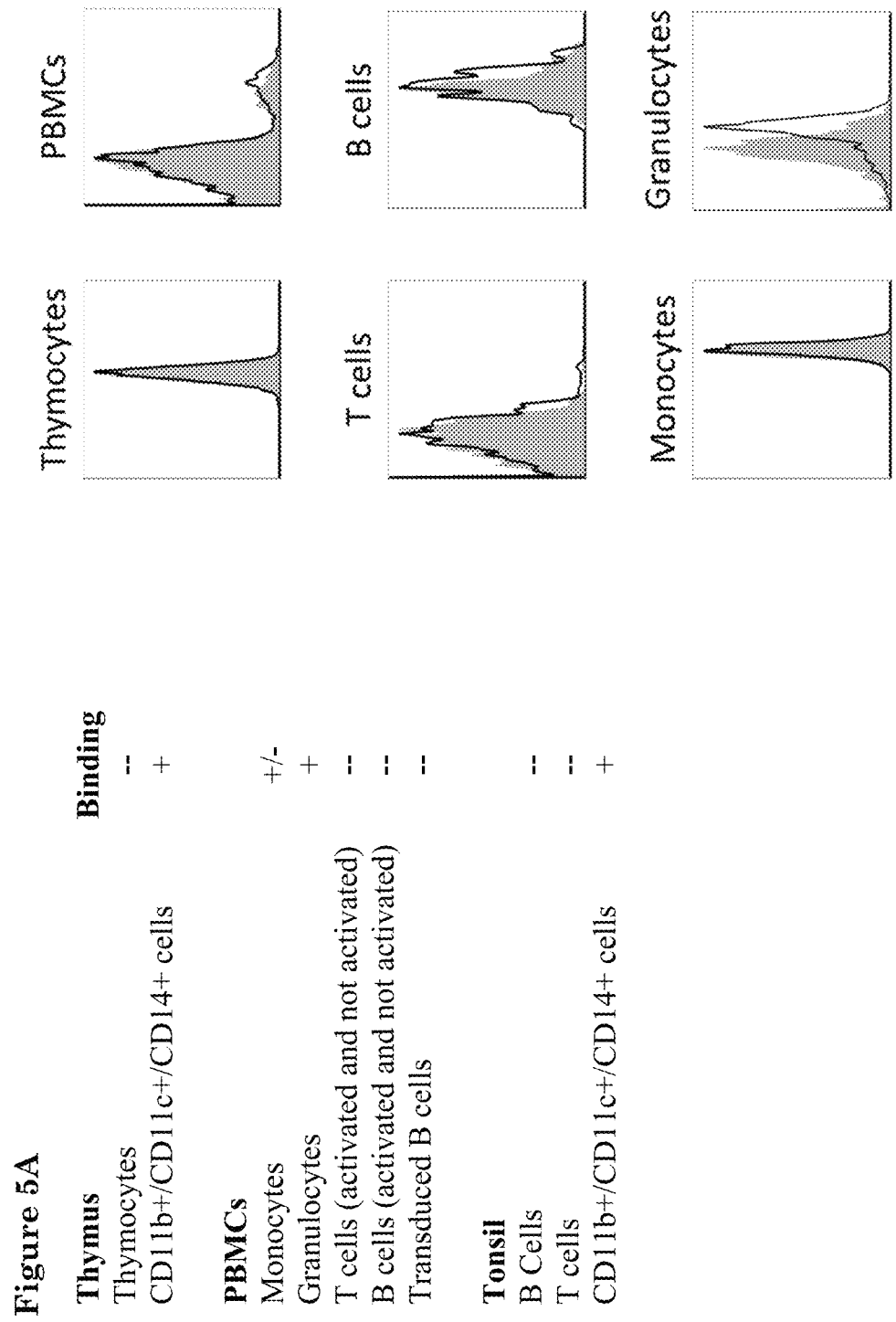
FIG. 5. AT14-013 does not bind to non-myeloid cells. (a) AT14-013 did not bind to healthy PBMCs, T cells (CD3+), B cells (CD19+), non activated monocytes (CD14+) or primary isolated thymocytes (except for a small population of myeloid cells that are present in fetal thymus). (b) AT14-013 also did not bind primary isolated B- or T-ALL cells, lymphoma's or multiple myeloma. (c) AT14-013 also did not bind colon carcinoma cell lines or primary isolated cells from patients with colon carcinoma (Colon CA) or healthy colon or ileum.
Figure 5B:
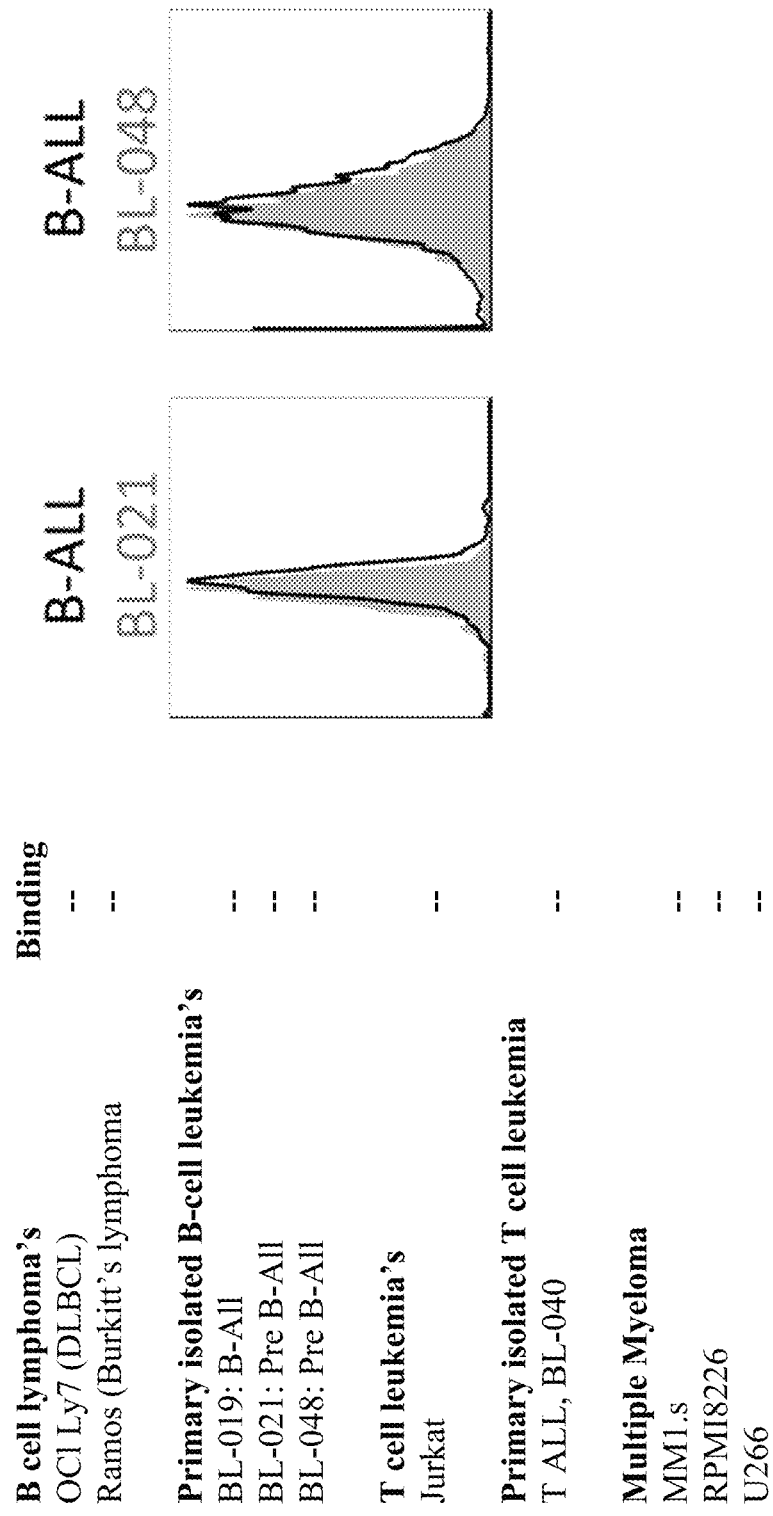
Figure 5C:
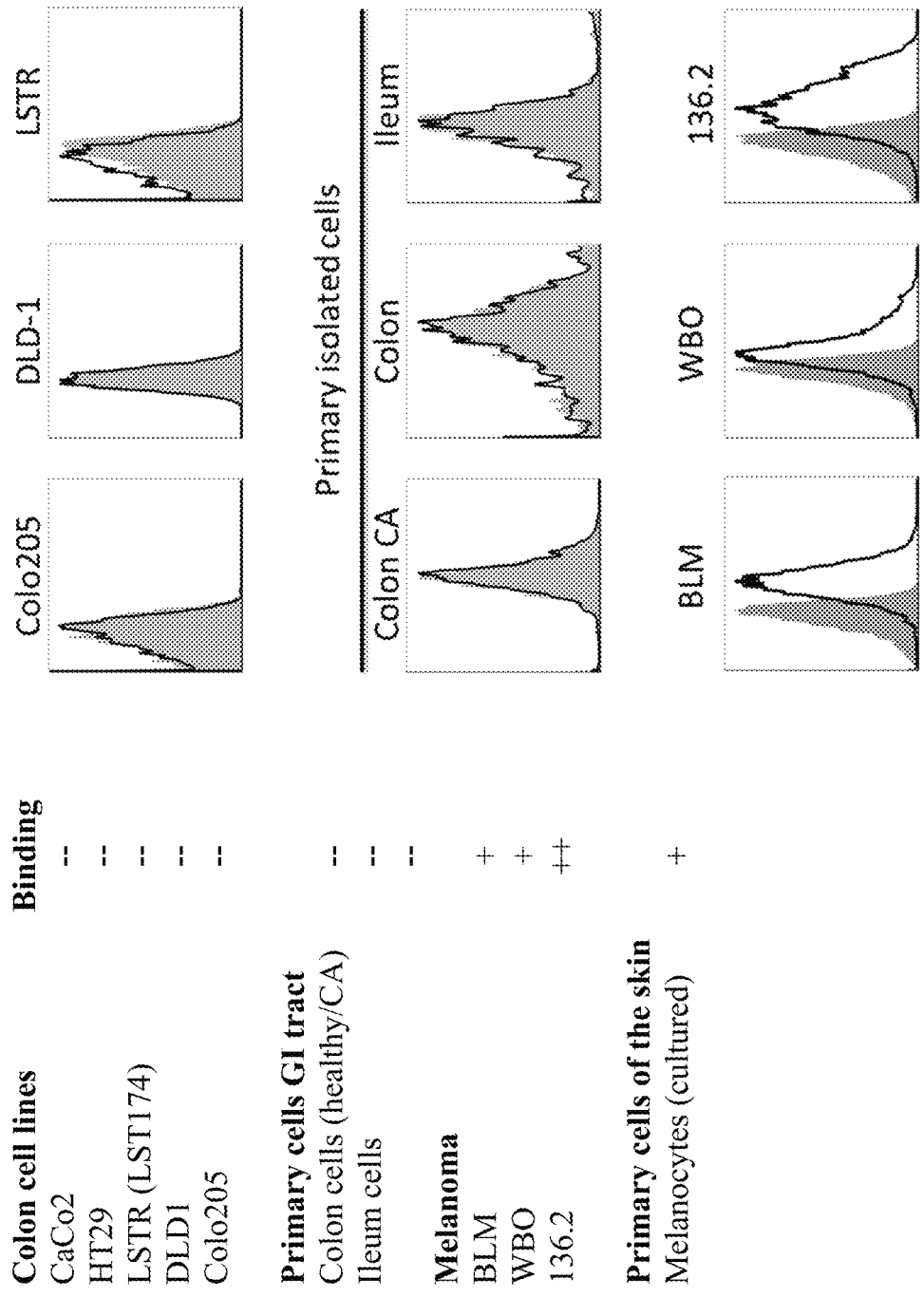

AT14-013 binds specifically to a wide variety of AML cell lines and primary AML cells, covering all AML FAB classifications, as shown in FIG. 2. In FIG. 3, a number of representative examples of AT14-013 binding to Kasumi3, SH-2, Molm13 and THP-1 and to primary leukemic blasts isolated from newly diagnosed AML patients are shown. In addition, AT14-013 binds to other myeloid malignancies such as AML from high-risk myelodysplastic syndrome (MDS/RAEB I/II) or blast crisis chronic myeloid leukemia (CML) and the CML cell line K562 (FIG. 4). AT14-013 did show some binding to granulocytes but did not bind to healthy peripheral blood mononuclear cells (PBMC), bone marrow, thymocytes, hematologic malignancies of the lymphatic lineage or healthy or malignant cells of liver and colon. AT14-013 did bind to cultured melanocytes and melanoma cell lines (FIG. 5).

AT14-013 Induces CDC and ADCC of Target Cells

AT14-013 can induce complement dependent cytotoxicity and antibody dependent cellular cytotoxicity (FIG. 6) of AML cell lines and primary isolated AML blasts.

The Target of AT14-013 is a Unique Epitope of CD43

We then identified the target of AT14-013. Immunoprecipitation (IP) of THP-1 lysate incubated with biotin-labeled sortase-tagged AT14-013 yielded a ~140 kDa band. The band is specific as it was not seen in the AT10-002 IP of THP1 lysate nor in the Jurkat lysate IP (FIG. 7). Mass-spectometry analysis of the immunoprecipitation band revealed CD43 as the target protein. Three out of three expected intracellular peptides were identified, giving a 7% coverage of the protein, extracellular peptides were not identified since these are heavily glycosylated. CD43 binding by AT14-013 was confirmed by western blot analysis. Briefly, THP-1 and Molm13 lysates were immunoprecipitated with AT14-013 or with the influenza-specific antibody AT10-002. Western blot analysis with mouse-anti-CD43 (clone Mem59) confirmed CD43 as the binding target of AT14-013 (FIG. 8).

Figure 9C:
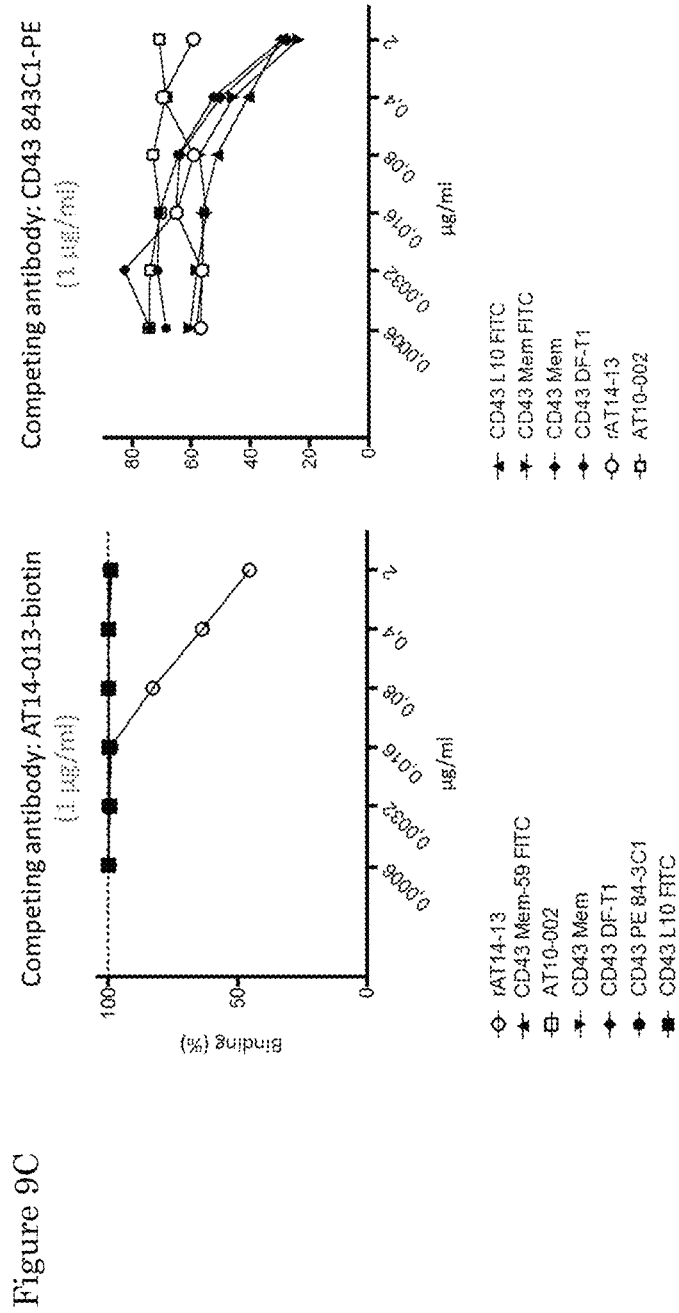
Figure 9D:
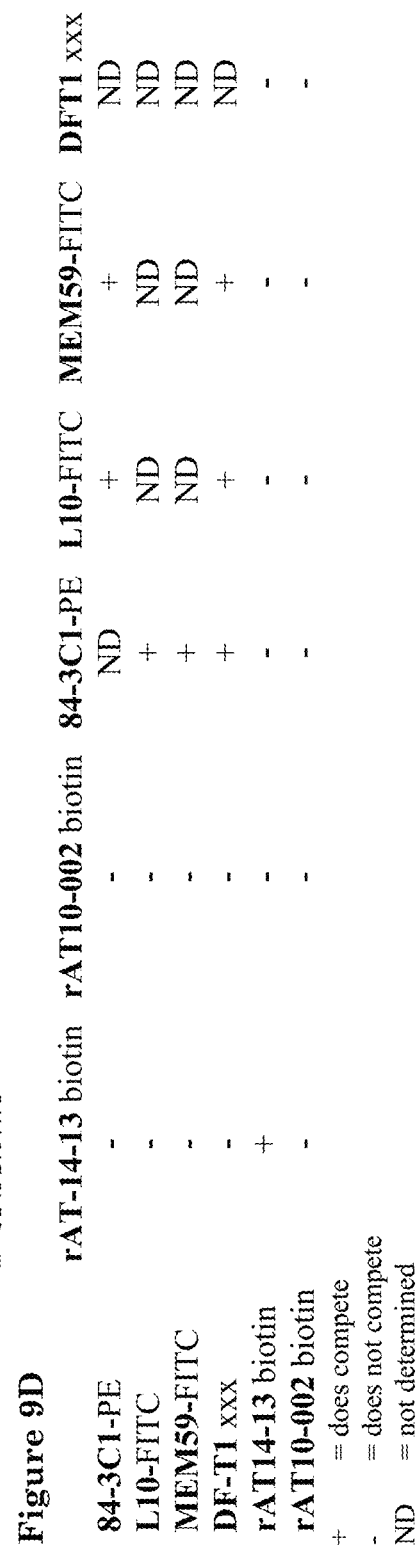

CD43 is widely expressed on healthy and malignant cells. CD43-specific antibodies have been generated and are commercially available, such as DF-T1, 84-3C1, L10 and MEM-59. With these antibodies we confirmed CD43 expression by THP-1 cells (FIG. 9a). The observation that AT14-013 does not bind to non-myeloid cells and the different binding profile of AT14-013 to all sorts of cells and cell lines compared to other CD43 antibodies (FIG. 9b) suggests that AT14-013 recognizes a different CD43 epitope than the other CD43 antibodies. Indeed, when we performed competition experiments, incubating THP-1 cells with commercially available CD43 antibodies and AT14-013, we found that these CD43 antibodies compete with each other for binding to THP-1, but not with AT14-013 (FIG. 9c and FIG. 9d). Of note, CD43 clones L10 and 84-3C1 have been described to compete with each other (L. Borche et al 2005); this is confirmed in our experiment.

The CD43 protein is a highly glycosylated protein (de Laurentiis et al. 2011). The CD43 antibodies Mem59, DF-T1 and 84-3C1 (but not L10) bind to a sialylated epitope, as after pretreatment of target cells with neuraminidase, which removes all α-N-acetylneuramic acids (sialic acids), binding of these antibodies to CD43 is lost (US2010/0234562A1). In FIG. 10 we demonstrate that binding of AT14-013 to THP-1 cells is also lost upon pre-incubation of THP-1 cells with neuraminidase, demonstrating that AT14-013 specifically binds to a sialylated epitope of CD43.

Figure 11A:
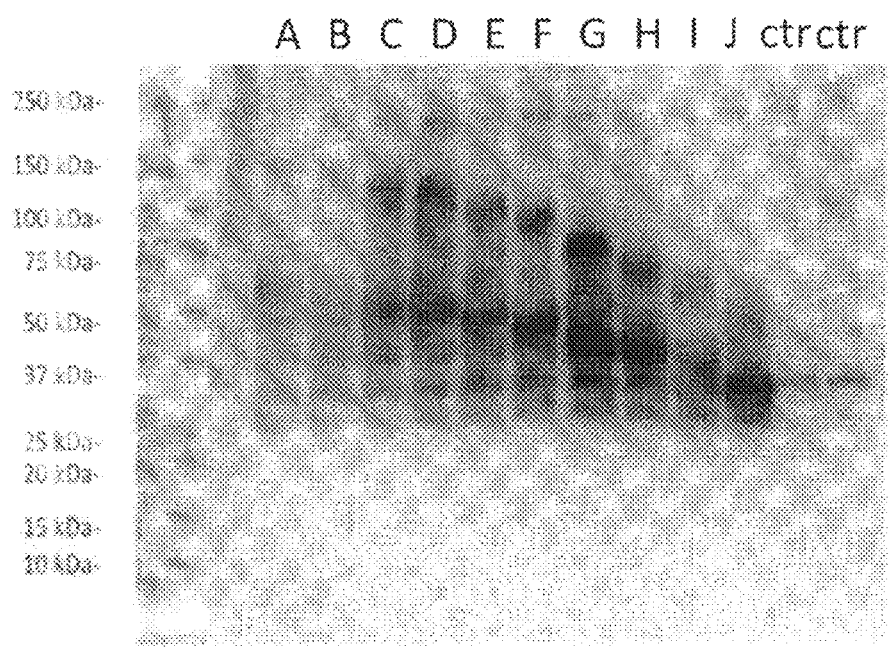
Figure 12C:
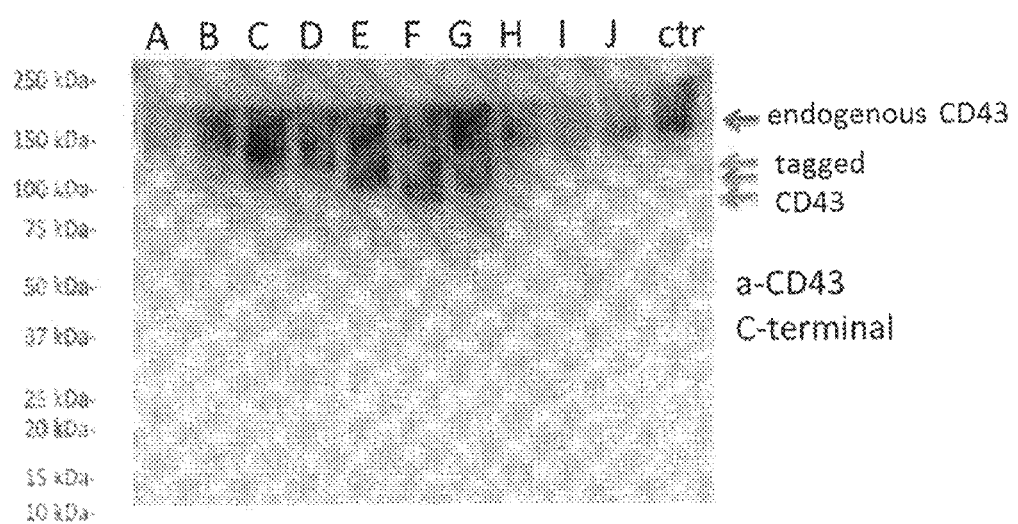

To more specifically identify the binding epitope of AT14-013, we generated 10 Flag-tagged extracellular-truncated variants of CD43 that were expressed in HEK and THP1 cells. Western blot analysis of lysates of these cells incubated with Mem59 or DF-T1 confirmed binding of these antibodies to a similar epitope between amino acids 59-82 (FIG. 11a,b). We tested AT14-013 binding by immunoprecipitation of THP1 cells transduced with these truncation variants. AT14-013 interacts strongly with variants A-F, to a lesser extent with variant G, and not with variants H-J as shown in the anti-Flag immunoblot of the IP's (FIG. 12a,b). In FIG. 12c we confirmed the AT14-013 IP with an anti C terminal CD43 antibody. In all samples endogenous CD43 was present, whereas there was only truncated CD43 present up to variant G. We therefore conclude that the epitope of AT14-013 lies between amino acids 133 and 184.

Example 2

Binding to AML Blasts

Material & Methods

Binding of antibody AT14-013 to different cells was tested using the methodology as described in Example 1 under the heading 'Generation of AML-specific clone AT14-013'. Patient samples were stained with anti human CD45 (BD) prior to the assay. AML cells were defined as CD45dim. Healthy PBMCs were stained with anti human CD3 (biolegend). Polymorph nuclear cells derived from tonsil were isolated by ficol density gradient.

Results

AT14-013 binds specifically to a wide variety of AML cell lines and primary AML cells, covering all AML FAB classifications, as shown in Example 1 and FIG. 4. Additionally, we tested the antibody on a broader panel of AML blasts. It showed to bind to all AML blasts tested so far and often better than the commercial anti CD43 antibodies did. Interestingly, the sialic acid independent L10 antibody was binding the least in almost all samples. In addition the antibodies were tested on healthy CD43 expressing T cells and cells derived from tonsil. Here, only the commercial antibodies showed staining. The results are summarized in FIG. 14.

Example 3

ADCC and CDC

In addition to Example 1 and FIG. 6, another ADCC and CDC experiment was performed.

Material & Methods

To quantify antibody dependent cell-mediated cytotoxicity (ADCC) and complement dependent cellular cytotoxicity (CDC) of target cells induced by AML-specific antibody AT14-013 we used a FACS-based leukemia cell lysis assay. SH2 cells were incubated with 10 nM Calcein AM (Becton Dickinson) for 30 minutes at 37° C. Calcein labeled cells were then incubated together with antibodies and healthy peripheral blood mononuclear cells (PBMCs; Effector:Target 50:1) for 4 hours or rabbit serum complement for 1 hour at 37° C. FACS calibration beads (Accudrop Fluorescent Beads, BD Biosciences) were added to the cells in a 50/50 ratio after which a standard amount of beads was acquired with FACS. As an equal assay volume was ascertained by the calibration beads, the amount of dead cells was calculated as: 100−((Dapi negative, Calcein AM positive cells in respective treatment/Dapi negative, Calcein AM positive cells in control)×100).

Results

AT14-013 Induces CDC and ADCC of Target Cells

AT14-013 can induce antibody dependent cell mediated cytotoxicity (FIG. 15A) and induce complement dependent cytotoxicity (FIG. 15B) of AML cell lines and primary isolated AML blasts.

Example 4

Epitope Mapping: CD43 Truncated Variants

In addition to Example 1 and FIG. 12, the binding epitope of AT14-013 was further investigated.

Material & Methods

The same methods as in Example 1 were used. CD43 cDNA was obtained from Geneart (Life Technologies) and adapted to contain a 3×FLAG tag in-frame on either C- or N-terminus (C-terminal to the signal peptide, comprising the first 19 amino acids of CD43). The cDNA was cloned into the pHEF-TIG third-generation lentiviral vector containing an IRES-GFP 3' of the CD43 cDNA; VSV-G lentiviral particles were produced in HEK293T cells. THP1, MOLM and other cells were transduced with these viruses in the presence of retronectin and sorted for GFP to obtain a pure population of CD43 transduced cells. Truncated CD43 variants were constructed by PCR-cloning of the CD43 C-terminal FLAG-tagged cDNA to contain the signal peptide (AA 1-19) followed by the wild-type full length extracellular sequence (variant A: S20-P400, followed by 3×FLAG: DYKDHDGDYKDHDIDYKDDDDK) or truncated extracellular sequences (variant B-J). B: 31-400; C: 59-400; D: 82-400; E: 112-400; F: 133-400; F2: 148-400; G: 166-400; H: 184-400; I: 202-400; J: 220-400 (the transmembrane domain starts at AA 255). These variants were expressed in THP1 cells by lentiviral transduction and GFP sorted. Sorted cells were lysed and immunoprecipitated with AT14-013 and control as described above. Eluted IP samples were run on SDS-PAGE and immunoblotted with anti-FLAG-HRP (Sigma) to reveal binding.

Results

The Target of AT14-013 is a Unique Epitope of CD43

To more specifically identify the binding epitope of AT14-013, we generated 11 Flag-tagged extracellular-truncated variants of CD43 that were expressed in THP1 cells. We tested AT14-013 binding by immunoprecipitation of THP1 cells transduced with these truncation variants. AT14-013 interacts strongly with variants A-F, to a lesser extent with variant F2, to a lesser extent with variant G, and not with variants H-J as shown in the anti-Flag immunoblot of the IP's (FIG. 16A+B). In FIG. 16b we confirmed the AT14-013 IP with an anti C terminal CD43 antibody. In all samples endogenous CD43 was present, whereas there was only truncated CD43 present up to variant F2. We therefore conclude that the epitope of AT14-013 comprises one or more amino acid residues that are present between amino acids 133 and 165. In view of the fact that AT14-013 interacts to a lesser extent with variant F2 (starting at amino acid position 148 as depicted in FIG. 13), we also conclude that the epitope of AT14-013 at least comprises one or more amino acid residues that are present between amino acids 133 and 147.

Example 5

AT14-013 Inhibits AML Growth in Vivo

Currently known experimental protocols are for instance described in Miller et al., Blood (2013), Vol. 121, No. 5, el-e4.

Figure 17:
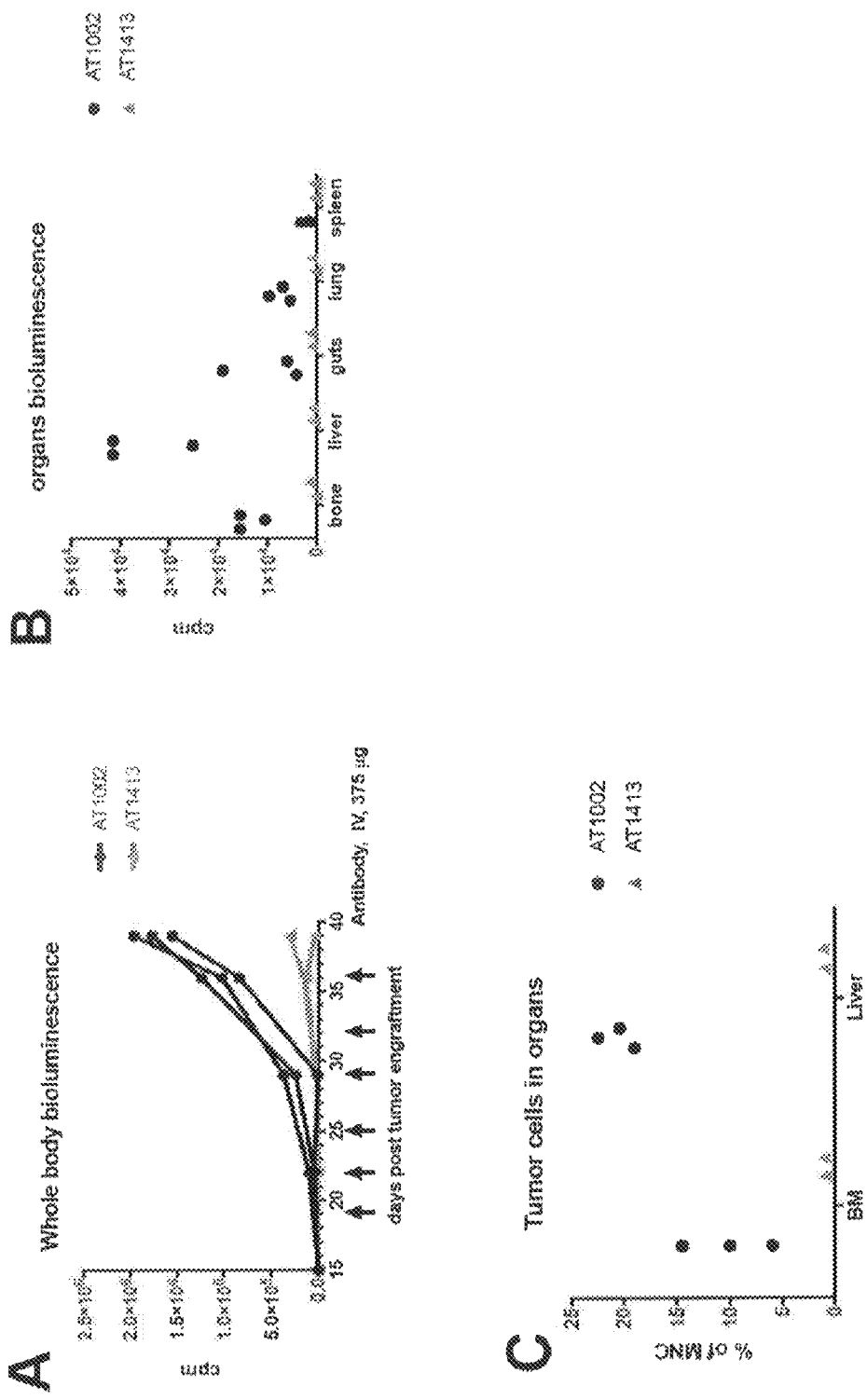

In order to evaluate the efficacy of AT14-013 against AML in vivo, immunodeficient mice reconstituted with human hematopoietic cells and xenografted with SH-2 cells were treated. Six female NOD.Cg-Prkdc$^{seid}$ Il2rg$^{tm1 Wjl/SzJ}$ (NSG, The Jackson Laboratory) were humanized by injecting 50 000 CD34+CD38− hematopoietic stem cells in the liver of sublethally irradiated newborns (1-5 days). At 8 weeks, mice were bled to evaluate the engraftment of human hematopoietic cells in their blood. Only mice with higher than 20% of human chimerism in the peripheral blood were used in this experiment. Five out of 6 mice met this criterion and were intravenously inoculated at d0 with 10×10$^6$ SH-2 cells expressing luciferase and GFP. At d14, mice were injected IP with luciferin (150 mg/kg) and the tumor engraftment was assessed by in vivo bioluminescence. Based on this measurement, mice were randomized in 2 groups and subsequently dosed by iv inoculation of AT14-013 or antibody AT10-002 (against influenza, described in WO 2013/081463, as control) (375 µg) twice per week. The bioluminescence was measured every week as described above. On d39, mice were sacrificed by cervical dislocation under deep anesthesia and the organs were exposed and quantified for bioluminescence. Single-cell suspension was obtained for the liver and the bone marrow and the presence of SH-2 GFP+ cells was quantified by FACS. Treatment of mice engrafted with SH-2 AML cells leads to a tumor growth inhibition of 90.3% as measured at the sacrifice by whole body measurement (p<0.001, repeated ANOVA, FIG. 17A). The number of AML cells, measured by the number of photon per minute (cpm) exhibits a strong decrease in all the organs measured (p=0.0011, repeated 2way ANOVA, FIG. 17B). This observation is confirmed by the evaluation of the number of tumor cells by FACS in the bone marrow and the liver (p=0.0017, 2way ANOVA, FIG. 17C). Hence, an antibody that is specific for a CD43 peptide according to the present invention is particularly suitable for in vivo treatment or prevention of a myeloproliferative or lymphoproliferative disorder such as AML.

Example 6

Material & Methods

Fetal liver, bone marrow and thymus tissue between week 16 and 21 of gestation was obtained from the Human Immune System (HIS) Mouse Facility at the AMC (under Dutch law: Wet Foetaal Weefsel). CD34 enriched mononuclear cell suspensions from tissues were obtained by disrupting whole organs using a Stomacher followed by density gradient centrifugation and magnetic bead separation. CD34 enriched cell suspension of fetal bone marrow was prepared by density gradient centrifugation and magnetic bead separation.

Binding of antibody AT14-013 to cells from fetal liver, fetal thymus and fetal bone marrow was tested by flow cytometry, using commercially available CD34 (BD, cat. 343516) and CD38 (BD, cat. 303522) antibodies to distinguish the different subsets in these samples.

Results

AT14-013 Specifically Binds to an Oncofetal Epitope of CD43

Figure 18:
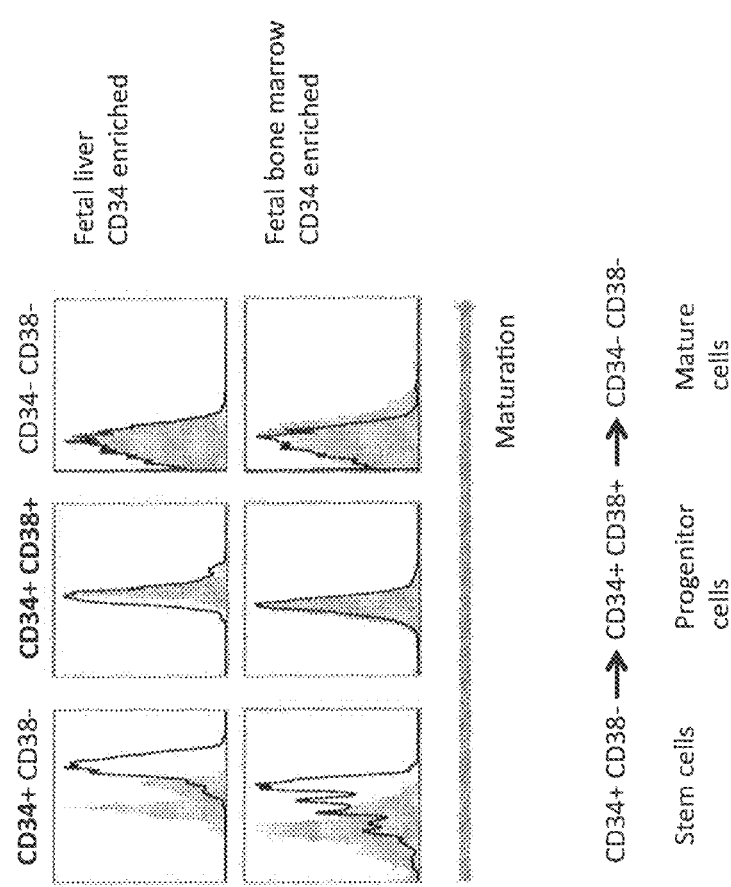

As described herein before, AT14-013 is a CD43-specific antibody that recognizes a unique, onco-sialylated tumor antigen that is expressed predominantly by AML and MDS blasts. Tumor antigens are either abnormal proteins with tumor-specific expression or aberrantly expressed normal proteins such as onco-fetal antigens, which are antigens that are normally only expressed during ontogeny by fetal tissues. Neoplastic transformation of cells is frequently associated with the expression of oncofetal antigens. We found that the AT14-013 epitope of CD43 was expressed by CD34+ CD38− hematopoietic stem cells obtained from fetal liver and fetal bone marrow, but not by CD34+ CD38+ progenitor cells or CD34− CD38− mature cells obtained from fetal liver and fetal bone marrow (FIG. 18). These results demonstrate that AT14-013 is able to bind to an oncofetal-sialylated epitope of CD43 that in adults is widely expressed by AML and MDS.

Example 7

Figure 19:
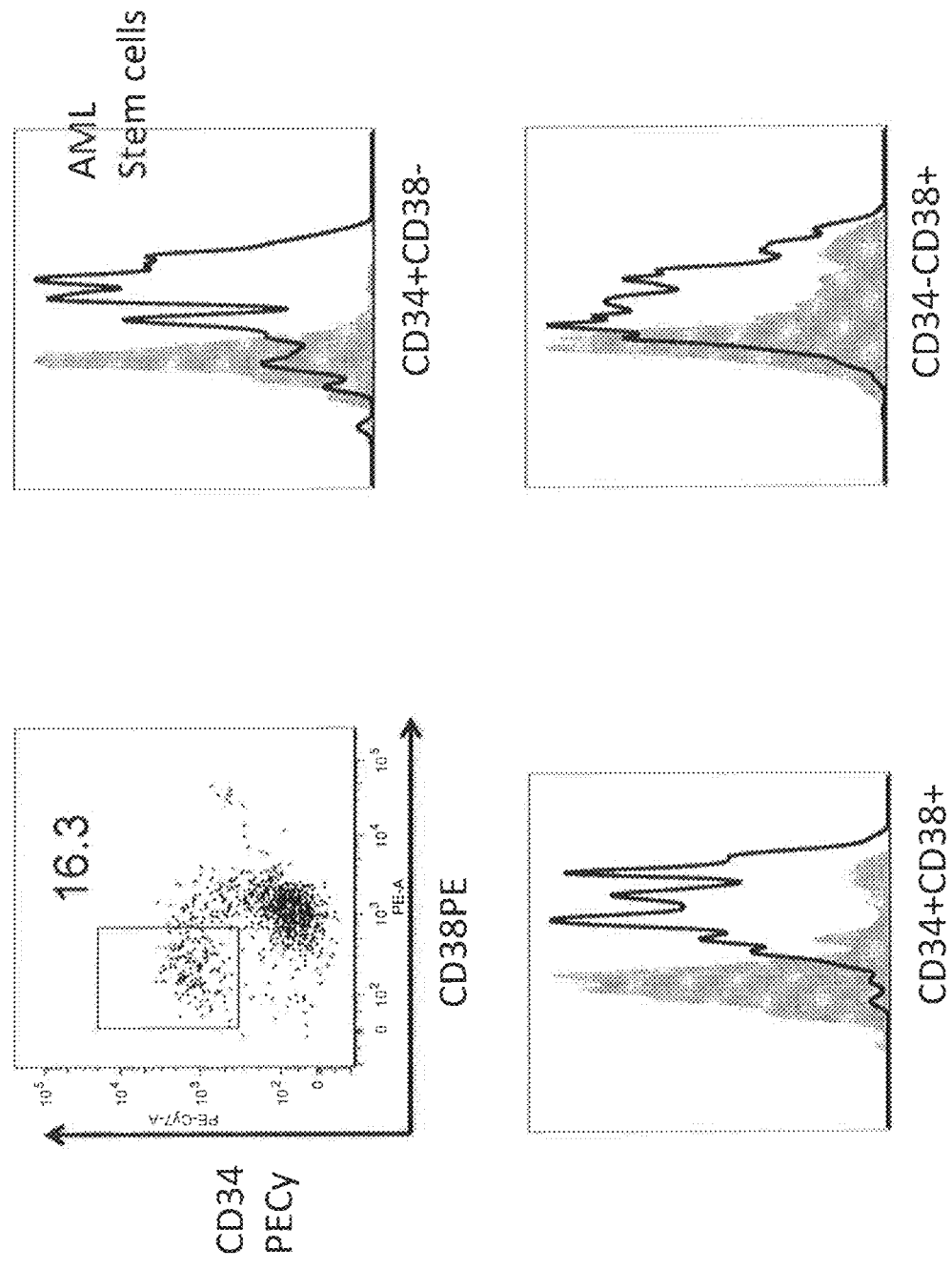

AML blasts of donor #101 (the same donor from whom the B cells producing AT14-013 were obtained) were stained with AT14-013 and with antibodies specific for CD34 and CD38 (same procedure as in Example 6), and with an antibody against CD45 (BD, cat 348815) to distinguish the general blast population (CD45 dim) from healthy cells in the bone marrow and analyzed by flow cytometry (FIG. 19). This shows that AT14-013 binds leukemic blasts of the patient it was found in. AT14-013 binds CD34+CD38− blasts that include the leukemic stem cells.

It is therefore concluded that antibody AT14-013 reacts with autologous leukemic stem cells, which makes AT14-

013 particularly suitable for treatment or prevention of myeloproliferative or lymphoproliferative disorders because it also targets the leukemic stem cells, which are known to be more therapy resistant and often responsible for relapse of disease after treatment.

From this it follows that another antibody that is specific for a CD43 peptide according to the invention, such as an antibody that competes with antibody AT14-013 for binding to CD43, is also particularly suitable for treatment or prevention of myeloproliferative or lymphoproliferative disorders.

REFERENCES

Bennett, J. M. et al., 1976. Proposals for the classification of the acute leukaemias. French-American-British (FAB) co-operative group. British Journal of Haematology, 33(4), pp. 451-458.

Borche, L. et al., 2005. CD43 monoclonal antibodies recognize the large sialoglycoprotein of human leukocytes. European Journal of Immunology, 17(10), pp 1523-1526

European Patent No. 1974017

Hanly et al. Review of polyclonal antibody production procedures in mammals and poultry. ILAR Journal (1995); Vol. 37, Number 3: 93-118

International patent application No. WO 2015/093949
International patent application No. WO 2006/121240
International patent application No. WO 2007/146172

Kim et al. Characterization of two novel mAbs recognizing different epitopes on CD43. Immune Network (2014). Vol. 14, No. 3: 164-170

Kwakkenbos M J et al. Generation of stable monoclonal antibody-producing B cell receptor-positive human memory B cells by genetic programming Nat Med. 2010. 16(1): 123-8.

de Laurentiis, A. et al., 2011. Mass Spectrometry-Based Identification Of The Tumor Antigen UN1 as the Transmembrane CD43 Sialoglycoprotein. Molecular & Cellular Proteomics, 10(5), pp. M111.007898-M111.007898

Malcovati, L. et al., 2013. Diagnosis and treatment of primary myelodysplastic syndromes in adults: recommendations from the European LeukemiaNet. Blood, 122(17), pp. 2943-2964

Miller et al., Blood (2013), Vol. 121, No. 5, el-e4

Schmid K, Hediger M A, Brossmer R, et al. Amino acid sequence of human plasma galactoglycoprotein: identity with the extracellular region of CD43 (sialophorin). Proc. Natl. Acad. Sci. U.S.A. 1992; 89(2):663-667

Shelley et al. Molecular characterization of sialophorin (CD43), the lymphocyte surface sialoglycoprotein defective in Wiskott-Aldrich syndrome. Proc. Natl. Acad. Sci. U.S.A. 1989; Vol. 86: 2819-2823

Swerdlow S. H. WHO classification of Tumours of Haematopoietic and Lymphoid Tissues. International Agency for Research on Cancer, 2008. ISBN: 978-92-832-2431-0

Tuccillo et al. Cancer-associated CD43 glycoforms as target of immunotherapy. Mol. Cancer ther. (2014a) 13(3): 752-762

Tuccillo et al. Aberrant glycosylation as biomarker for cancer: focus on CD43. BioMed research International (2014b) Article ID 742831, 13 pages. http://dx.doi.org/10.1155/2014/742831

U.S. Pat. No. 9,005,974

---

What is claimed is:

1. A recombinant or purified CD43 peptide for AT14-013 antibody binding, said peptide comprising:
the amino acid sequence of SEQ ID NO 3, wherein said peptide has an AML-specific glycosylation pattern or an MDS-specific glycosylation pattern, and wherein the peptide is coupled to a molecular scaffold or a carrier.

2. The peptide of claim 1, said peptide comprising sialic acid residues.

3. The peptide of claim 2, wherein said peptide is neuramidase-sensitive.

4. The recombinant or purified CD43 peptide of claim 1, wherein said peptide is in the context of an MHC complex.

5. An immunogenic composition comprising the CD43 peptide of claim 1.

6. The immunogenic composition of claim 5, wherein said composition is a pharmaceutical composition, said pharmaceutical composition further comprising: a pharmaceutically acceptable carrier, diluent or excipient.

7. A diagnostic kit comprising the CD43 peptide of claim 1.

8. A recombinant or purified CD43 peptide for AT14-013 antibody binding, said peptide comprising:
the amino acid sequence of SEQ ID NO 3, wherein said peptide has an AML-specific glycosylation pattern or an MDS-specific glycosylation pattern, and wherein the peptide is coupled to a molecular scaffold or a carrier; wherein the peptide is coupled to keyhole limpet hemocyanin or a CLIPS scaffold.

9. The peptide of claim 8, wherein the CLIPS scaffold is bis(bromomethyl)benzene, tris(bromomethyl)benzene or tetra(bromomethyl)benzene.

* * * * *